(12) United States Patent
Kawano et al.

(10) Patent No.: US 7,589,839 B2
(45) Date of Patent: Sep. 15, 2009

(54) EXAMINATION APPARATUS, FLUOROSCOPY APPARATUS, EXAMINATION METHOD, AND EXPERIMENTAL METHOD

(75) Inventors: Yoshihiro Kawano, Hachioji (JP); Keiji Shimizu, Fussa (JP); Minoru Sukekawa, Hachioji (JP); Tsuyoshi Mochizuki, Hino (JP); Susumu Honda, Hachioji (JP); Kazuhiro Hayashi, Akishima (JP)

(73) Assignee: Olympus Corporation, Tokyo (JP)

( * ) Notice: Subject to any disclaimer, the term of this patent is extended or adjusted under 35 U.S.C. 154(b) by 259 days.

(21) Appl. No.: 10/594,311

(22) PCT Filed: Mar. 29, 2005

(86) PCT No.: PCT/JP2005/005898

§ 371 (c)(1),
(2), (4) Date: Sep. 27, 2006

(87) PCT Pub. No.: WO2005/096059

PCT Pub. Date: Oct. 13, 2005

(65) Prior Publication Data

US 2007/0273877 A1    Nov. 29, 2007

(30) Foreign Application Priority Data

| Mar. 31, 2004 | (JP) | ............................. 2004-106761 |
| Apr. 2, 2004 | (JP) | ............................. 2004-110427 |
| Nov. 8, 2004 | (JP) | ............................. 2004-324123 |

(51) Int. Cl.
*G01N 21/64* (2006.01)

(52) U.S. Cl. ....................... 356/417; 356/318; 359/368; 359/369; 359/381

(58) Field of Classification Search ................. 359/363, 359/369, 380, 381
See application file for complete search history.

(56) References Cited

U.S. PATENT DOCUMENTS

| 4,661,692 A | 4/1987 | Kawasaki |
| 2001/0003490 A1 | 6/2001 | Kawasaki et al. |
| 2002/0060842 A1* | 5/2002 | Ogino et al. ................. 359/368 |
| 2002/0176160 A1* | 11/2002 | Suzuki et al. ................ 359/380 |
| 2004/0217259 A1 | 11/2004 | Yoneyama et al. |

FOREIGN PATENT DOCUMENTS

| JP | 59-172617 | 9/1984 |
| JP | 05-093845 A | 4/1993 |

(Continued)

*Primary Examiner*—F. L Evans
(74) *Attorney, Agent, or Firm*—Pillsbury Winthrop Shaw Pittman, LLP

(57) ABSTRACT

A microscope examination apparatus is provided that includes a light source for emitting excitation light or illumination light to a specimen placed on a stage; an objective lens opposing the stage and capable of focusing fluorescence or reflected light from the specimen; an image-forming lens for forming an image of the specimen obtained by the objective lens; and an image-capturing unit for capturing the image of the specimen forming by the image-forming lens, wherein a plurality of the objective lenses having different magnifying powers is provided, and an objective-lens switching mechanism for switching among the objective lenses is provided, and wherein a plurality of the image-forming lenses having different magnifying powers is provided, and an image-forming-lens switching mechanism for switching among the image-forming lenses is provided.

28 Claims, 37 Drawing Sheets

FOREIGN PATENT DOCUMENTS

| | | |
|---|---|---|
| JP | 07-104192 | 4/1995 |
| JP | 07-248450 | 9/1995 |
| JP | 09-236751 A | 9/1997 |
| JP | 10-509817 A | 9/1998 |
| JP | 2001-166214 | 6/2001 |
| JP | 2003-5079 * | 1/2003 |
| JP | 2003-207717 | 7/2003 |
| WO | WO 96/10794 A | 4/1996 |

\* cited by examiner

EXAMINATION APPARATUS, FLUOROSCOPY APPARATUS, EXAMINATION METHOD, AND EXPERIMENTAL METHOD

This is the U.S. National Stage of International Patent Application No. PCT/JP2005/005898, filed on Mar. 29, 2005, which, in turn, relies for priority upon Japanese Patent Application No. 2004-106761, filed Mar. 31, 2004, Japanese Patent Application No. 2004-110427, filed Apr. 2, 2004, and Japanese Patent Application No. 2004-324123, filed Nov. 8, 2004, the contents of all of which are hereby incorporated by reference in their entireties.

TECHNICAL FIELD

The present invention relates to examination apparatuses and fluoroscopy apparatuses for examining a living organism, organ, or tissue.

BACKGROUND ART

A conventionally known microscope examination apparatus is described in Patent Document 1. This microscope examination apparatus includes an objective lens disposed opposite to a specimen, an image-forming lens configured to form an enlarged image on an image-capturing unit, such as a CCD camera, and a magnifying relay lens detachably disposed between the objective lens and the image-forming lens and capable of continuously changing the magnifying power within a specific range of magnifications.

According to this microscope examination apparatus, even when the objective lens and the image-forming lens are fixed and an afocal magnifying relay lens is detachably disposed therebetween, the confocal point on the image-capturing plane does not change and degradation of the image caused by the magnification is small. Thus, operability and performance are improved.

Furthermore, conventionally, when examining a living organism, organ, or tissue, a microscope or a stereo microscope is used to illuminate the upper surface or the lower surface of the living organism, organ, or tissue to obtain a fluorescence image, a reflective image, or a transmission image. When examining a reflective image or a fluorescence image using an endoscope, the inside of the living organism is illuminated and image capturing is carried out inside the living organism.

Patent Document 1: Japanese Unexamined Patent Application Publication No. HEI-7-104192 (FIG. 1, etc.)

DISCLOSURE OF INVENTION

However, a known microscope examination apparatus changes the examination magnification by changing the magnification of the afocal magnifying relay lens. Therefore, it is difficult to carry out magnification within a wide range of magnifications. In other words, since the same objective lens and image-forming lens are used from low magnification to high magnification, there is a problem in that, when the magnification is low, the numerical aperture becomes significantly small, and the resolution is reduced.

For known examination apparatuses, when the specimen to be examined is a living organism, organ, or tissue, as the thickness of the specimen increases, the illuminated light is more easily absorbed. Therefore, it becomes difficult to efficiently illuminate the examination site of the living organism, organ, or tissue.

As the thickness of the living organism, organ, or tissue increases, autofluorescence increases. Therefore, it becomes difficult to examine the examination site of the living organism, organ, or tissue at high resolution.

The present invention has been conceived in light of the problems described above. An object of the present invention is to provide an examination apparatus and a fluoroscopy apparatus that are capable of obtaining a high-resolution image without significantly decreasing the numerical aperture when magnification is decreased and that are capable of improving the examination accuracy.

Another object of the present invention is to provide a technology for efficiently illuminating a living organism, organ, or tissue and examining it at high resolution.

To achieve the above-identified objects, the present invention provides the following solutions.

A first aspect of the present invention provides an examination apparatus comprising a light source for emitting excitation light or illumination light to a specimen placed on a stage; an objective lens opposing the stage and capable of focusing fluorescence or reflected light from the specimen; an image-forming lens for forming an image of the specimen obtained by the objective lens; and an image-capturing unit for capturing the image of the specimen forming by the image-forming lens. A plurality of the objective lenses having different magnifying powers is provided, and an objective-lens switching mechanism for switching among the objective lenses is provided. A plurality of the image-forming lenses having different magnifying powers is provided, and an image-forming-lens switching mechanism for switching among the image-forming lenses is provided.

According to this aspect, when excitation light or illumination light generated at the light source is emitted to the specimen, fluorescence or reflected light from the specimen is incident on and focused at the objective lens, is incident on and imaged at the image-forming lens, and is captured at the image-capturing unit. To change the magnification of the image of the specimen, the objective-lens switching mechanism is operated to switch the objective lens. Then, the image-forming-lens switching mechanism can be operated to select an image-forming lens suitable for the objective lens. As a result, even when the magnifying power is reduced, an image can be obtained at high resolution without significantly reducing the numerical aperture.

According to this aspect, a relay optical system for relaying illumination light for illuminating the specimen and a reflecting member that is held by an image-forming lens and that is capable of deflecting the illumination light from the light source toward the relay optical system may be provided.

In this way, the path of the illumination light can be separated from the path of the return light from the specimen. Therefore, the illumination light is not transmitted through the objective lens, and the generation of autofluorescence at the objective lens can be reduced. As a result, an image having good contrast can be obtained. Moreover, for example, in the case where the illumination light is excitation light and the return light is fluorescence, the size of the dichroic mirror for separating the excitation light and the fluorescence can be reduced, which allows an inexpensive illumination system to be provided.

According to this aspect, a relay optical system for relaying illumination light for illuminating the specimen and a rotary turret for holding a plurality of dichroic mirrors and a reflecting member which deflects the illumination light from the light source toward the relay optical system and for selectively disposing the dichroic mirrors and the reflecting member opposite the light source may be provided.

In this way, an illumination system capable of freely switching between on-axis illumination and off-axis illumination, whichever is suitable for the examination method, can be provided.

According to this aspect, the relay optical system may be held by the objective lens or the objective-lens switching mechanism.

In this way, the examination region of an objective lens can be thoroughly illuminated, and an efficient illumination system can be provided.

For the above-described structure, it is preferable that the relay optical system splits the illumination light from the light source into two or more beams and emits the two or more beams to the specimen from different directions.

In this way, the generation of shadows on the specimen can be suppressed, and an illumination system capable of obtaining an examination image having good contrast can be provided.

According to this aspect, a zooming mechanism inserted, on an optical axis, and between an objective lens having a high magnifying power and an image-forming lens having a high magnifying power, when an objective lens having a high magnifying power and an image-forming lens having a high magnifying power are selected may be provided.

For the above-described structure, it is preferable that the zooming mechanism is provided in a manner such that the zooming mechanism is removable from the optical axis when an objective lens having a low magnifying power and an image-forming lens having a low magnifying power are selected.

Since the numerical aperture can be relatively large when an objective lens having a high magnifying power and an image-forming lens having a high magnifying power are selected, the zooming mechanism can be inserted to continuously change the magnifying power. In this case, when an objective lens having a low magnifying power and an image-forming lens having a low magnifying power are selected, by removing the zooming mechanism from the optical axis, it is possible to employ a combination of an objective lens and an image-forming lens that maintains the numerical aperture. To change the magnifying power from high to low by using only the zooming mechanism, the numerical aperture at low magnification decreases significantly. Therefore, such an adverse effect can be prevented by removing the zooming mechanism.

For the above-described structure, it is preferable that a parfocal adjustment mechanism for adjusting the image location of the image-forming lenses be provided.

If the image location of the image-forming lens changes due to individual variations of the image-forming lens and the objective lens to be combined and the zooming mechanism, this change can be compensate for by the operation of the parfocal adjustment mechanism, and an even clearer image can be obtained.

According to the first aspect of the present invention, it is preferable that an optical-path bypass unit be provided, the optical-path bypass unit being disposed on the image-forming lens having a high magnifying power and being capable of bypassing the optical path between the image-forming lens having a high magnifying power and the image-capturing unit so that the straight-line distance from the image-forming lens having a high magnifying power to the image-capturing unit is matched with that of the image-forming lens having a low magnifying power.

By positioning the image-forming lens and the objective lens so that their rear focal positions substantially match, i.e., so that they are in a telecentric positional relationship, the optical performance, such as aberrations, can be improved. As in the first aspect of the present invention, when image-forming lenses having different magnifying powers are switched while maintaining their positional relationship, the optical path length increases at high magnification because of a difference in the focal lengths. Thus, the optical-path-bypass unit is operated to match the straight-line distance from the image-forming lens having a high magnifying power to the image-capturing unit and the straight-line distance from the image-forming lens having a low magnifying power to the image-capturing unit. In this way, clear images can be obtained for all magnifying powers without moving the image-capturing unit.

In the above-described structure, an optical-path-length adjustment unit capable of adjusting the optical path length of the optical-path bypass unit may be disposed on the optical-path bypass unit.

It is preferable that an angle adjustment unit for adjusting the inclination angle of the optical axis of the optical-path bypass unit be disposed in the optical-path bypass unit.

When the image-forming lenses are different, the optical path lengths and the optical axes differ due to individual variations of the lenses. Therefore, by operating the optical-path-length adjustment unit, the optical path length is matched with that of the reference image-forming lens, and by operating the angle adjustment unit, the angle is adjusted so that the optical axis of the image-forming lens is accurately directed toward the image-capturing unit.

According to the above-described first aspect, an objective parfocal adjustment mechanism for adjusting the optical axis direction and position of the objective lens may be provided.

By operating the objective parfocal adjustment mechanism, the individual difference among lenses can be compensated for by adjusting the position of the objective lens conjugate with the image location of the image-forming lens.

According to the above-described first aspect, the objective lenses, the zooming mechanism, and the image-forming lenses may be attached on the same axis disposed in the vertical direction and may be attached in a manner such that they are rotatable around the axis. In this way, a switching mechanism having a compact structure can be constructed.

According to the above-described first aspect, the objective lenses, the zooming mechanism, and the image-forming lenses may be attached in a manner such that they are rotatable around at least two axes that are disposed in the vertical direction, and the objective lenses and the zooming mechanism may be attached in a manner such that they are rotatable around different axes.

The objective lenses having different magnifying powers are disposed at different positions in the optical axis direction according to the difference of the focal length. At high magnification, the objective lens is disposed close to the specimen, whereas at low magnification, the objective lens is disposed away from the specimen. By rotating the objective lenses and the zooming mechanism around different axes, at low magnification the objective lens and the zooming mechanism that are not used simultaneously can be disposed at positions that interfere with each other in the optical axis direction, thus enabling a structure that is compact in the height direction.

In the above-described structure, a horizontally mounted base, at least two support stands extending from the base in the vertical direction along the axes, and a beam member bridged across the upper ends of the support stands may be provided, and the image-capturing unit may be fixed to the beam member.

In this way, the image-capturing unit can be stably fixed to the beam member supported by at least two support stands, and the vibrations of the image-capturing unit can be suppressed to improve the examination accuracy.

In the above-described structure, it is preferable that the optical axis be disposed at a position away from a plane including the axes of the at least two support stands. In this way, the support stands can be disposed close to each other, and the width can be reduced.

In the above-described structure with the objective lenses, zooming mechanism, and image-forming lenses being provided along one or at least two axes disposed in the vertical direction and being provided in a manner such that they are rotatable around the axes, it is preferable that the objective lenses, the zooming mechanism, and the image-forming lenses be attached to the support stand in a manner such that they are rotatable around the axis of the support stand by an assembly including a cylindrical fixed bracket fixed to the support stand by being engaged with the upper portion of the support stand; a movable bracket for fixing the objective lenses, the zooming mechanism, and the image-forming lenses; and a bearing for installing the movable bracket to the fixed bracket in a manner such that the movable bracket is horizontally rotatable.

By employing such a structure, by engaging and fixing the fixed bracket of the externally assembled assembly, the movable bracket can be rotatably supported by the support stand. Thus, assembly is easy, and production, maintenance, and adjustment can be easily carried out.

In the above-described structure with the objective lenses, zooming mechanism, and image-forming lenses being provided along one or at least two axes disposed in the vertical direction and being provided in a manner such that they are rotatable around the axes, it is preferable that the base include a first base for fixing the stage and a second base provided above the first base with a space provided therebetween, and wherein the first base and the second base are fixed by spacing members and the support stands are fixed to the second base.

By employing such a structure, the spacing dimension of the spacing members can be set independently from the distances between the support stands fixed to the second base. As a result, the spacing dimension of the spacing members may be increased to provide space around the stage so as to increase the ease-of-operation when handling the specimen.

By proving replaceable spacing members, the spacing members can be changed to spacing members having different lengths in accordance with the size of the specimen, and space can be provided around the stage.

In the above-described structure, a tray member for fixing the specimen may be fixed to the stage while being positioned.

In this way, the specimen can be fixed to the tray member in a location other than on the stage, and then the tray member to which the specimen is fixed can be fixed to the stage. Since the objective lenses are close to each other, the space around the stage is relatively small. Thus, in some cases, ease-of-use is not sufficient for carrying out the procedure for fixing the specimen, such as a small laboratory animal. Therefore, by carrying out such a procedure externally and by carrying out only the procedure for attaching the tray member to the stage under the objective lens, preparation for examination can be easily carried out.

In the above-described structure, it is preferable that the tray member be composed of a transparent material or a light-absorbing material.

In this way, since the illumination light among the light that is emitted from above the specimen and that is not incident on the specimen is transmitted through the tray member or is absorbed by the tray member, this light is prevented from returning to the objective lens as stray light.

According to the above-described first aspect, it is preferable that the image-capturing unit be replaceable.

In this way, an image-capturing unit suitable for the type of specimen and examination method can be selected and used, and an image suitable for the object being examined can be obtained.

According to the above-described first aspect, it is preferable that the image-capturing unit be disposed in a manner such that it is rotatable around the optical axis.

By rotating the image-capturing unit around the optical axis, the direction of the obtained image can be arbitrarily-selected. To connect the image-capturing unit to a monitor and carry out examination in real-time, the orientation of the image displayed on the monitor can be arbitrarily-selected, and examination can be carried out in a direction enabling easy viewing.

The second aspect of the present invention provides a fluoroscopy apparatus including a laser light source for emitting excitation light to a specimen placed on a stage; a plurality of lens groups, each group including an objective lens for expanding fluorescence from the specimen and opposing the stage, and an image-forming lens for imaging the fluorescence from the specimen expanded by the objective lens; an image-capturing unit for capturing the fluorescence from the specimen imaged by the image-forming lens; and a lens-group-switching mechanism for switching among the lens groups.

According to this aspect, to carry out examination by changing the magnifying power, the lens-group-switching mechanism is operated to switch among the lens groups each including an objective lens and an image-forming lens. Therefore, even when low magnification examination is carried out, a bright image can be obtained without significantly reducing the numerical aperture.

According to this aspect, a processing unit for carrying out spectral deconvolution processing on the captured fluorescence may be provided, and the processing unit may carry out spectral blind deconvolution processing.

The third aspect of the present invention is directed to an examination apparatus for a living organism, an organ, or tissue. The examination apparatus according to the third aspect includes an illumination device for internally illuminating a living organism, organ, or tissue and an image-capturing device for obtaining an optical image of at least one of a transmission image and a fluorescence image of the living organism, organ, or tissue obtained by capturing the external image of the living organism, an organ, or tissue. The illumination device may include a light source for emitting illumination light or excitation light and a light-emitting unit for externally emitting illumination light or excitation light. The light-emitting unit can be guided into the living organism, organ, or tissue.

The fourth aspect of the present invention is directed to an examination apparatus for a living organism, an organ, or tissue. With the examination method according to this aspect, a light-emitting unit for externally emitting illumination light or excitation light is guided into a living organism, organ, or tissue; the living organism, organ, or tissue is internally illuminated by emitting illumination light or excitation light from a light-emitting unit; an optical image of at least one of a transmission image and a fluorescence image of the living organism, organ, or tissue is obtained by capturing an external image of the living organism, organ, or tissue; and the obtained optical image is displayed on a display device.

The fifth aspect of the present invention is directed to an examination apparatus for a living organism, an organ, or tissue. With the experimental method according to this aspect, a light-emitting unit for externally emitting illumination light or excitation light is guided into a living organism, organ, or tissue; the living organism, organ, or tissue is internally illuminated by emitting illumination light or excitation light from the light-emitting unit; a fluorescence image of the living organism, organ, or tissue is obtained by capturing an external image of the living organism, organ, or tissue; and the changes over time in the amount and area of fluorescent substances in the living organism, organ, or tissue are compared and studied by comparing the obtained fluorescence image with other images.

According to the first and second aspects of the present invention, the objective lens can be switched in accordance with the change in magnifying power, and, at the same time, the image-forming lens can also be switched. In particular, by switching the objective lens to an objective lens having a low magnifying power and also switching the image-forming lens to a image-forming lens having a low magnifying power when examining a specimen at low magnification, advantages are provided in that the numerical aperture can be maintained without be significantly reduced, and reduction in the resolution of the obtained image is suppressed so as to improve the examination accuracy.

According to the third to fifth aspects of the present invention, a technology for efficiently illuminating a living organism, organ, or tissue and examine it at high resolution is provided.

BEST MODE FOR CARRYING OUT THE INVENTION

First Embodiment

A microscope examination apparatus according to a first embodiment will be described below with reference to FIGS. 1 to 15.

Figure 1:
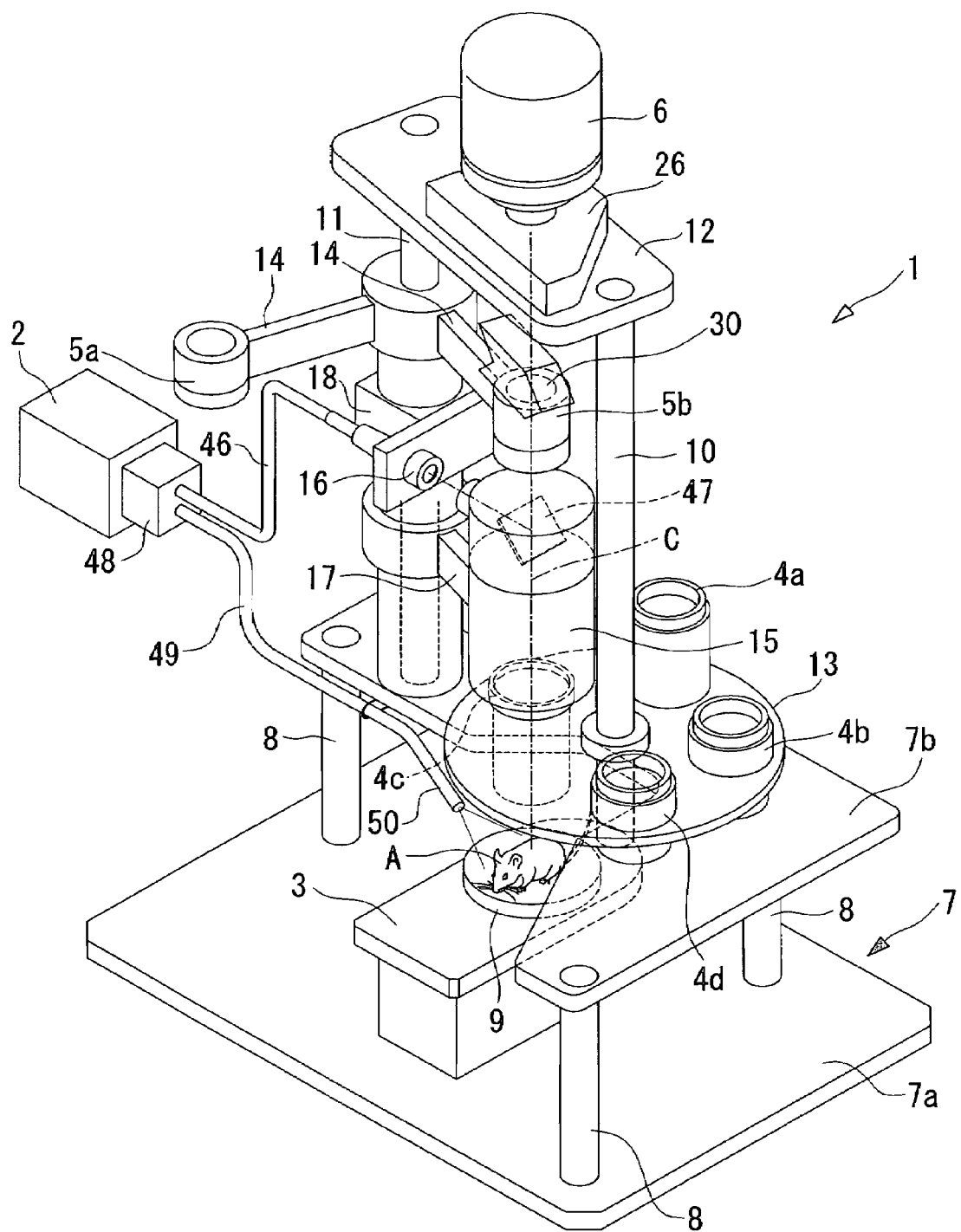
FIG. 1 is a perspective view illustrating a microscope examination apparatus according to a first embodiment of the present invention.

As shown in FIG. 1, a microscope examination apparatus 1 according to this embodiment includes a light source 2 configured to generate light emitted to a specimen A of a small laboratory animal or the like, such as a mouse, a stage 3 where the specimen A is disposed, objective lens units 4a to 4d configured to enlarge the return light from the specimen A, image-forming lens units 5a and 5b configured to enlarge and form a image of the specimen A enlarged by the objective lens units 4a to 4d, and a camera (image-capturing unit) 6 configured to capture the image of the specimen A formed by the image-forming lens units 5a and 5b.

The stage 3 is provided on a horizontally disposed base 7. The base 7 includes a first base 7a that is disposed on a horizontal mounting surface and a second base 7b horizontally disposed above the first base 7a, with space provided therebetween. A plurality of spacing members 8 for setting the distance between the two bases are disposed in such a manner that they can be inserted and removed between the first base 7a and the second base 7b.

Figure 2:
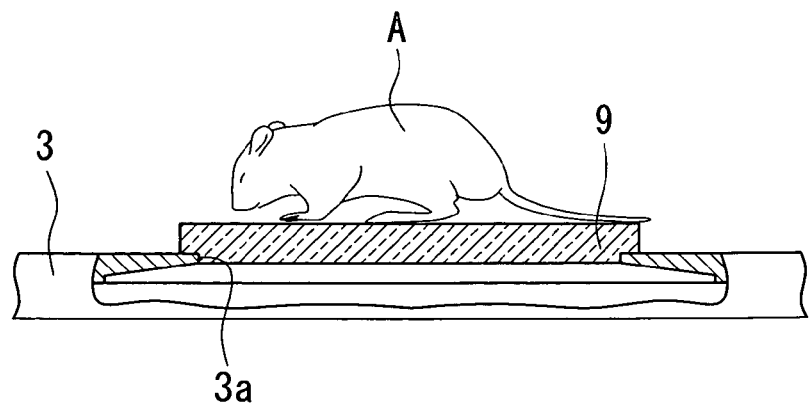
FIG. 2 is a partially cutaway longitudinal cross-sectional view illustrating a tray member on a stage of the microscope examination apparatus illustrated in FIG. 1.

The stage 3 is disposed on the first base 7a, and the specimen A disposed on the stage 3 can be moved in two horizontal directions and the vertical direction. As shown in FIG. 2, a through hole 3a is formed in the stage 3. A tray 9 on which the specimen A is disposed is aligned and fitted in the through hole 3a. According to this embodiment, the tray 9 is composed of a transparent material or a black material that absorbs light.

The second base 7b is disposed above the stage 3. The second base 7b is notched so that the second base 7b does not block the space above the entire operating area on the stage 3. The spacing members 8 are disposed around the stage 3 at sufficient distances away from the operating area of the stage 3. In this way, a large space is provided so as not to cause obstruction when the operator disposes the specimen A on the stage 3 or manipulates the specimen on the stage 3.

Two support stands 10 and 11 vertically extend from the upper surface of the second base 7b. The upper ends of the two support stands 10 and 11 are connected to an upper plate (beam member) 12 that is bridged across the support stands 10 and 11. In this way, a gate-like frame constituted of the two support stands 10 and 11 and the upper plate 12 is constructed on the second base 7b.

The objective lens units 4a to 4d are attached to a turret 13 which is attached to the first support stand 10. The turret 13 is rotatable around the vertical axis of the support stand 10.

The objective lens units 4a to 4d are fixed to the turret 13 so as to be spaced from each other in the circumferential direction. As shown in FIGS. 3 to 6, these objective lens units 4a to 4d have different magnifying powers. For example, the objective lens units may have focal lengths of 50 mm, 90 mm, 180 mm, and 300 mm in order from the unit having the shortest focal distance. The operator can select one of the objective lens units 4a to 4d having the desired focal lengths by turning the turret 13 when necessary. In the drawings, lenses are not illustrated.

The image-forming lens units 5a and 5b, i.e., the low-magnification image-forming lens unit 5a and the high-magnification image-forming lens unit 5b, are attached to the tips of two first arms 14 which are attached to the second support stand 11 in a manner such that the first arms 14 are rotatable around the vertical axis of the second support stand 11. The low-magnification image-forming lens unit 5a has a focal length of 75 mm, and the high-magnification image-forming lens unit 5b has a focal length of 210 mm.

A zooming mechanism 15 configured to continuously change the magnifying power on the high-magnification side and an illumination device 16 for epi-illumination during high-magnification examination are attached to the second support stand 11 in a manner such that they are independently rotatable around the vertical axis of the second support stand 11. As shown in the drawing, the zooming mechanism 15 is attached to the tip of a second arm 17 rotatably attached to the second support stand 11. The illumination device 16 is fixed to a bracket 18 that is rotatably attached to the second support stand 11. The combined magnifying power of the objective lens units 4a to 4d, the image-forming lens units 5a and 5b, and the zooming mechanism 15 when at high magnification is 1.26 to 16.2 times.

Figure 7:
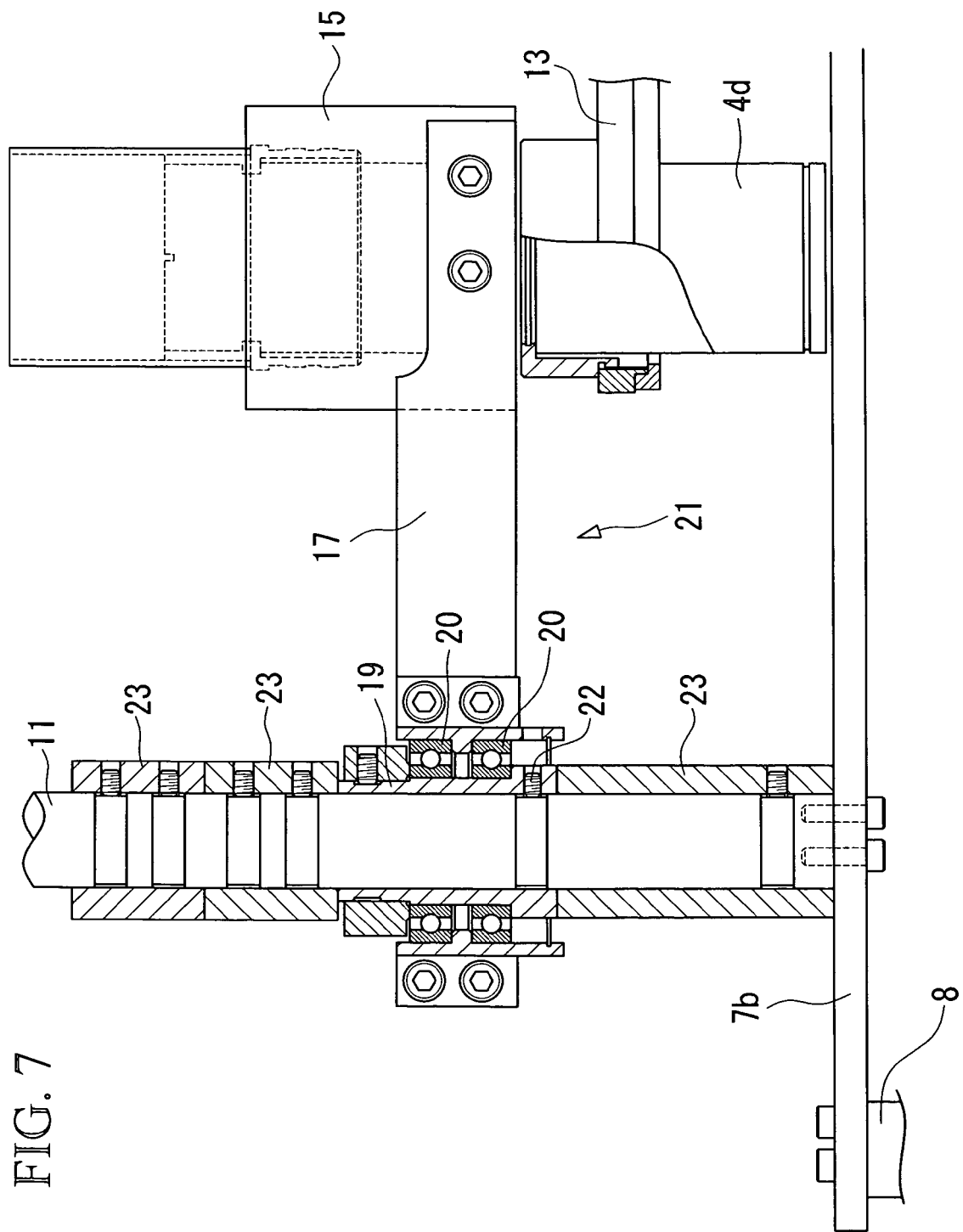
FIG. 7 is a partially cutaway longitudinal cross-sectional view illustrating an attachment structure of a second arm of the microscope examination apparatus illustrated in FIG. 1.

As shown in FIG. 7, the turret 13, the first arms 14, the bracket 18, and the second arm 17 are rotatably attached to a cylindrical fixing bracket 19 engaged with the support stand 10 and 11 with bearings 20 interposed therebetween so as to constitute an assembly 21. FIG. 7 illustrates the second arm 17 as an example. The assembly 21 is engaged with the first support stand 10 and the second support stand 12 from the upper ends thereof when the upper plate 12 is removed and is disposed at specific positions. The fixing bracket 19 is fixed to the support stands 10 and 11 by screwing in a locking screw 22 in the radial direction. In this way, the assembly 21 can rotate horizontally to the specific positions.

The assembly 21 is engaged with the support stands 10 and 11 from the upper ends and is brought into direct contact with the upper surfaces of sleeves 23 that are positioned in contact with the upper surface of the second base 7b and the upper surface of the assembly 21 or adjustment spacers (not shown in the drawings) to set the vertical positions of the components. In other words, the assembly 21 and the sleeves 23 are engaged with the support stands 10 and 11 when the upper plate 12 is removed and are stacked onto each other. In this way, the assembly 21 and the sleeves 23 can be easily positioned.

Figure 8:
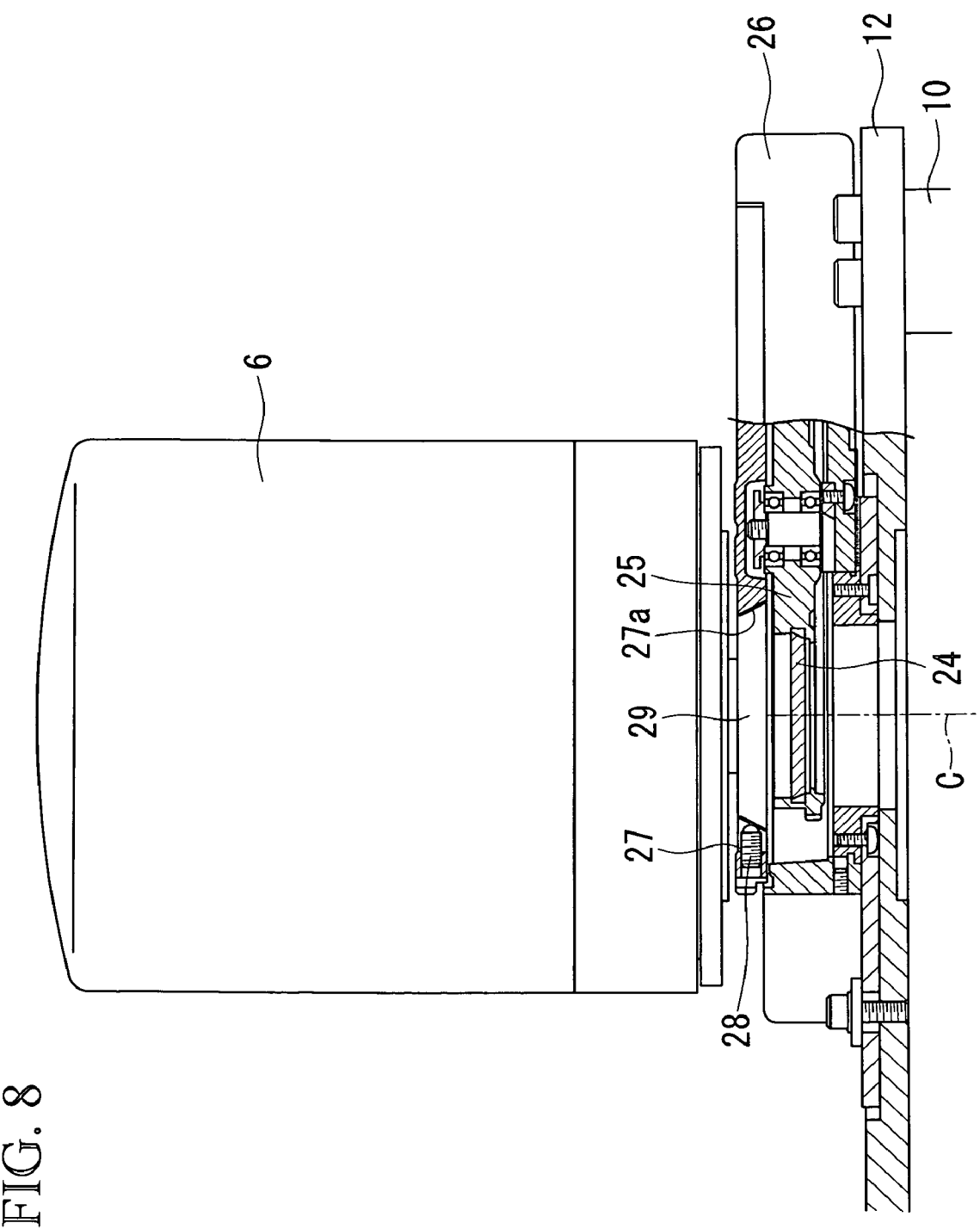
FIG. 8 is a partially cutaway longitudinal cross-sectional view illustrating an attachment structure of a camera of the microscope examination apparatus illustrated in FIG. 1.

As shown in FIG. 8, the camera 6 is disposed fixed on the upper plate 12 with the optical axis C extending vertically downwards. Absorption filters 24 are interposed between the upper plate 12 and the camera 6. Various different types of absorption filters 24 are attached to a turret 25 in such a manner that they are rotatable around the vertical axis so that only the light to be captured passes therethrough.

Figure 9:
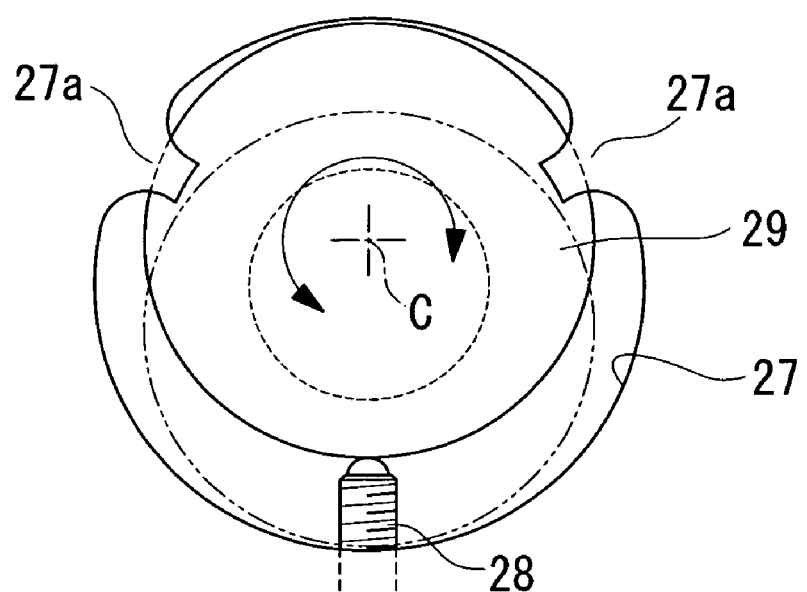
FIG. 9 is a plan view illustrating the attachment structure of FIG. 8.

As shown in FIGS. 8 and 9, an attachment hole 27 having a female dovetail part 27a is provided in a casing 26 of the absorption filters 24. The camera 6 has a dovetail boss 29 that is inserted into the attachment hole 27 and engaged with the female dovetail part 27a by being horizontally urged with a locking screw 28. The boss 29 is tapered in a manner such that the external diameter increases toward the tip thereof. As indicated by the arrows in FIG. 9, by loosening the locking screw 28, the camera 6 can be rotated around the optical axis C while remaining engaged with the female dovetail part 27a.

The optical axis C of the camera 6 is interposed between the two support stands 10 and 11. As represented by the hatched area in FIG. 11, the position of the optical axis is set at a point where a circle with a radius A and a circle with a radius C intersect, wherein the following expressions are satisfied:

$$C < D < L - r_1 \quad (1)$$

$$L - C < A < B < L - r_2 \quad (2)$$

where L represents the distance between the axes of the two support stands 10 and 11, A represents the turning radius of the optical axes of the objective lens units 4a to 4d centered on the axis of the first support stand 10, B represents the radius of the outermost arc of the objective lens units 4a to 4d, C represents the turning radius of the optical axis of the image-forming lens units 5a and 5b centered on the axis of the second support stand 11 and the zooming mechanism 15, D represents the radius of the outermost arc of the image-forming lens units 5a and 5b and the zooming mechanism 15, $r_1$ represents the radius of the first support stand, and $r_2$ represents the radius of the second support stand 11.

Figure 10:
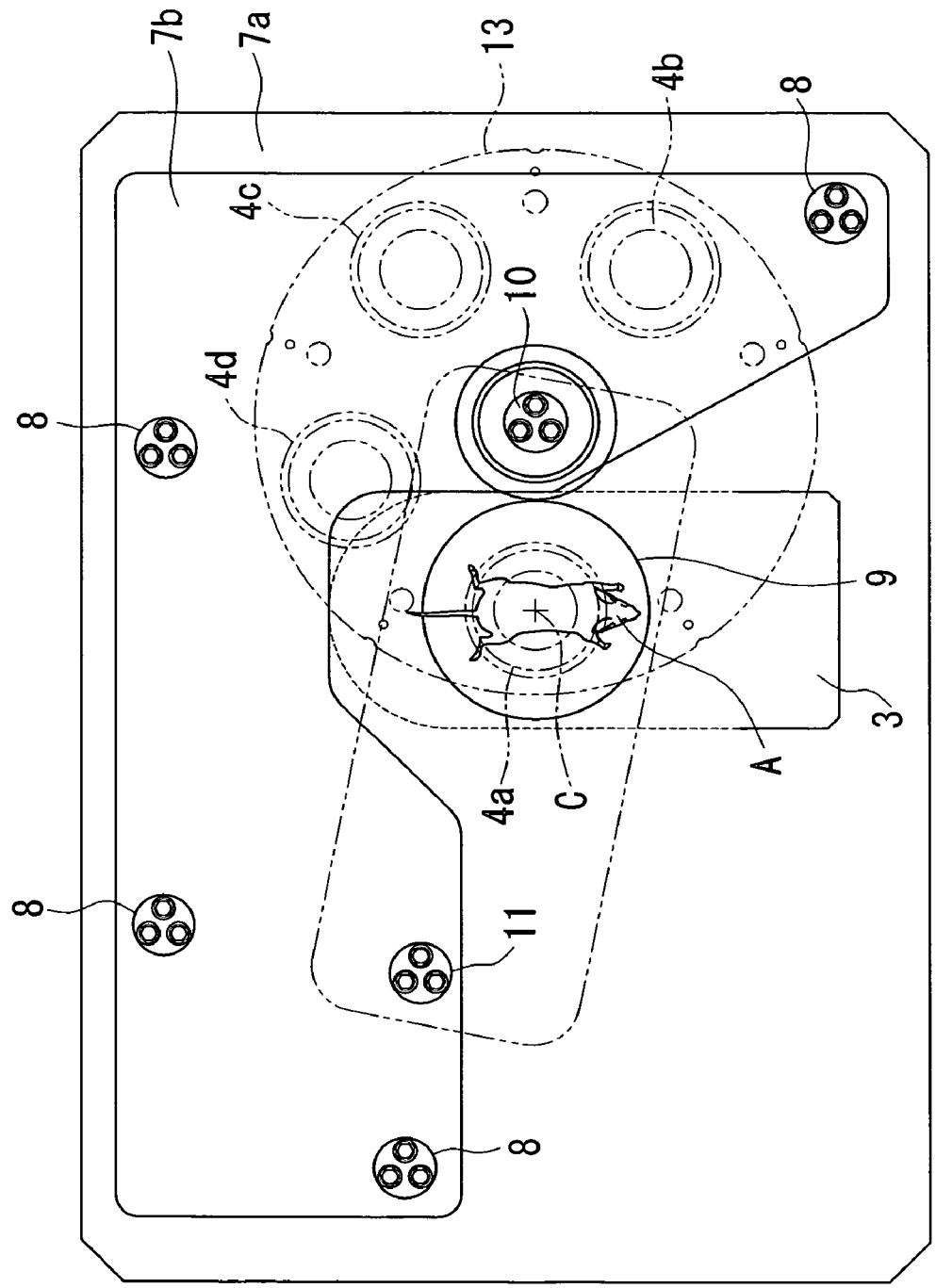
FIG. 10 is a plan view illustrating the positioning of a support stand and a spacing member of the microscope examination apparatus illustrated in FIG. 1.
Figure 11:
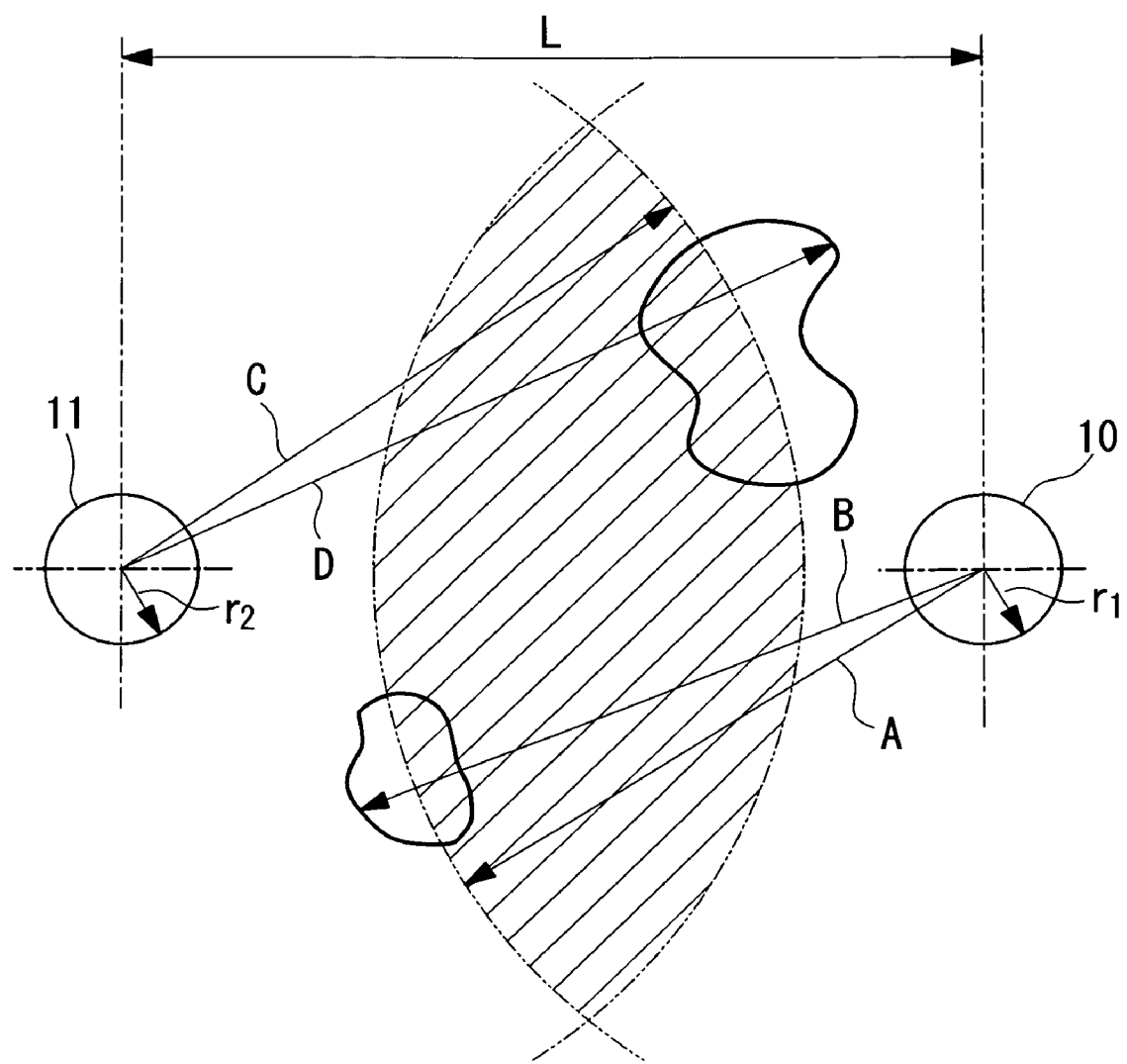
FIG. 11 is a plan view illustrating the area where the optical axis of the camera of the microscope examination apparatus shown in FIG. 1 is disposed.

According to this embodiment, the optical axis C of the camera 6 is disposed within the above-identified range but not on the plane intersecting with the axes of the two support stands 10 and 11. As shown in FIG. 10, the optical axis C of the camera 6 is disposed at a position away from the plane. The turret 13 is rotated around the axis of the first support stand 10 so that one of the selected objective lens units 4a to 4d is disposed at a position aligned with the optical axis C of the camera 6, whereas the first arms 14 are rotated around the axis of the second support stand 11 so that one of the image-forming lens units 5a and 5b aligned with the selected objective lens units 4a to 4d is disposed at a position aligned with the optical axis C of the camera 6.

If the objective lens unit 4d and the image-forming lens unit 5b, having a high magnifying power, are selected, the second arm 17 is rotated around the axis of the second support stand 11 so that the zooming mechanism 15 is disposed at a position aligned with the optical axis C of the camera 6. At this time, the objective lens unit 4d, the image-forming lens unit 5b, and the zooming mechanism 15 can be rotated without interfering with the support stands 10 and 11. Also, the distance L between the support stands 10 and 11 can be reduced without reducing the size of the turret 13 and the arms 14 and 17.

Figure 12A:
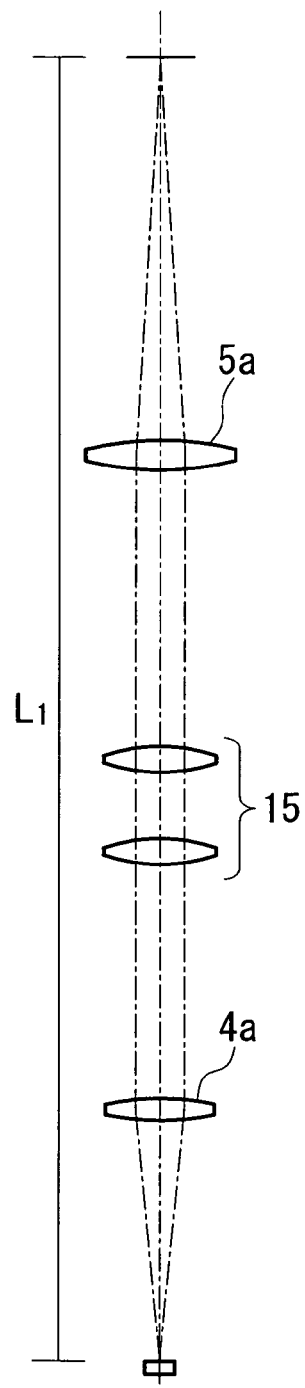
FIGS. 12A to 12C are schematic diagrams showing an optical-path bypass unit of the microscope examination apparatus shown in FIG. 1.
Figure 12B:
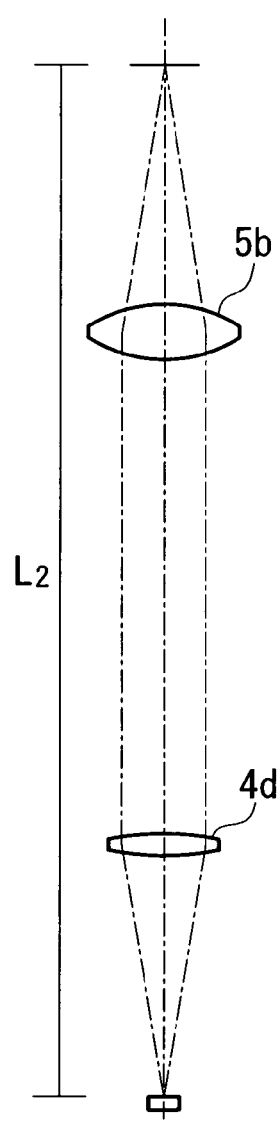

In general, it is preferable to dispose the objective lenses 4a to 4d and the image-forming lens units 5a and 5b in a positional relationship such that the rear focal lengths substantially match. In the microscope examination apparatus 1 according to this embodiment, when such a positional relationship is achieved, distances L1 and L2 from the image location of one of the objective lens units 4a to 4d to the image location of one of the image-forming lens units 5a and 5b differ between a case in which the objective lens unit 4a and the image-forming lens unit 5a are selected, as shown in FIG. 12A, and a case in which the objective lens unit 4d and the image-forming lens unit 5b are selected, as shown in FIG. 12B.

Figure 12C:
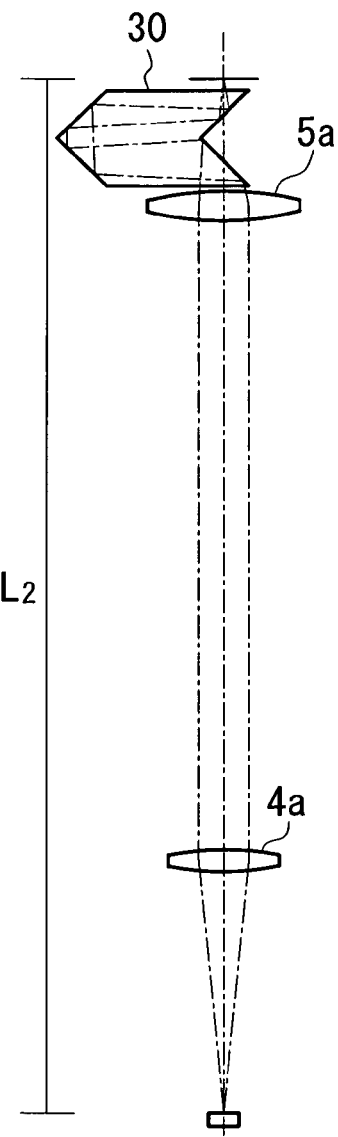

Therefore, as shown in FIG. 12C, in the microscope examination apparatus 1 according to this embodiment, the image-forming lens unit 5a having high magnifying power and whose distance L1 between the image locations is great includes a prism (optical-path bypass unit) 30 for matching the linear distance L2 between the image locations to a distance L2 of the low magnifying power by bending and diverting the optical path. In this way, clear images can be captured from low magnifying power to high magnifying power without moving the camera 6 fixed on the upper plate 12.

By providing a rotational mechanism for rotating the prism 30 around a horizontal axis, such as a motor or an adjustment knob, the tilt of the optical axis due to individual variability, such as manufacturing errors of the prism 30, may be corrected.

Figure 13:
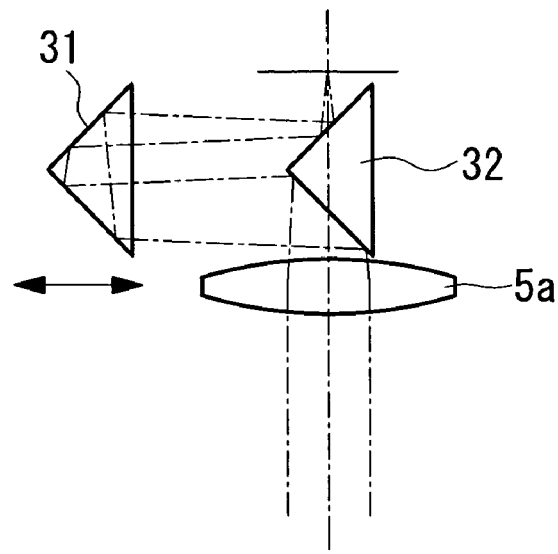
FIG. 13 illustrates a modification of the optical-path bypass unit shown in FIG. 12.
Figure 14:
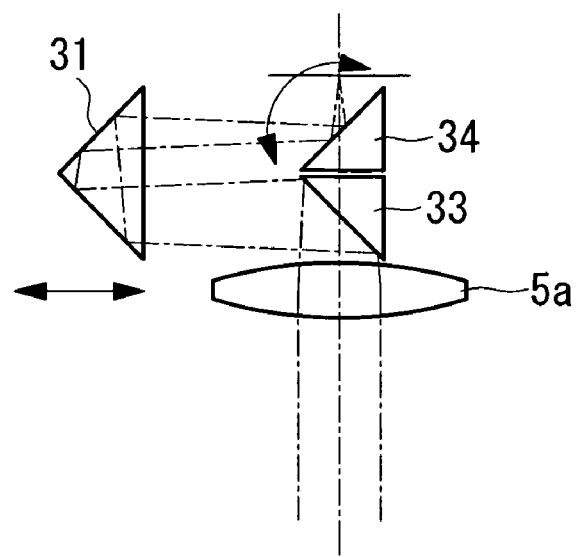
FIG. 14 illustrates another modification of the optical-path bypass unit shown in FIG. 12.

As shown in FIG. 13, a combination of two or more prisms 31 and 32 may be used as an optical-path bypass unit, and the variation in the optical path length due to the individual variability of the prisms 31 and 32 may be corrected by providing an adjustment mechanism (not shown in the drawing) configured to adjust the distance between the prisms 31 and 32 in the directions indicated by the arrow. As shown in FIG. 14, three prisms 31, 33, and 34 may be used as a optical-path bypass unit, and the above-described tilt of the optical axis C may be corrected by providing a rotational mechanism (not shown in the drawing) configured to rotate the rearmost prism 34 for deflecting the diverted optical path so that the optical path is restored to a vertical optical path toward the camera 6. In this way, only the tilt of the rearmost optical path toward the camera 6 can be adjusted. Therefore, accurate correction can be easily carried out without changing the optical path in a complicated manner.

In the microscope examination apparatus 1 according to this embodiment, an objective parfocal mechanism 35 and an image parfocal mechanism 36 are provided for the objective lens units 4a to 4d and the image-forming lens units 5a and 5b to adjust the focal points of these lens units.

Figure 3:
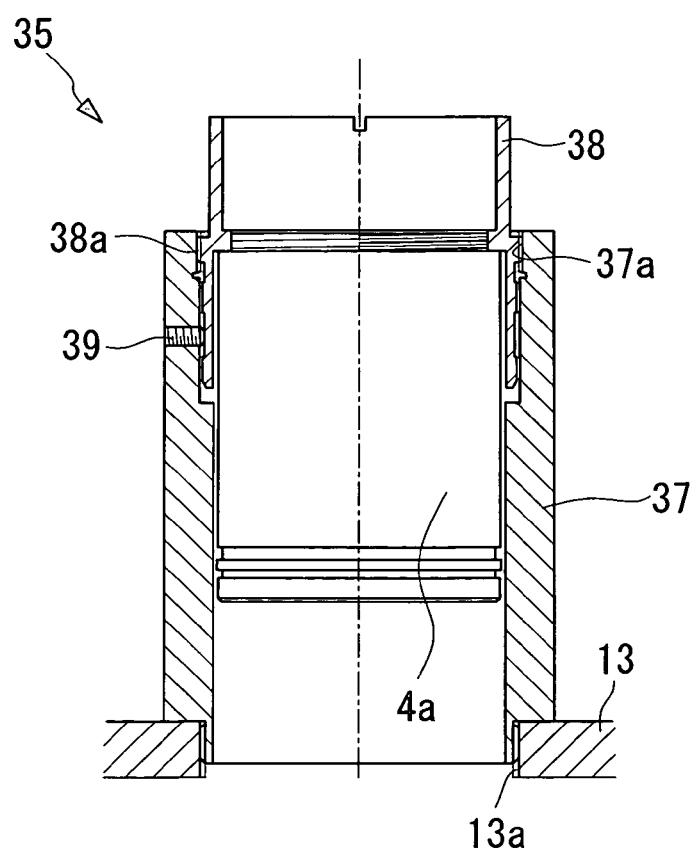
FIG. 3 is a longitudinal cross-sectional view illustrating a low-magnification objective lens unit of the microscope examination apparatus illustrated in FIG. 1.
Figure 4:
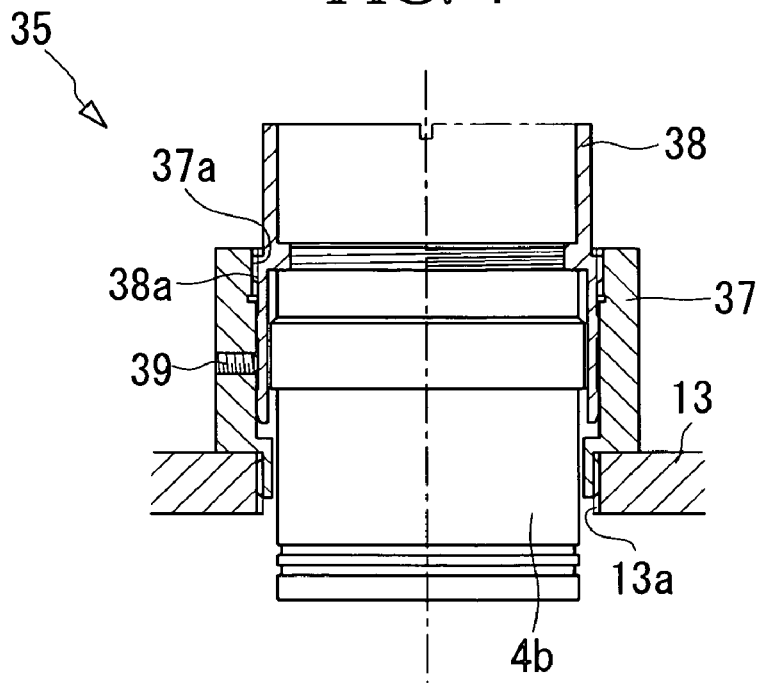
FIG. 4 is a longitudinal cross-sectional view illustrating another low-magnification objective lens unit similar to that illustrated in FIG. 3.
Figure 5:
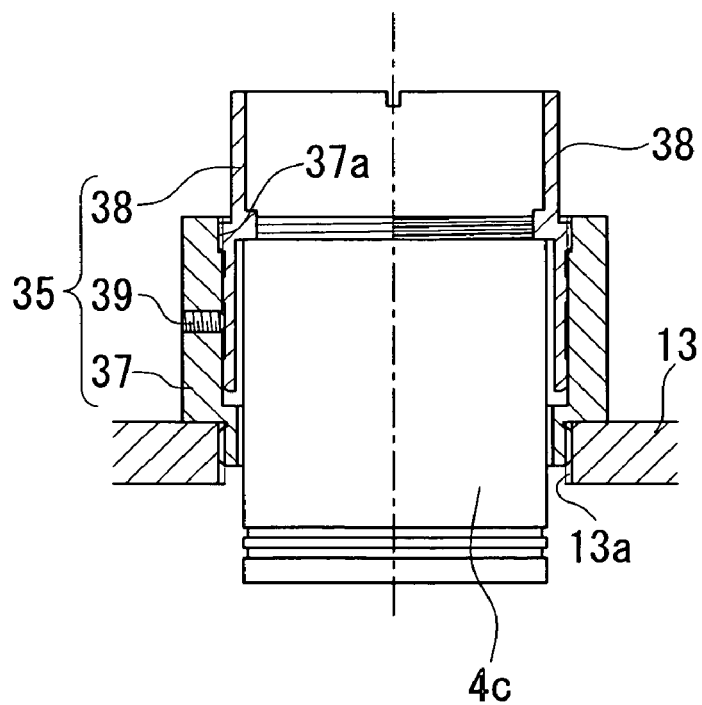
FIG. 5 is a longitudinal cross-sectional view illustrating another low-magnification objective lens unit similar to that illustrated in FIG. 3.

In case of the objective lens units 4a to 4d illustrated in FIGS. 3 to 5, the objective parfocal mechanism 35 includes a fixed bracket 37 engaged with a screw hole 13a provided on the turret 13 and having a female screw 37a; a movable bracket 38 fixed to the objective lens units 4a to 4c and having a male screw 38a engaged with the female screw 37a; and a locking screw 39 for fixing the relative displacement of the brackets 37 and 38.

Figure 6:
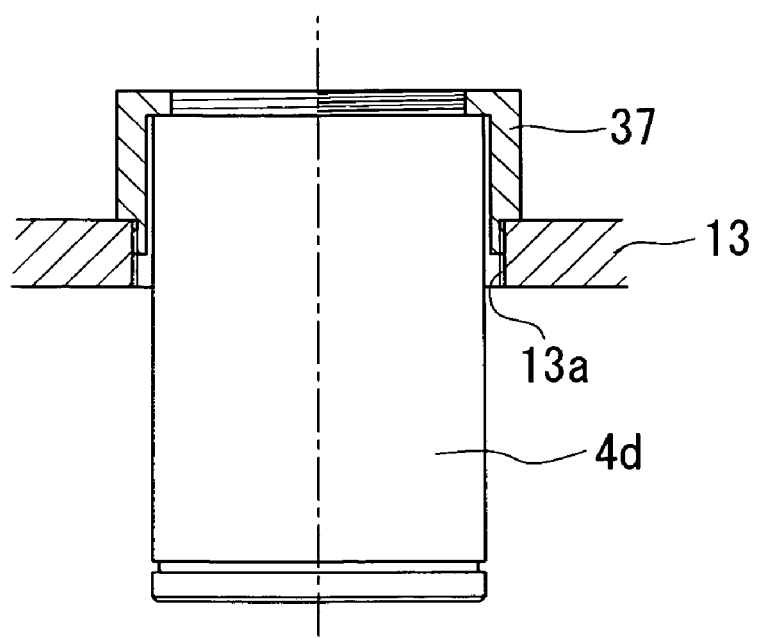
FIG. 6 is a longitudinal cross-sectional view illustrating a high-magnification objective lens unit of the microscope examination apparatus illustrated in FIG. 1.

The objective lens unit 4d for high magnification illustrated in FIG. 6 does not include the objective parfocal mechanism 35. According to this embodiment, the combination of the objective lens unit 4d and the image-forming lens unit 5b is only one combination for high magnification. Therefore, the objective lens does not have to be changed. However, an objective parfocal mechanism may be provided for the objective lens unit 4d. If a plurality of objective lens units is used as the high-magnification objective lens unit 4d, it is preferable to provide the objective parfocal mechanism 35 similar to that used for low magnification.

Figure 15:
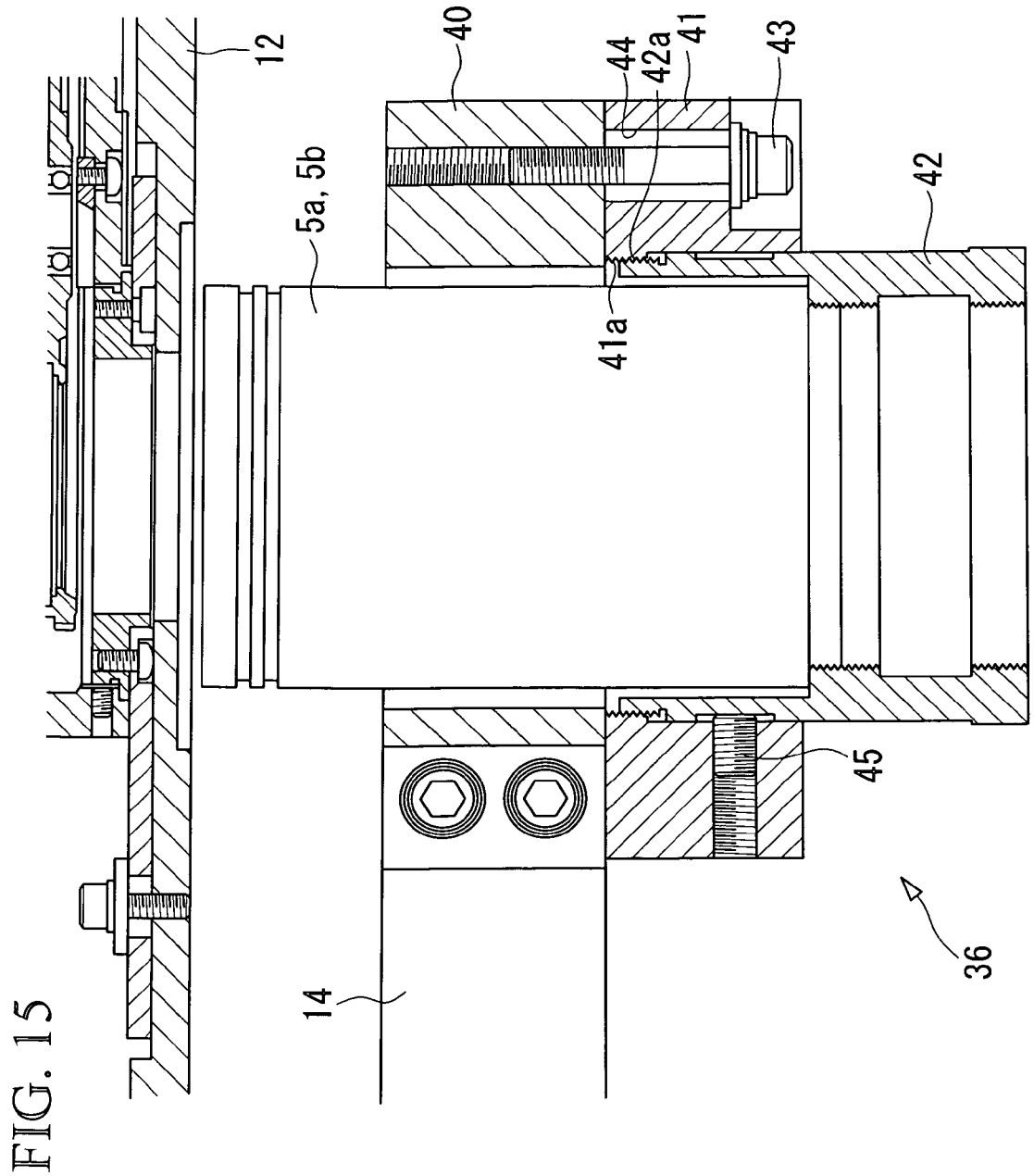
FIG. 15 is a longitudinal cross-sectional view with a partially cutaway section illustrating the attachment structure of an image-forming lens unit of the microscope examination apparatus shown in FIG. 1.

As shown in FIG. 15, the image parfocal mechanism 36 includes a fixed holder 40 fixed to the first arms 14, a horizontally adjustable holder 41 mounted in such a manner as to be capable of moving the horizontal direction with respect to the fixed holder 40, and a vertically adjustable holder 42 mounted in such a manner as to be capable of moving in the vertical direction with respect to the horizontally adjustable holder 41 and used to fix the image-forming lens units 5a and 5b. The horizontally adjustable holder 41 is attached to the lower surface of the fixed holder 40. By loosening a fixing screw 43, the image-forming lens units 5a and 5b are moved horizontally for a distance corresponding to the gap between a hole 44 formed in the horizontally adjustable holder 41 and the fixing screw 43. By tightening the fixing screw 43, the image-forming lens units 5a and 5b are positioned at the adjusted horizontal positions. The vertically adjustable holder 42 includes a male screw 42a that engages with a female screw 41a provided on the horizontally adjustable holder 41. By turning the male screw 42a with respect to the female screw 41a, the image-forming lens units 5a and 5b are moved in the vertical direction. By fixing a locking screw 45, the image-forming lens units 5a and 5b are fixed at the adjusted vertical positions.

The illumination device 16 is connected to the external light source 2 via an optical fiber 46. A dichroic mirror 47 is provided on the upper end of the zooming mechanism 15. The dichroic mirror 47 is configured to reflect the light emitted from the illumination device 16 in a vertically downward direction through the zooming mechanism 15 and the objective lens unit 4d so as to irradiate the specimen A with the light. A switch 48 and a second illumination device 50 for illuminating the entire specimen A through the optical fiber 49 are provided on the light source 2 near the stage 3. The switch 48 may be any type of device, such as a galvanometer or a shutter. When the objective lens unit 4a having a low magnifying power and the image-forming lens unit 5a are selected, light is directed to the second illumination device 50 by the switch 48 so as to irradiate the entire specimen A with the light.

The operation of the microscope examination apparatus 1 according to this embodiment, having the above-described structure, will be described below.

First, to examine the specimen A, such as a small laboratory animal, using the microscope examination apparatus 1 according to this embodiment, the specimen A is fixed to the tray member 9 outside the microscope examination apparatus 1. Then, the tray member 9 to which the specimen A is fixed is positioned by engaging the tray member 9 with the through hole 3a formed in the stage 3. In such a case, the positioning of the tray member 9 can be easily carried out because sufficient space is provided between the first base 7a and the second base 7b. Moreover, the observer can examine the specimen A by freely changing the examination site on the specimen A because a sufficient operating range of the specimen A is provided, based on the operation of the stage 3.

Next, when the specimen A positioned as described above is examined at a low magnification, the turret 13 attached to the first support stand 10 is rotated so that the objective lens unit 4a having low magnifying power is moved to a position aligned with the optical axis C of the camera 6. When carrying out low-magnification examination, the zooming mechanism 15 is not used. Therefore, as shown in FIG. 3, the objective lens unit 4a that projects upwards from the turret 13 by a large amount can be used. Accordingly, the numerical aperture of the objective lens can be prevented from being excessively reduced.

The image-forming lens unit 5a is moved to a position aligned with the optical axis C of the camera 6 by rotating the first arms 14 attached to the second support stand 11. In this way, the combination of the objective lens unit 4a and the image-forming lens unit 5a, suitable for low-magnification examination, is selected.

Then, the switch 48 is switched to the second illumination device 50 so that the entire specimen A is irradiated with the light emitted from the light source 2 and the return light from the specimen A is focused at the camera 6 through the objective lens unit 4a and the image-forming lens unit 5a to form an image. In this case, since the prism 30, functioning as a optical-path bypass unit, is disposed on the image-forming lens unit 5a, the light transmitted through the image-forming lens unit 5a is focused at the camera 6 attached to the upper plate 12 to form an image.

To increase the magnification for examining the specimen A, the turret 13 is turned to select one of the other objective lens units 4b to 4d. In this case, since three types of objective lens units 4a to 4c having low magnifying powers are provided for the microscope examination apparatus 1 according to this embodiment, the magnifying power can be changed by changing only the objective lens units 4b and 4c, without changing the image-forming lens unit 5a. When the objective lens units 4a to 4d are changed in this way, the position of the objective lens that is conjugate with the image location of the image-forming lens may change due to the individual variability of the lens units 4a to 4d and 5a. However, according to this embodiment, by finely adjusting the objective parfocal mechanism 35 and the image parfocal mechanism 36, precise adjustment is possible. Therefore, a precisely focused, clear image may be obtained at any magnification.

To examine the specimen A with high magnification, first, the turret 13 is turned to move the high-magnification objective lens unit 4d to a position aligned with the optical axis C of the camera 6. In this way, the objective lens units 4a to 4c having low magnifying powers and protruding upwards from the turret 13 are removed from the position aligned with the optical axis C of the camera 6. Next, the second arm 17 is turned to insert the zooming mechanism 15 into the space formed on the optical axis C of the camera 6 above the high-magnification objective lens unit 4d by removing the objective lens units 4a to 4c having low magnifying powers. By turning the first arms 14, the high-magnification image-forming lens unit 5b can be disposed at a position aligned with the optical axis C of the camera 6.

In this way, the combination of the objective lens unit 4d, the zooming mechanism 15, and the image-forming lens unit 5b, suitable for high-magnification examination, is configured.

To examine the specimen A using the high-magnification lens units 4d, 5b, and 15 configured as described above, the examination site of the specimen A disposed on the stage 3 is aligned with the optical axis C of the camera 6 by operating the stage 3, in the same way as described above. Next, light emitted from the light source 2 by operating the switch 48 is transmitted toward the first illumination device 16 and is deflected at the dichroic mirror 47 provided at the upper end of the zooming mechanism 15 toward the specimen A. The return light generated at the specimen A irradiated with light transmitted through the zooming mechanism 15 and the objective lens unit 4d is focused by the objective lens unit 4d, and the image of the specimen A is enlarged by the zooming mechanism 15, is transmitted through the dichroic mirror 47, and is imaged at the camera 6 by the image-forming lens unit 5b. The observer operates the zooming mechanism 15, when necessary, to set a specific magnifying power for examination. At this time, light can be transmitted through pre-selected absorption filters 24 so that only light having a specific wavelength is captured by the camera 6.

In this way, with the microscope examination apparatus 1 according to this embodiment, by turning the turret 13, the objective lens units 4a to 4d can be easily switched, and by turning the first arms 14, the image-forming lens units 5a and 5b suitable for the objective lens units 4a to 4d can be selectively switched. In this way, the magnifying power can be changed by not only the objective lens units 4a to 4d, but also the image-forming lens units 5a and 5b. Moreover, the numerical aperture will not be excessively reduced when the magnifying power is low.

In such a case, since the combination of the objective lens units 4a to 4d and the image-forming lens units 5a and 5b are changed, the lens units may be out of focus due to individual variability. However, according to this embodiment, since the parfocal adjustment mechanisms 35 and 36 are provided for the objective lens units 4a to 4d and the image-forming lens units 5a and 5b, respectively, when the objective lenses and the image-forming lenses are rotated, the positions of the objective lenses and the image-forming lenses can be easily corrected so that the examined image is not out of focus.

Since the image-forming lens unit 5a has a long focal length or, in other words, since the optical-path bypass unit 30 is provided for the image-forming lens unit 5a, clear images can be captured from low magnifying power to high magnifying power, and the linear distance from the specimen A to the camera 6 can be reduced without changing the position of the camera 6. Since parfocal adjustment is carried out at the optical-path bypass unit 30, an advantage is provided in that adjustment can be carried out easily without moving the image-forming lens unit 5b.

Since the zooming mechanism 15 that can be interposed between the objective lens unit 4d on the high-magnification side and the image-forming lens unit 5b, examination can be carried out while continuously changing the magnifying power. When the objective lens units 4a to 4c having low magnifying powers and the image-forming lens unit 5a are selected, the zooming mechanism 15 can be removed from the optical axis C of the camera 6, and the examination image can be made brighter while carrying out low-magnification examination with a small numerical aperture.

In such a case, the size of the zooming mechanism 15 can be reduced by reducing the size of the lens of the zooming mechanism 15.

In the microscope examination apparatus 1 according to this embodiment, since the zooming mechanism 15 and the objective lens units 4a to 4d are provided so as to be capable of individually rotating around the two support stands 10 and 11 provided on the second base 7b, the objective lens units 4a to 4c having low magnifying powers and the zooming mechanism 15 can be disposed at overlapping positions in the vertical direction since these are not used simultaneously. As a result, this is advantageous since the length in the vertical direction can be reduced. In such a case, by disposing the optical axis C of the camera 6 at a position away from the plane intersecting with the axes of the two support stands 10 and 11, the two support stands 10 and 11 can be brought close together to reduce the length in the width direction.

The number of support stands 10 and 11 is not limited to two; three or more support stands may be provided.

Since the objective lens units 4a to 4c having low magnifying powers and the zooming mechanism 15 are disposed at overlapping positions in the vertical direction, the objective lens units 4a to 4c and the zooming mechanism 15 may interfere with each other when switching the lens units. However, by mechanically or electrically coupling the insertion and removal of the zooming mechanism 15 and the insertion and removal of the objective lens units 4a to 4c, such a problem can be avoided. When the objective lens unit 4d having a high magnifying power and the zooming mechanism 15 correspond to each other one-to-one, such as in the case of the microscope examination apparatus 1 according to this embodiment, the zooming mechanism 15 may be fixed to the upper portion of the objective lens unit 4d having a high magnifying power.

The microscope examination apparatus 1 according to this embodiment uses a structure in which the components, such as the turret 13, the first arms 14, the second arm 17, and the bracket 18 for the first illumination device, that are attached in such a manner that they are rotatable around the axes of the support stands 10 and 11 are assembled outside the microscope examination apparatus 1 as the assembly 21 and are stacked on the upper end of the support stands 10 and 11. Therefore, the microscope examination apparatus 1 is advantageous in that assembling is easy, and addition of other lens units and modifications are easy.

In the microscope examination apparatus 1 according to this embodiment, the base 7 is a two-stage structure wherein the stage 3 is provided on the lower first base 7a and the support stands 10 and 11 are attached to the upper second base 7b. Therefore, the spacing members 8 between the two bases 7a and 7b can be disposed great distances apart from each other, regardless of the distance between the support stands 10 and 11. As a result, a large space can be provided around the stage 3, thus improving the case of manipulation of the specimen A, and decreasing the length in the width direction by decreasing the distance between the support stands 10 and 11.

Since the spacing members 8 are replaceable, the height of the second base 7b with respect to the first base 7a can be set to any height. Therefore, the distance can be set in accordance with the size of the specimen A placed on the stage 3.

Since the specimen A is not fixed directly onto the stage 3, but is fixed to the tray member 9, which is in turn fixed to the stage 3, the specimen A can be handled even more easily. Since the tray member 9 is composed of a transparent or black material, light that misses the specimen A and is incident on the tray member 9 is prevented from entering the objective lens units 4a to 4d as stray light.

In the microscope examination apparatus 1 according to this embodiment, since the camera 6 is disposed on the upper plate 12 supported by the two support stands 10 and 11, the camera 6 is less likely to be vibrated. Thus, blurriness of the examination image can be prevented. Since the camera 6 is detachable, the camera 6 can be selected in accordance with the type of the specimen A to be examined and the examination method to be employed. By providing the camera 6 in a manner such that it can rotate around the optical axis C, the angle of the camera 6 can be set in accordance with the orientation of the specimen A.

If examination is carried out with the entire microscope examination apparatus 1 according to this embodiment disposed inside a blackout curtain or a dark box, external light can be prevented from entering the objective lens units 4a and 4b. In particular, for fluoroscopy, it is preferable to carry out examination with the microscope examination apparatus 1 disposed inside a blackout curtain or a dark box because the fluorescence is faint. Examination can be carried out easily inside a blackout curtain or a dark box if the turret 13, the first arms 14, the second arm 17, and the camera 6 can be remotely controlled by a specific driving unit. Furthermore, part of the blackout curtain may be folded up or a window that can be opened and closed may be provided on part of the dark box for manual operation.

Second Embodiment

Next, a microscope examination apparatus 60 according to a second embodiment of the present invention will be described with reference to FIG. 16. The description of this embodiment is simplified by representing the components that are the same as those in the microscope examination apparatus 1 according to the above-described first embodiment by the same reference numerals as those according to the first embodiment.

Figure 16:
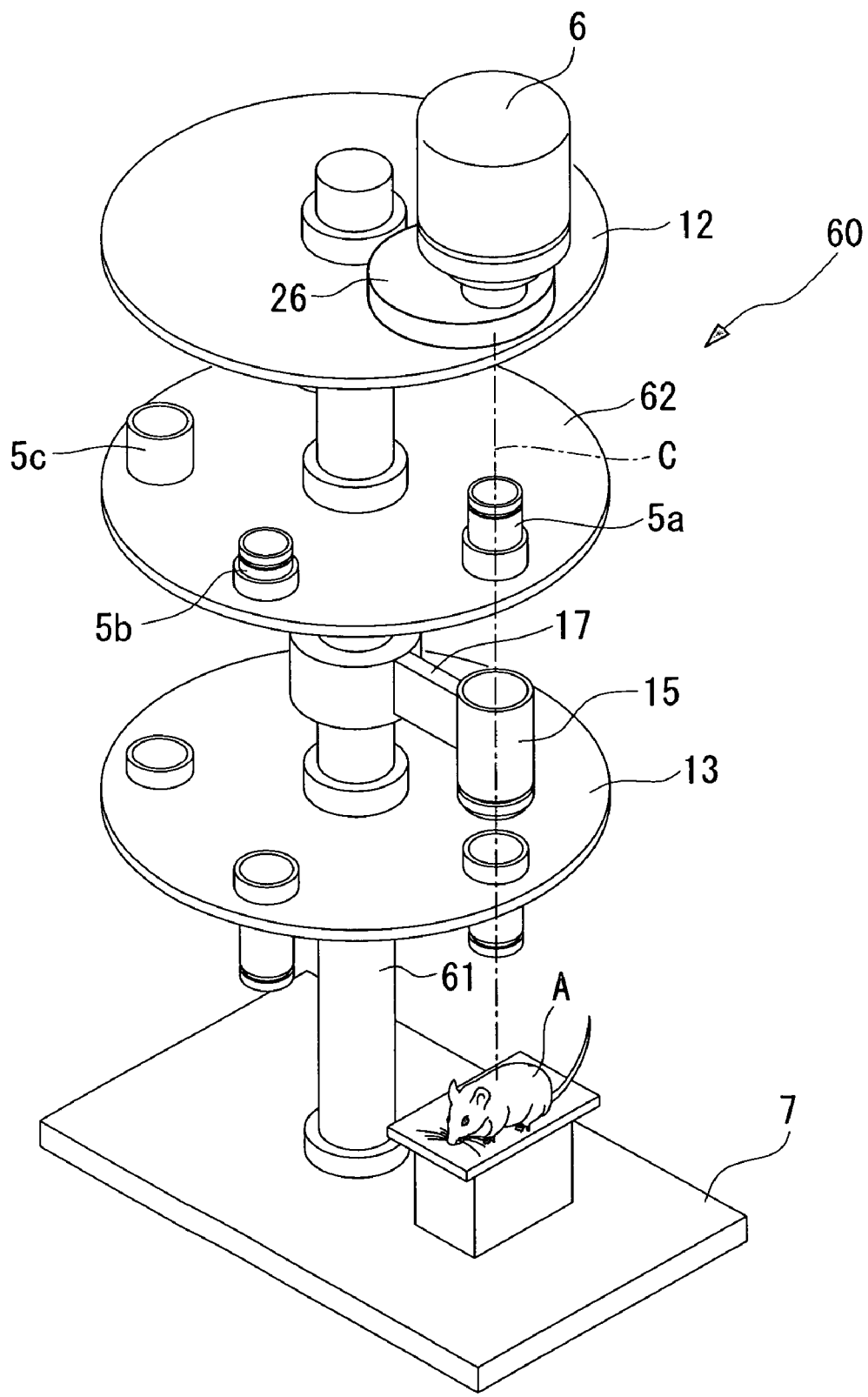
FIG. 16 is a perspective view illustrating a microscope examination apparatus according to a second embodiment of the present invention.

The microscope examination apparatus 60 according to this embodiment differs from the microscope examination apparatus 1 according to the first embodiment in that, as illustrated in FIG. 16, a turret 13, an arm 17, and a second turret 62 are attached to a single support stand 61 in a manner such that they are rotatable around the support stand 61.

More specifically, as illustrated in FIG. 16, the microscope examination apparatus 60 according to this embodiment includes a base 7 to which a stage 3 for holding a specimen A is fixed and the support stand 61 vertically extending from the base 7. The turret 13 holding a plurality of objective lens units 4a to 4d, the arm 17 holding a zooming mechanism 15, and the second turret 62 holding a plurality of image-forming lens units 5a to 5c are attached to the middle area of the support stand 61 in this order from the bottom in such a manner that they are capable of individually rotating around the vertical axis of the support stand 61. An upper plate 12 is fixed to the upper end of the support stand 61. A camera 6 whose optical axis C faces vertically downward is fixed to the upper plate 12. The light source is not shown.

When examining the specimen A placed on the stage 3, the objective lens units 4a to 4d and the image-forming lens units 5a to 5c are selected in accordance with the magnifying power to be used for examination. One of the selected objective lens units 4a to 4d and one of the selected image-forming lens units 5a to 5c are disposed at positions aligned with the optical axis C of the camera 6. When carrying out high-magnification examination, the zooming mechanism 15 is also disposed at a position aligned with the optical axis C of the camera 6. With this embodiment, similar to the first embodiment, one of the image-forming lens units 5a to 5c can be selected in accordance with the objective lenses 4a to 4d having different magnifying powers.

The structure of the microscope examination apparatus 60 according to this embodiment is simpler than that of the microscope examination apparatus 1 according to the first embodiment. Since the entire optical system is attached to the single support stand 61, an advantage is provided in that the size of the microscope examination apparatus 60 in the width direction can be reduced. Moreover, since the stage 3, which is attached to the base 7, is disposed in a relatively large space not surrounded by other components, the microscope examination apparatus 60 can be easily operated.

Third Embodiment

Next, a microscope examination apparatus 70 according to a third embodiment will be described with reference to FIG. 17.

Also in this embodiment, components that are the same as those of the microscope examination apparatuses 1 and 60 according to the above-described embodiments will be represented by the same reference numerals to simplify the description.

The microscope examination apparatus 70 according to this embodiment is similar to the microscope examination apparatus 60 according to the second embodiment in that it includes a single support stand 61 fixed to a base 7.

Figure 17:
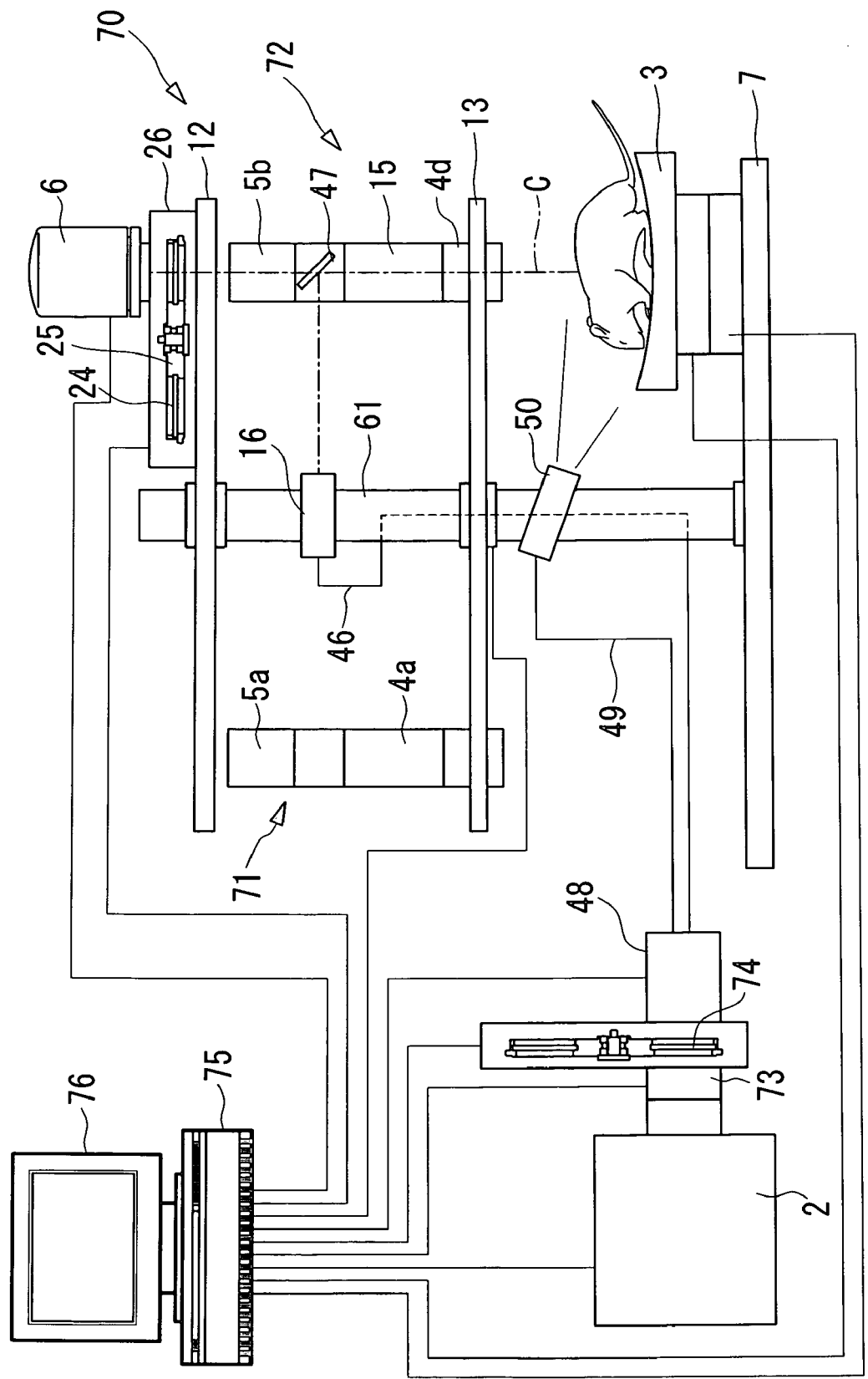
FIG. 17 illustrates the overall structure of a microscope examination apparatus according to a third embodiment of the present invention.
Figure 18:
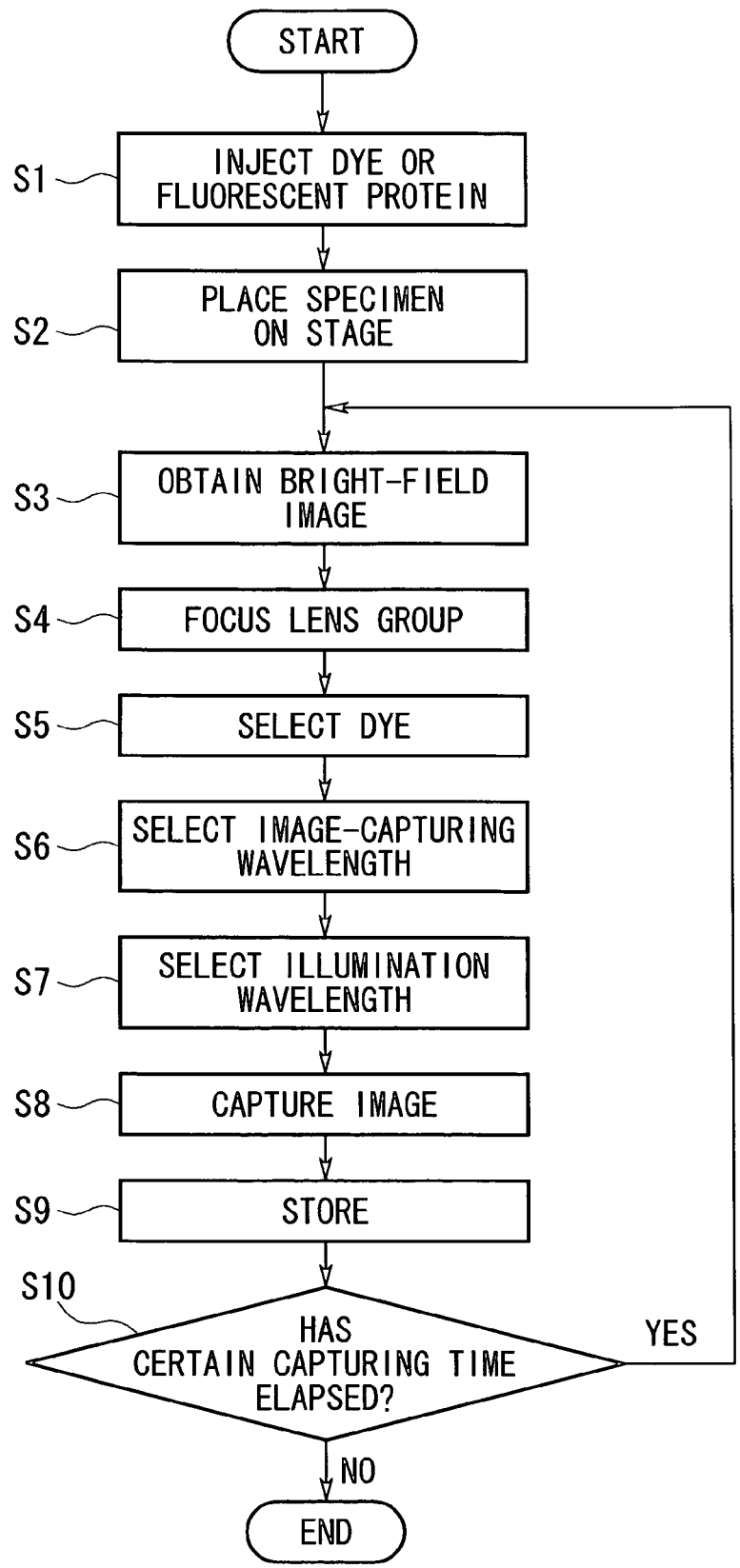
FIG. 18 is a flow chart illustrating an examination process of the microscope examination apparatus shown in FIG. 17.

As shown in FIG. 17, the microscope examination apparatus 70 includes a first lens group 71 that is a combination of an objective lens unit 4a and an image-forming lens unit 5a, and a second lens group 72 that is a combination of an objective lens unit 4d having a high magnifying power, a zooming mechanism 15, and an image-forming lens unit 5b. In the drawing, only one first lens group 71 and one second lens group 72 are illustrated. However, a plurality of first lens groups 71 having different magnifying powers may be provided. The lens groups 71 and 72 are fixed to a turret 13 that is rotatably supported by a support stand 61. The lens groups 71 and 72 are disposed at equal radial distances and specific distances apart from each other in the circumferential direction.

The microscope examination apparatus 70 is a fluoroscopy apparatus and includes a light source 2, a shutter 73, a filter turret 74, and a switch 48 on the side of the light source 2. First and second illumination devices 16 and 50 are connected to the switch 48. For high-magnification examination, a dichroic mirror 47 for epi-illumination of a specimen A is interposed between the zooming mechanism 15 and the image-forming lens unit 5b.

In the drawing, reference numeral 75 represents a computer including a light source; a control device for controlling the shutter 73; filter turrets 25 and 74; and the switch 48; a stage 3; the turret 13; and a camera 6. Reference numeral 76 represents a monitor.

A case in which fluoroscopy is carried out on the specimen A using the microscope examination apparatus 70 according to this embodiment, having the above-described structure, will be described below.

First, a dye is injected in the specimen A, such as a small laboratory animal, a fluorescent protein is injected into the specimen A, or a fluorescent protein is expressed in the specimen A (Step S1). The prepared specimen A is placed on the stage 3 (Step S2).

Next, a specific magnifying power is selected, and the lens groups 71 and 72 corresponding to the magnifying power are aligned with the optical axis C of the camera 6. If the magnifying power is low, the entire specimen A is irradiated with light by the second illumination device 50 to obtain a bright field image (Step S3). In this state, the specimen A is moved to a position corresponding to a specific examination site by operating the stage 3, and the lens groups 71 and 72 are adjusted to focus on the specimen A (Step S4).

Next, the dye to be examined by fluoroscopy is selected (Step S5), and the imaging wavelength corresponding to the dye is determined by the filter turret 25 (Step S6). The illumination wavelength (excitation wavelength) corresponding to the selected dye is set by the filter turret 74 (Step S7). The exposure is determined, an image is captured (Step S8), and the image is stored (Step S9). When examination is to be carried out over a specific amount of time, the image-capturing operation is repeated at intervals (Step S10).

Since the microscope examination apparatus 70 according to this embodiment includes the lens groups 71 and 72 having the objective lens units 4a and 4d and the image-forming lens units 5a and 5b or includes the second lens group 72 having the zooming mechanism 15, the magnifying power can be changed without carrying out parfocal adjustment, and the numerical aperture can be prevented from becoming excessively small even at low magnification. As a result, a bright image can be captured even at low magnification.

Many autofluorescence beams, in addition to the fluorescence from the target fluorescent substance, are generated at the specimen A, such as a small laboratory animal. Therefore, a computer 24 may include a spectral deconvolution processing unit for separating and removing fluorescence other than that generated at the target fluorescent substance from the obtained fluorescence image by analyzing the fluorescence spectra generated at substances, such as fluorescent dye, and determining the ratio of the amounts of fluorescence obtained at two different wavelengths.

More specifically, for example, as described in U.S. Pat. No. 6,403,332, if the fluorescence spectrum of the target fluorescent substance and the fluorescence spectrum of a substance that generates autofluorescence are known, the ratio of the fluorescence intensities corresponding to two wavelengths in these spectra can be determined in advance. By determining the ratio in advance, the fluorescence spectrum of the target fluorescent substance can be extracted from the observed fluorescence.

When the autofluorescence substance in the specimen A is unknown or undetermined, as described in Japanese Unexamined Patent Application Publication No. HEI-7-50031, it is preferable to capture a fluorescence image of the specimen A and carry out spectral blind deconvolution for simultaneously computing the fluorescence spectrum of the specimen A and the spatial distribution of the fluorescent substances. According to this method, the fluorescence spectra of the fluorescent substances and the percentage of the fluorescent substances existing in each pixel of the captured fluorescence image can be simultaneously determined to determine the distribution of the fluorescent substances in the specimen A.

Fourth Embodiment

Next, a microscope examination apparatus 80 according to a fourth embodiment of the present invention will be described with reference to FIGS. 19 to 21.

Also in this embodiment, components that are the same as those of the microscope examination apparatus 1 according to the above-described embodiments will be represented by the same reference numerals to simplify the description.

Instead of the switch 48, the optical fiber 49, and the illumination device 50 included in the microscope examination apparatus 1 according to the first embodiment, the microscope examination apparatus 80 according to this embodiment includes a reflecting member 82 which is fixed to a retaining member 81 that is fixed to an image-forming lens unit 5a having a low magnifying power and a relay optical system 84 which is fixed to a retaining member 83 that is fixed to a support stand 11. According to the first embodiment, the zooming mechanism 15 is rotatably supported by the support stand 11, whereas, according to this embodiment, the zooming mechanism 15 is fixed to an objective lens 4c for high-magnification examination.

The reflecting member 82 is disposed in front of and opposite to a first illumination device 16 when an image-forming lens unit 5a for low-magnification is disposed on the optical axis C. In this way, an illumination beam from a light source 2 transmitted through a fiber 46 is emitted from the first illumination device 16 and is deflected at the reflecting member 82 towards the relay optical system 84.

Figure 20:
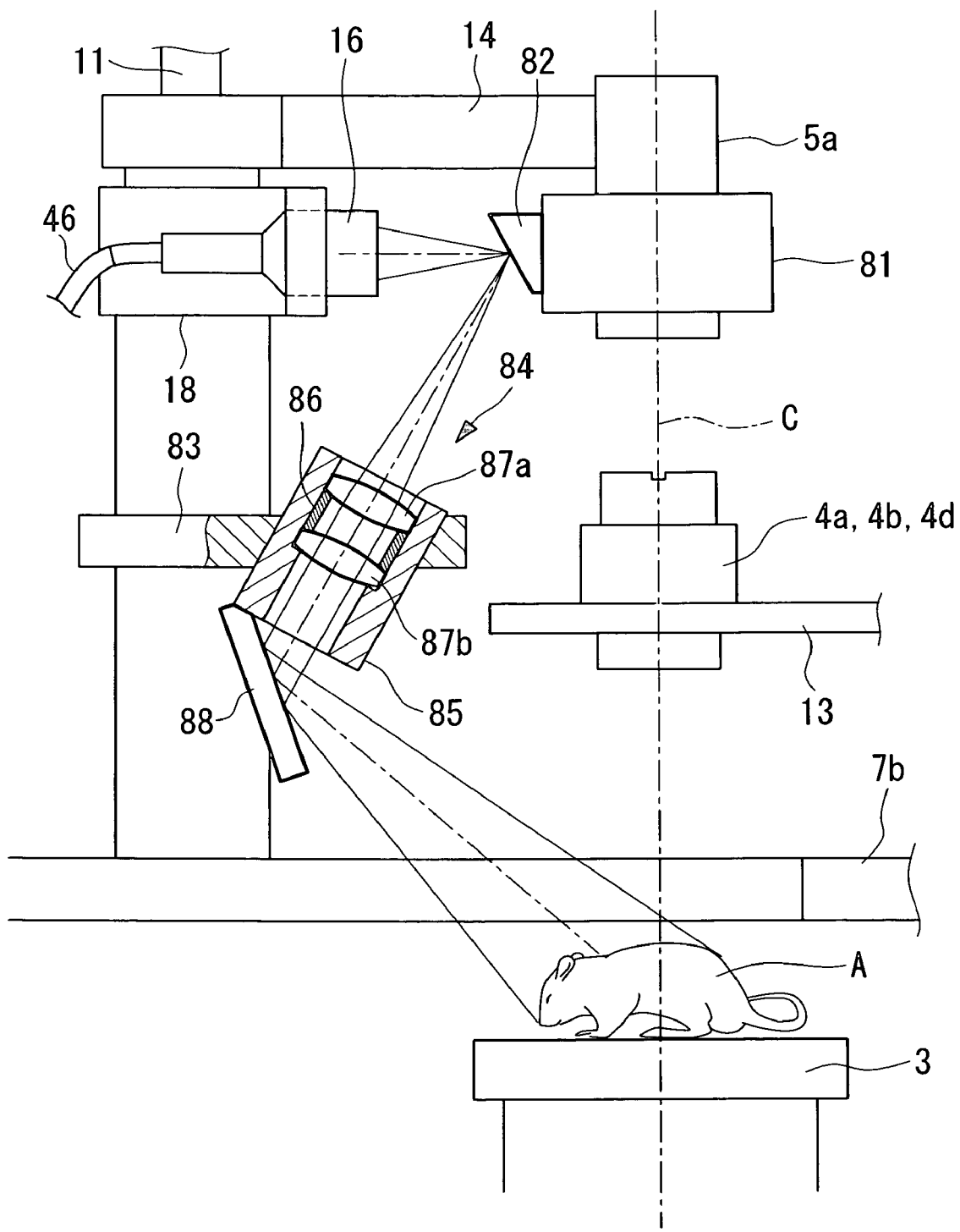
FIG. 20 is a partial longitudinal cross-sectional view illustrating off-axis illumination of the microscope examination apparatus shown in FIG. 19.

FIG. 20 is a cross-sectional view of the relay optical system 84. The relay optical system 84 includes a cylindrical outer barrel 85 disposed outside a turret 13 in the circumferential direction of the turret 13, a plurality of lenses 87a and 87b held by a spacer tube 86 in the outer barrel, and a reflecting member 88 that is disposed on one end of the outer barrel 85 and that deflects the illumination beam relayed through the lenses 87a and 87b toward a specimen A.

Here, the spacer tube 86 adjusts the illumination light beam incident on the specimen A. For example, if the specimen A is a mouse, since the length of the mouse is about 100 mm, the length of the spacer tube 86 is adjusted so that the diameter of the illumination light beam on the stage 3 is 100 mm. The entire specimen A does not necessarily have to be illuminated: in some cases, only the maximum examination region has to be illuminated.

The operation of the microscope examination apparatus 80 according to this embodiment, having the above-described structure, will be described below.

Figure 19:
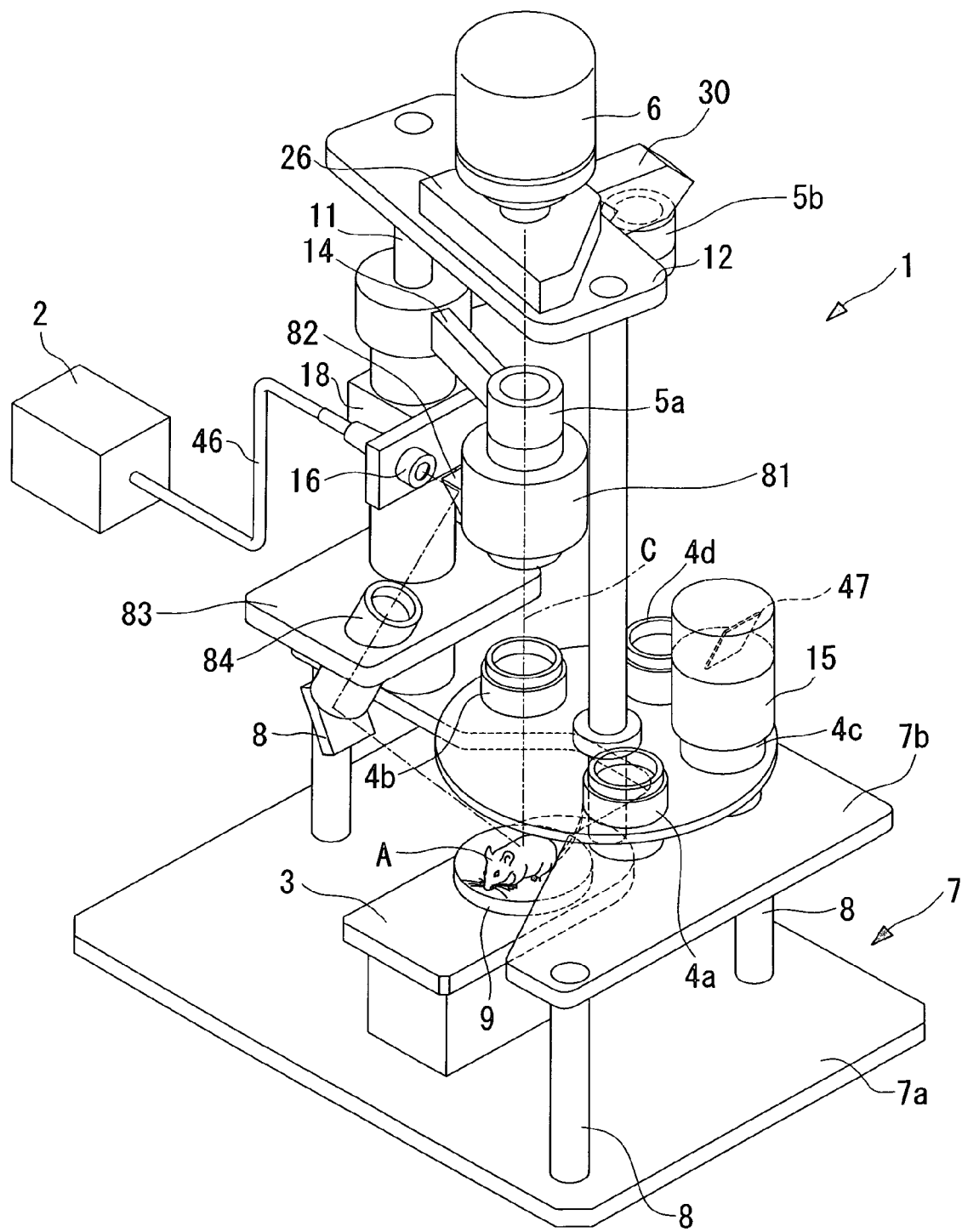
FIG. 19 is a perspective view illustrating a microscope examination apparatus according to a fourth embodiment of the present invention.

As shown in FIGS. 19 and 20, in a low-magnification examination system including the image-forming lens unit 5a for low-magnification examination that is disposed on the optical axis C, the illumination light generated at the light source 2 is guided to the illumination device 16 through the optical fiber 46. Since the reflecting member 82 is disposed in front of and opposing the illumination device 16, the illumination light from the illumination device 16 is deflected at the reflecting member 82 and is directed to the relay optical system 84. Then, the illumination light beam is adjusted at the relay optical system 84, and the illumination light deflected at the reflecting member 88 is made incident on the specimen A.

The return light from the specimen A is focused by one of the objective lenses 4a, 4b, and 4d selectively disposed coaxially with the image-forming lens unit 5a using the turret 13 and is imaged at a camera 6 by the image-forming lens unit 5a.

Figure 21:
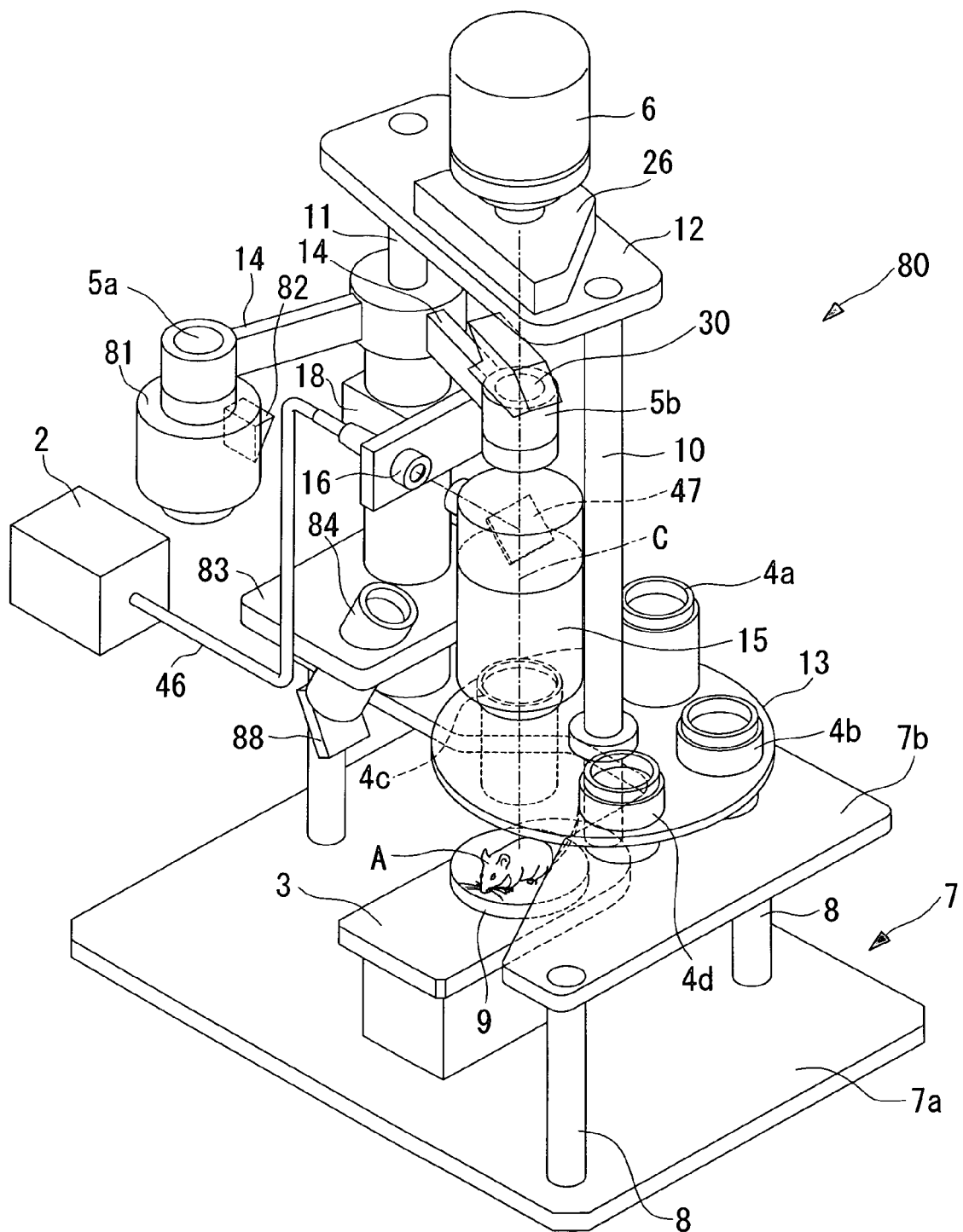
FIG. 21 is a perspective view illustrating the microscope examination apparatus shown in FIG. 19 during high-magnification examination.

As shown in FIG. 21, in a high-magnification examination system including the zooming mechanism 15 and the image-forming lens 5b for high-magnification examination on the optical axis C, an illumination light generated at the light source 2 is transmitted to the illumination device 16 through the fiber 46. By moving the image-forming lens 5a out of the way, the reflecting member 82 is removed from the front of the illumination device 16, and, in its place, a dichroic mirror 47 provided on the upper end of the zooming mechanism 15 is disposed opposite to the illumination device 16. Consequently, the illumination light generated at the illumination device 16 is deflected vertically downwards at the dichroic mirror 47, is focused by the objective lens 4c, and then is incident on the specimen A.

The return light from the specimen A is focused by the objective lens 4c and enlarged by the zooming mechanism 15. Then, the enlarged return light is transmitted through the dichroic mirror 47 and is imaged at the camera 6 by the image-forming lens 5b.

In the microscope examination apparatus 80 according to this embodiment, since the illumination light is not transmitted through the objective lenses 4a, 4b, and 4d during low-magnification examination, autofluorescence generated at the objective lenses 4a, 4b, and 4d can be reduced. As a result, an image having excellent contrast can be obtained. Moreover, since the illumination light beam stopped down at the zooming mechanism 15 during high-magnification examination only has to be incident on the dichroic mirror 47, an advantage is provided in that the size of the dichroic mirror 47 can be reduced.

Fifth Embodiment

Next, a microscope examination apparatus 90 according to a fifth embodiment will be described with reference to FIGS. 22 to 24.

The description of this embodiment is simplified by representing the components that are the same as those in the microscope examination apparatus 80 according to the above-described fourth embodiment with the same reference numerals as those in the fourth embodiment.

Figure 22:
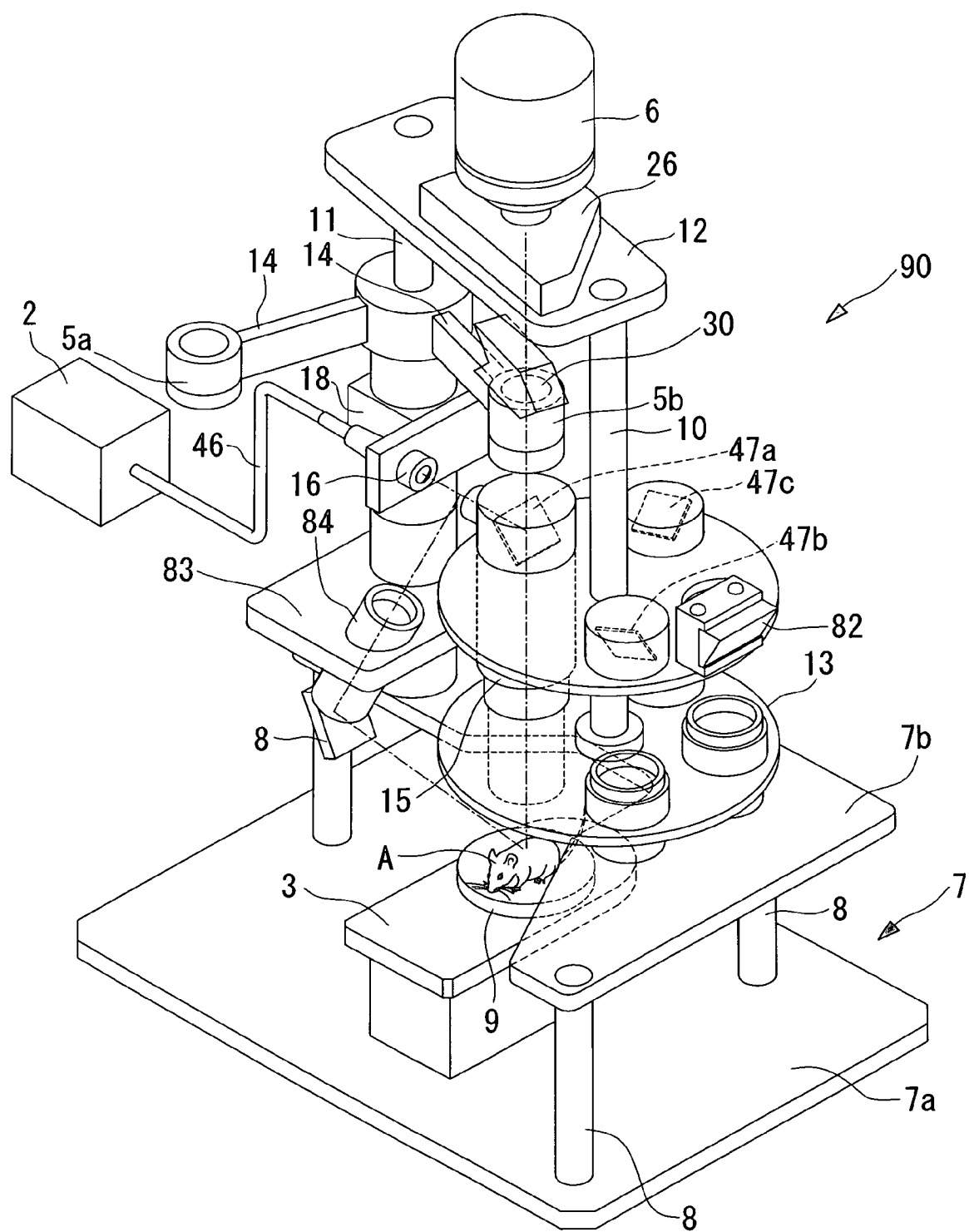
FIG. 22 is a perspective view of a microscope examination apparatus according to a fifth embodiment of the present invention.

Instead of the reflecting member 82 fixed to the image-forming lens unit 5a in the microscope examination apparatus 80 according to the fourth embodiment, the microscope examination apparatus 90 according to this embodiment, as shown in FIG. 22, includes a turret 91 (rotary turret) that is supported in a manner such that it is rotatable around the axis of a support stand 10 and that is interposed between objective lenses 4a to 4d and image-forming lens units 5a and 5b. A plurality of dichroic mirrors 47a, 47b, and 47c having different properties and a reflecting member 82 are fixed to the turret 91.

Figure 23:
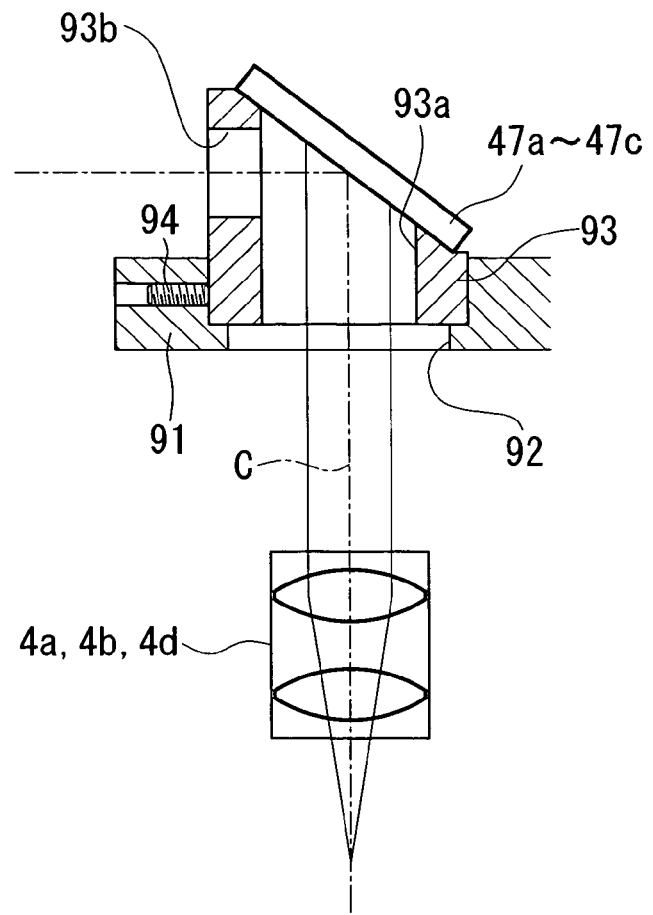
FIG. 23 is a partial longitudinal cross-sectional view illustrating on-axis illumination of the microscope examination apparatus shown in FIG. 22.

As shown in FIG. 23, each of the dichroic mirrors 47a, 47b, and 47c is attached to a holder 93 disposed in a through-hole 92 that vertically penetrates the turret 91. When the central axis of the through-hole 92 holding one of the dichroic mirrors 47a, 47b, and 47c is aligned with the optical axis C, the corresponding dichroic mirror 47a, 47b, or 47c is disposed at a position opposing an illumination device 16.

As shown in FIG. 23, the holder 93 is substantially cylindrical and is engaged with and positioned in the through-hole 92 having a stepped structure provided in the turret 91. The holder 93 is fixed with a setting screw 94 from the outer circumferential surface of the turret 91. Through-holes 93a and 93b penetrating the holder 93 in the axial direction and radial direction, respectively, are formed in the holder 93. One of the dichroic mirrors 47a, 47b, and 47c is fixed on the upper end of the holder 93 at a position covering the through-hole 93a penetrating in the axial direction.

The inner diameters of the through-holes 93a and 93b of the holder 93 and the sizes of the dichroic mirrors 47a, 47b, and 47c are large enough to transmit a light beam focused by the objective lens units 4a to 4d. The dichroic mirrors 47a, 47b, and 47c are each fixed to the holder 93 so that they are disposed at the intersecting point of the illumination light from the illumination device 16 and the optical axis C, at a 45° angle to both the illumination light and the optical axis C.

Figure 24:
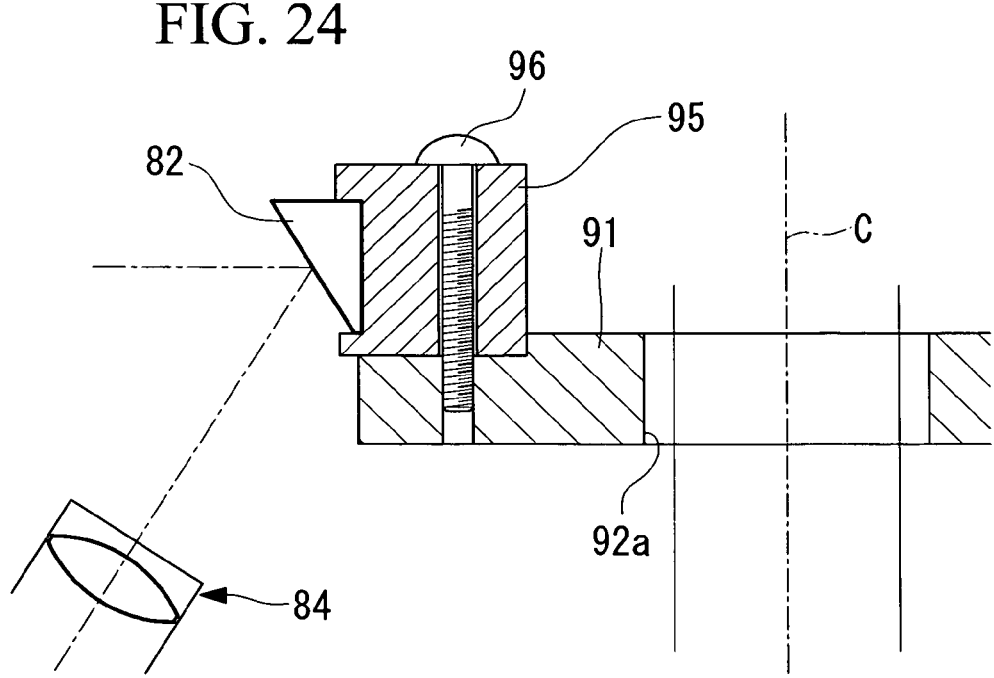
FIG. 24 is a partial longitudinal cross-sectional view illustrating off-axis illumination of the microscope examination apparatus shown in FIG. 22.

As shown in FIG. 24, the reflecting member 82 is attached to a holder 95 with a screw 96 near a through-hole 92a formed in the turret 91. The reflecting member 82 is fixed at a position opposite to the illumination device 16 when the central axis of the through-hole 92a is aligned with the optical axis C.

As shown in FIG. 24, the reflecting member 82 is bonded to the holder 95 fixed at the edge of the turret 91 and is set at a specific angle so that the illumination light from the illumination device 16 is deflected towards a relay optical system 84. The size of the through-hole 92a disposed on the optical axis C when the reflecting member 82 is disposed on the illumination optical path is large enough to transmit the illumination light beam focused by the objective lenses 4a to 4d.

The operation of the microscope examination apparatus 90 according to this embodiment, having the above-described structure, will be described below.

To carry out high-magnification examination using the microscope examination apparatus 90 according to this embodiment, the turret 13 is rotated to dispose the objective lens 4c and the zooming mechanism 15 on the optical axis C, and first arms 14 are turned to dispose the image-forming lens unit 5b on the optical axis C.

Depending on the object being examined, the turret 91 is rotated to selectively dispose one of the dichroic mirrors 47a, 47b, and 47c and the through-hole 92a on the optical axis C. Each of the dichroic mirrors 47a, 47b, and 47c can be attached and removed by removing the holder 93 from the turret 91 by loosening the setting screw 94. Thus, a dichroic mirror having characteristics suitable for the examination can be selected and attached.

When one of the dichroic mirrors 47a, 47b, and 47c is disposed on the optical axis C, the illumination light from the light source 2 is emitted from the illumination device 16 through an optical fiber 46, deflected vertically downwards at one of the dichroic mirrors 47a, 47b, or 47c in front of and opposing the illumination device, and is incident on the specimen A through the zooming mechanism 15 and the objective lens 4c.

In this case, the return light from the specimen A is focused by the objective lens 4c, enlarged by the zooming mechanism 15, is then transmitted thorough the through-hole 93a in the holder 93 on the turret 91 and one of the dichroic mirrors 47a, 47b, and 47c, and is imaged at the camera 6 by the image-forming lens unit 5b.

By disposing the through-hole 92a on the optical axis C, the illumination light from the light source 2 is deflected toward the relay optical system 84 at the reflecting member 82. Consequently, the specimen A is not illuminated through the zooming mechanism 15 and the objective lens 4c but is illuminated from the side at an angle, that is, off-axis illumination, so that the illumination light bypasses the zooming mechanism 15 and the objective lens 4c.

In such a case, the return beam from the specimen A is focused by the objective lens 4c and expanded by the zooming mechanism 15. Then, the expanded return light is transmitted through the through-hole 92a of the turret 91 and is imaged at the camera 6 by the image-forming lens unit 5b.

When low-magnification examination is carried out using the microscope examination apparatus 90 according to this embodiment, the turret 13 is rotated so that one of the objective lenses 4a, 4b, and 4d having low magnification powers is selectively disposed on the optical axis C. In addition, the first arms 14 are rotated to disposed the image-forming lens unit 5a on the optical axis C.

Furthermore, by rotating the turret 91, one of the dichroic mirrors 47a to 47c, having different properties, and the through-hole 92a are disposed on the optical axis C. When one of the dichroic mirrors 47a to 47c is disposed, the illumination light generated at the light source 2 is transmitted to the illumination device 16 via the optical fiber 46, is deflected at one of the dichroic mirrors 47a to 47c on the turret 91, is focused by one of the objective lenses 4a, 4b, and 4d, and is incident on the specimen A.

When the through-hole 92a is disposed on the optical axis C, the illumination beam from the light source 2 is deflected toward the relay optical system 84 at the reflecting member 82. Therefore, the specimen A is not illuminated through the objective lenses 4a, 4b, and 4d but is illuminated from the side at an angle, that is, off-axis illumination, so that the illumination light bypasses the objective lenses 4a, 4b, and 4d. The return light from the specimen A is focused by the objective lenses 4a, 4b, and 4c, is transmitted through the through-hole 92a of the turret 91, and is imaged at the camera 6 by the image-forming lens 5a.

For carrying out either high-magnification examination or low-magnification examination using the microscope examination apparatus 90 having the above-described structure, either on-axis illumination in which the specimen A is irradiated with light through the objective lenses 4a to 4d or off-axis illumination in which the specimen A is irradiated from the side and at an angle with light that bypasses the objective lenses 4a to 4d can be selected by rotating the turret 91 to selectively dispose one of the dichroic mirrors 47a to 47c and the through-hole 92a. Since one of the various dichroic mirrors 47a to 47c can be selected, one of the dichroic mirrors 47a to 47c having characteristics suitable for the return light to be examined can be selected.

Sixth Embodiment

Figure 25:
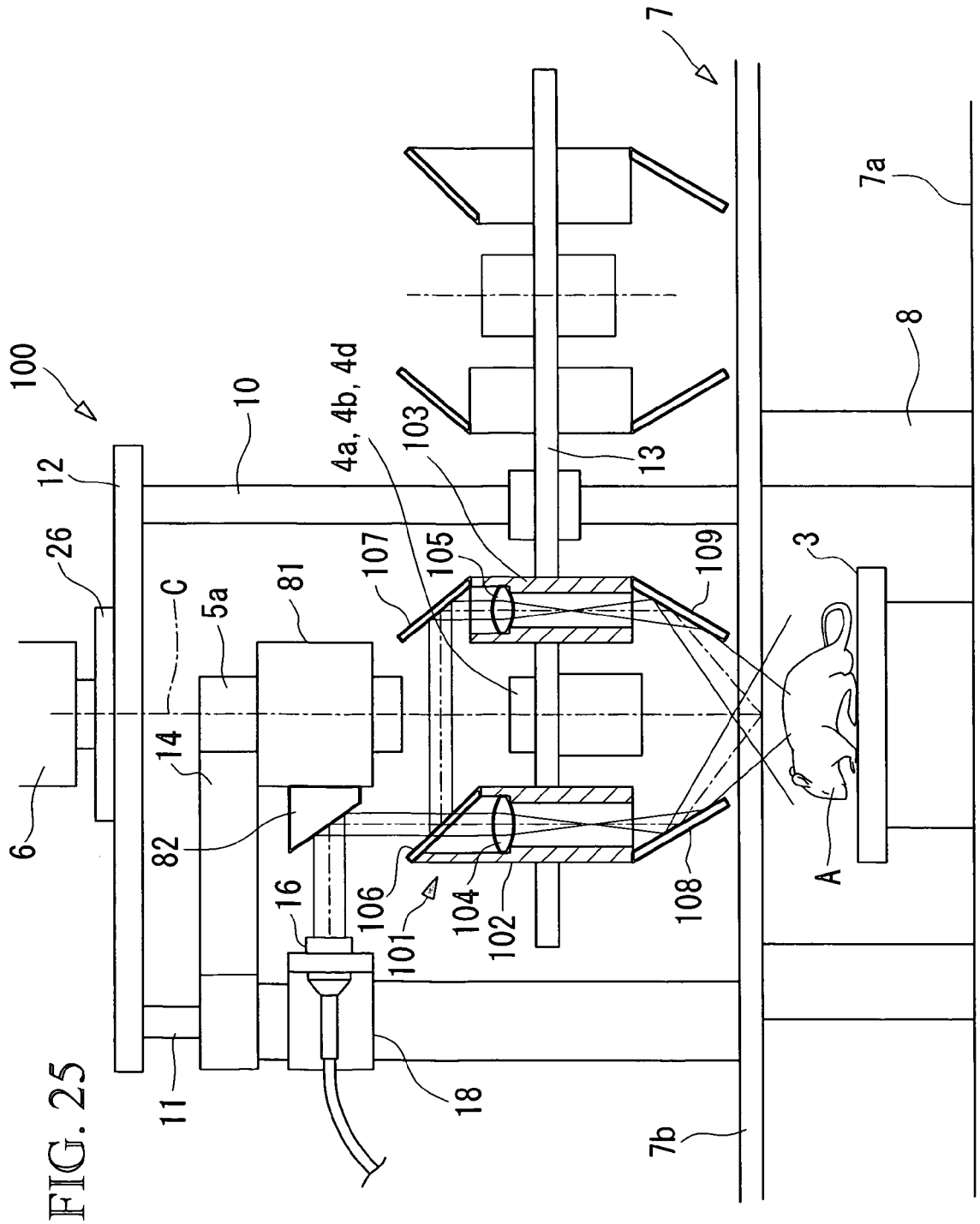
FIG. 25 is a partial longitudinal cross-sectional view illustrating a microscope examination apparatus according to a sixth embodiment of the present invention.

Next, a microscope examination apparatus 100 according to a sixth embodiment will be described with reference to FIG. 25.

The description of this embodiment is simplified by representing the components that are the same as those in the microscope examination apparatus 80 according to the above-described fourth embodiment with the same reference numerals as those in the fourth embodiment.

The microscope examination apparatus 100 according to this embodiment differs from the fourth embodiment in that a relay optical system 101 is not held on the support stand 11 but is held on a turret 13. Furthermore, the relay optical system 101 is provided for each of the objective lenses 4a to 4d. Each relay optical system 101 is constituted of a set of two components sandwiching each of the objective lenses 4a to 4d.

Each of the relay optical systems 101 includes two cylindrical outer barrels 102 and 103, focusing lenses 104 and 105 that are held by the outer barrels 102 and 103, respectively, a half mirror 106, and mirrors 107, 108, and 109. The outer barrels 102 and 103 penetrate through the turret 13 in the thickness direction and are fixed to the turret 13 with setting screws that are not shown in the drawing.

Inside the outer barrel 102 of the relay optical system 101, the half mirror 106, the focusing lens 104, and the mirror 108 are disposed in this order from the top in a substantially straight line. Inside the outer barrel 103, the mirror 107, the focusing lens 105, and the mirror 109 are disposed in this order from the top in a substantially straight line.

The outer barrel 102 is disposed at a position where an illumination beam that is deflected vertically downwards at a reflecting member 82, being fixed to a retaining member 81 on the image-forming lens unit 5a, is incident, when one of the objective lenses 4a to 4d and the image-forming lens unit 5a is disposed on the optical axis C.

In this state, the half mirror 106 is disposed vertically below the reflecting member 82 so that the half mirror 106 reflects the examination light deflected at the reflecting member 82. The mirror 107 is disposed at a position horizontally separated from the half mirror 106 so that the illumination beam deflected at the half mirror 106 is incident on the mirror 107.

The positions of the outer barrels 102 and 103 with respect to the turret 13 and the positions and angles of the half mirror 106, the mirrors 107, 108, and 109, and the focusing lenses 104 and 105, inside the outer barrels 102 and 103, are optimally set in each relay optical system 101 so that the range of examination of the objective lenses 4a to 4d can be thoroughly illuminated.

The operation of the microscope examination apparatus 100 according to this embodiment, having the above-described structure, will be described below.

To carry out low-magnification examination using the microscope examination apparatus 100 according to this embodiment without disposing the zooming mechanism 15 on the optical axis C, the turret 13 is turned to selectively dispose one of the objective lenses 4a, 4b, and 4d on the optical axis C. At this time, each relay optical system 101 provided for each of the objective lenses 4a, 4b, and 4d is set.

The illumination beam generated at a light source 2 is deflected at the reflecting member 82 and is directed to the relay optical system 101. The illumination light that is transmitted through the half mirror 106 on the upper end of the outer barrel 102 is adjusted by the focusing lens 104. Then, the illumination beam is deflected at the mirror 108 and is incident on a specimen A. The illumination light reflected at the half mirror 103 is deflected towards the focusing lens 105 at the mirror 107. The illumination light beam is adjusted at the focusing lens 105. The beam is deflected at the mirror 109 and is incident on the specimen A.

In this way, with the microscope examination apparatus 100 according to this embodiment, examination light emitted from the light source 2 can be emitted to the specimen A via two paths. Since the positions of the optical devices in the two relay optical systems 101 that sandwich each of the objective lenses 4a to 4d are adjusted, a range corresponding to the range of examination of each of the objective lenses 4a to 4d can be illuminated.

The light source 2 according to this embodiment is not limited to one light source 2, and, instead, a plurality of light sources may be provided. In such a case, the number of relay optical systems 101 required for each of the objective lenses 4a to 4d is equal to at least the number of light sources 2 being provided.

Seventh Embodiment

Figure 26:
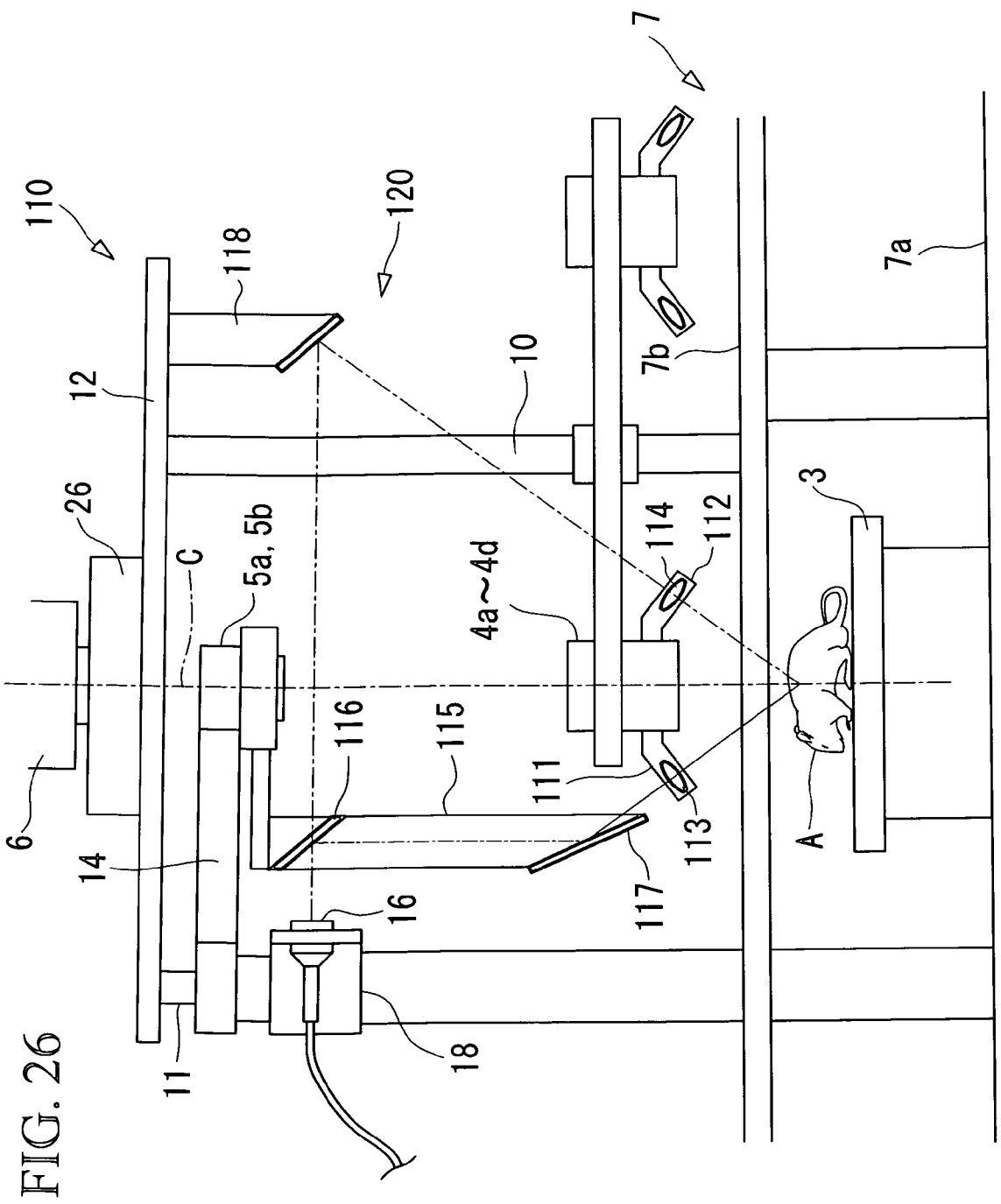
FIG. 26 is a partial longitudinal cross-sectional view illustrating a microscope examination apparatus according to a seventh embodiment of the present invention.

Next, a microscope examination apparatus 110 according to a seventh embodiment will be described with reference to FIG. 26.

The description of this embodiment is simplified by representing the components that are the same as those in the microscope examination apparatus 80 according to the above-described fourth embodiment with the same reference numerals as those in the fourth embodiment.

The microscope examination apparatus 110 according to this embodiment includes a relay optical system 120 including lenses 113 and 114 that are held by holders 111 and 112, respectively, that are fixed to each of the objective lenses 4a to 4d; a half mirror 116 and a mirror 117 held by a holder 115 that is fixed to each of the image-forming lens units 5a and 5b; and a mirror 119 held by a holder 118 that is fixed to a base 12. The half mirror 116 and the mirror 117 are disposed at positions vertically separated from each other. For example, as shown in FIG. 26, when the image-forming lens unit 5a is disposed on the optical axis C, the half mirror 116 is disposed in front of and opposing an illumination device 16 so that the illumination device 16, the half mirror 116, and the mirror 118 are horizontally aligned in a substantially straight line.

In this way, an illumination beam emitted from the illumination device 16 and transmitted through the half mirror 116 is reflected by the mirror 118 and directed to a specimen A. The illumination beam deflected vertically downwards at the half mirror 116 is deflected again at the mirror 117 and is directed to the specimen A via another path. The focusing lenses 113 and 114 are disposed so that the illumination beams deflected at the mirrors 117 and 118, respectively, are focused onto the examination site of the specimen A.

In such a case, the focusing lenses 113 and 114 do not necessarily have to be fixed to each of the objective lenses 4a to 4d.

With the microscope examination apparatus 110 according to this embodiment, when carrying out low-magnification examination when the image-forming lens unit 5a is disposed on the optical axis C, the illumination light emitted from the half mirror 116 is split and directed to the transmissive side and the deflective side of the half mirror 116. The illumination beam transmitted through the illumination device 16 is deflected at the mirror 118 directly towards the specimen A. The illumination beam deflected at the half mirror 116 is deflected again at the mirror 117 and directed towards the specimen A. The illumination beams deflected at the mirrors 117 and 118 are focused and are incident on the examination site of the specimen A in the relay optical system 401.

In this way, with the microscope examination apparatus 110 according to this embodiment, the same advantages as those according to the above-described sixth embodiment are provided. In addition, the mirror 118 directly transmits illumination light to the specimen A, reducing the number of mirror reflections of the beam and efficiently illuminating the specimen A.

The fifth and sixth embodiments or the fifth and seventh embodiments may be combined. In such a case, the advantages of both embodiments are provided.

A stage 3 according to this embodiment is disposed on a first base 7a and is capable of moving, in two horizontal directions and a vertical direction, the specimen A placed on a tray 9 that is composed of a transparent material or a light-absorbing black material. Instead, however, as shown in FIGS. 27 to 33, a fixed stage 130 that is fixed to the first base 7a and integrally provided with the first base 7a may be used.

Figure 27:
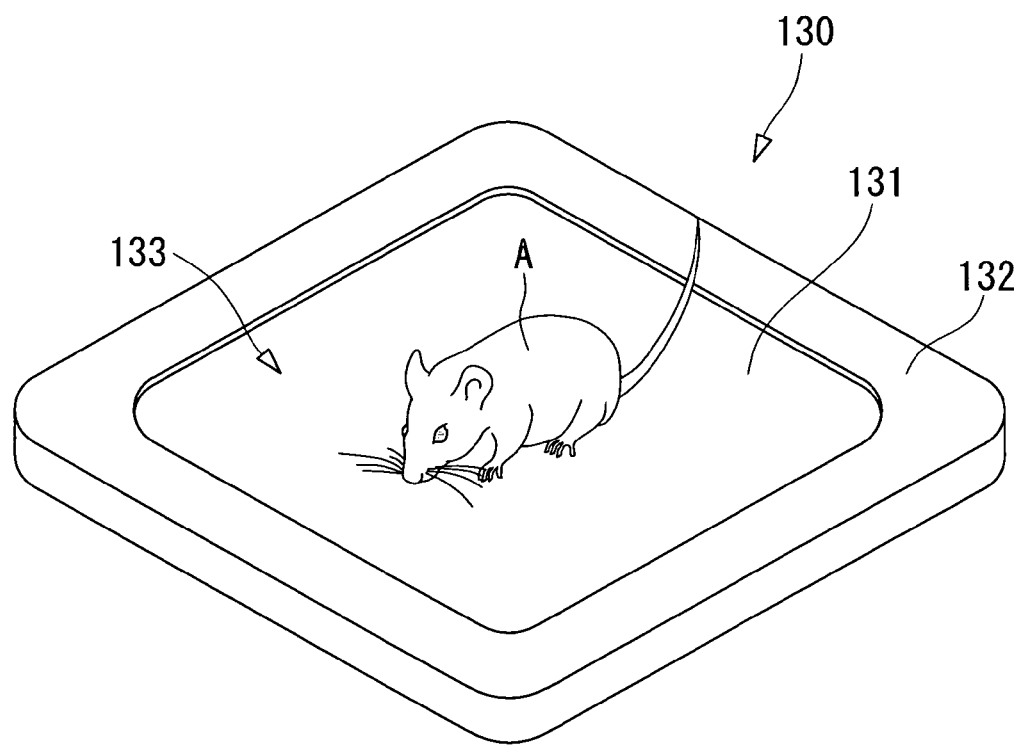
FIG. 27 is a perspective view illustrating a first modification of a stage in the microscope examination apparatus according to the present invention.
Figure 28:
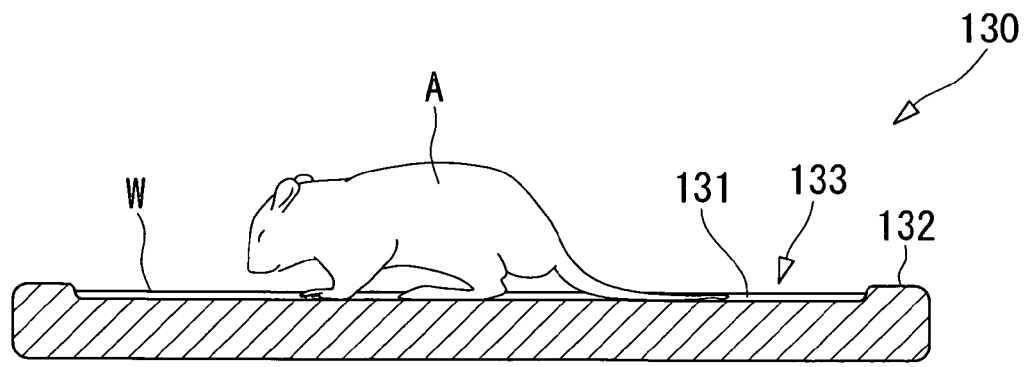
FIG. 28 is a longitudinal cross-sectional view illustrating the stage shown in FIG. 27.

For the stage 130, as illustrated in FIGS. 27 and 28, the bottom surface of a depression 133 that is indented by a step with respect to a peripheral area 132 is a placement surface 131 for placing the specimen A. It is preferable that the volume of the depression 133 be sufficient for holding a liquid W, such as body fluid, which may spill when the specimen A is dissected, or normal saline solution. In this way, the liquid W can be prevented from overflowing outside the stage 130 and entering areas around the stage 130 that are difficult to wipe or wash. In particular, since it is difficult to visually confirm that the liquid W is spilling when carrying out examination in a dark box, it is effective to used the above-described stage 130.

Figure 29:
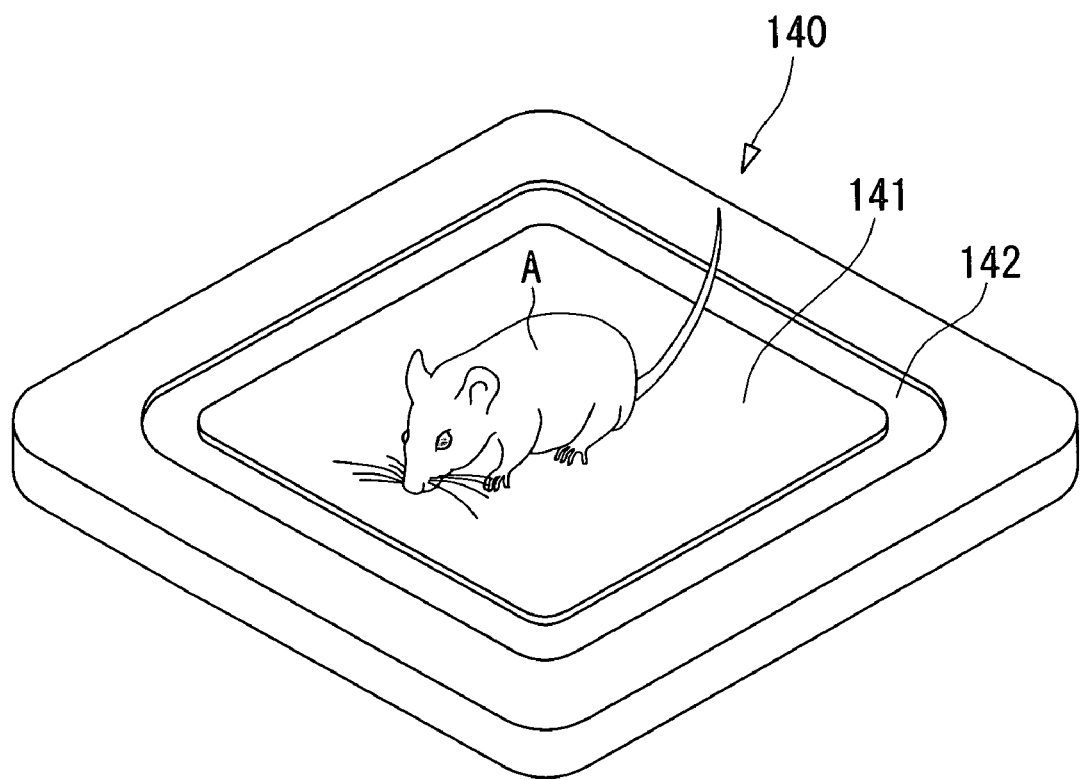
FIG. 29 is a perspective view illustrating a second modification of a stage in the microscope examination apparatus according to the present invention.
Figure 30:
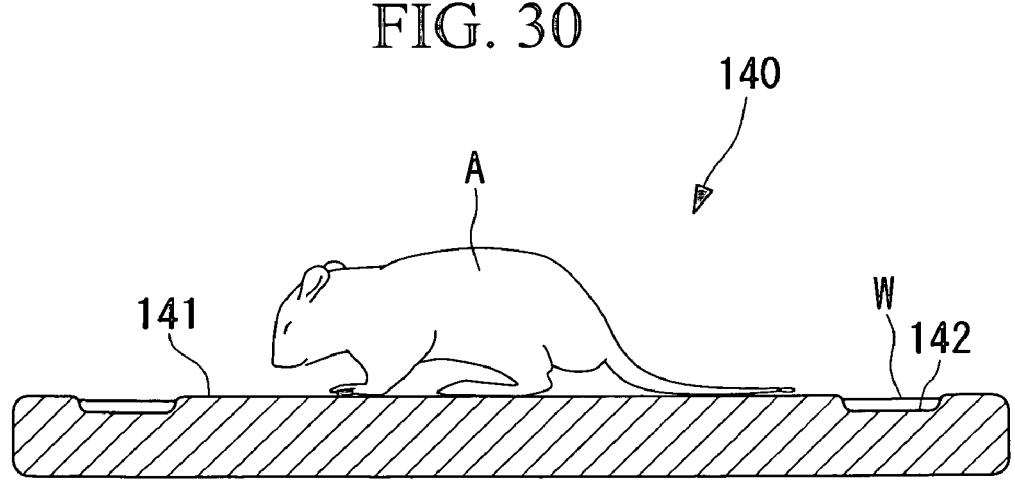
FIG. 30 is a longitudinal cross-sectional view illustrating the stage shown in FIG. 29.

A stage 140, illustrated in FIGS. 29 and 30, has a depressed peripheral groove 142 around a placement surface 141 for placing the specimen A. It is preferable that the volume of the peripheral groove 142 is sufficient for holding a liquid W, such as body fluid, which may spill when the specimen A is dissected, or normal saline. In this way, the same advantages as those of the above-described stage 140 are provided, normally, that the liquid W can be prevented from overflowing outside the stage 140 and entering areas around the stage 140 that are difficult to wipe or wash. With the stage 140, since the spilled liquid W pools in the peripheral groove 142 that is lower than the placement surface 141, another advantage is provided in that the specimen A can be prevented from being soaked in the liquid W.

Figure 31:
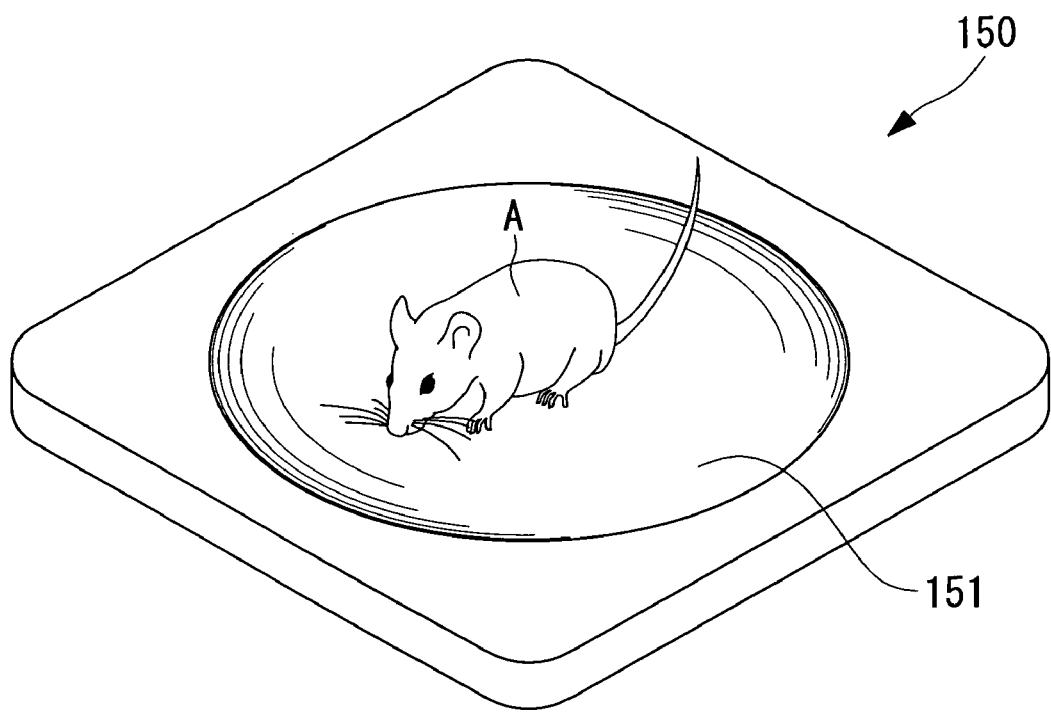
FIG. 31 is a perspective view illustrating a third modification of a stage in the microscope examination apparatus according to the present invention.
Figure 32:
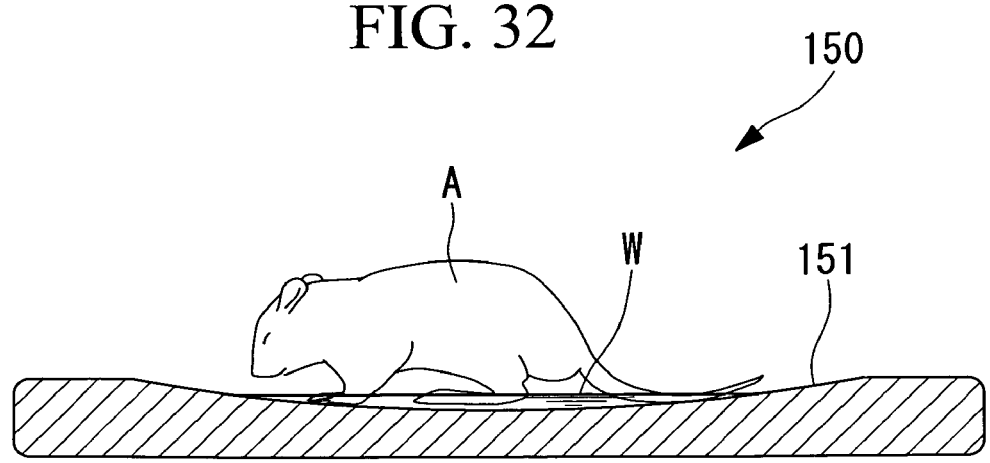
FIG. 32 is a longitudinal cross-sectional view illustrating the stage shown in FIG. 31.

A stage 150 illustrated in FIGS. 31 and 32 includes a depression 151 having a concave placement surface for placing a specimen A. In this case, also, it is preferable that the volume of the depression 151 be sufficient for holding a liquid W, such as body fluid, which may spill when the specimen A is dissected, or normal saline. The same advantages are provided by the stage 150 as those of the above-described stage 150.

Figure 33:
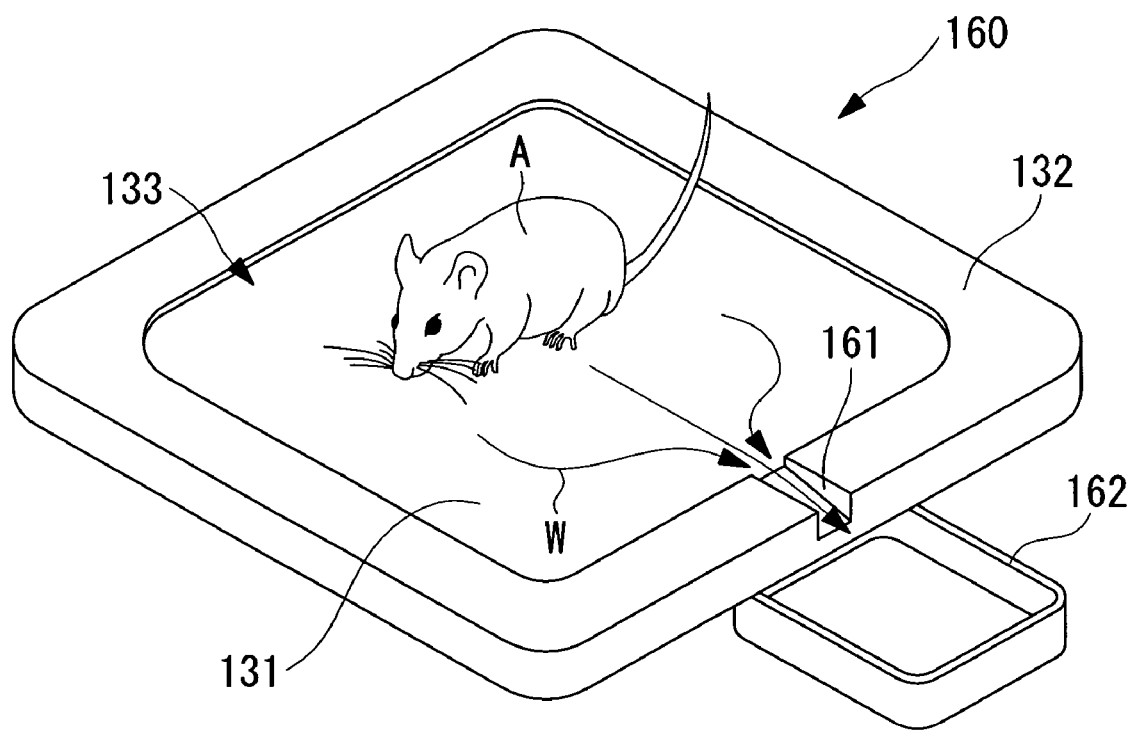
FIG. 33 is a perspective view illustrating a fourth modification of a stage in the microscope examination apparatus according to the present invention.

A stage 160 illustrated in FIG. 33 is the same as the stage 130 illustrated in FIGS. 27 and 28, except that a notch 161 is provided at a part of the peripheral area 132 so that the liquid W pooled inside the depression 133 can be drained. Outside the notch 161, a receiving pan 162 is provided for collecting the drained liquid W. In this way, similar to the stage 140 illustrated in FIG. 29, the specimen A can be prevented from being soaked in the liquid W. The notch 161 and receiving pan 162 may be provided for the stage 150 illustrated in FIG. 31. Furthermore, through-holes (not shown in the drawings) for draining the liquid W may be provided in the placement surfaces 131 and 151 of the stages 130 and 150, respectively, and containers for collecting the liquid W may be provided at the ends of the through-holes.

Eighth Embodiment

This embodiment is directed to an examination apparatus for a living organism, organ, or tissue. Here, "living organism" is a living mammal selected from the group consisting of mouse, rat, rabbit, cat, dog, pig, cow, sheep, goat, horse, monkey, gorilla, chimpanzee, and human. "Organ" is an organ selected from the group consisting of brain, lung, liver, spleen, bone marrow, thymus, heart, lymph, blood, bone, cartilage, pancreas, liver, gall bladder, stomach, intestine, testis, ovary, uterus, rectum, nervous system, gland, and blood vessel. "Tissue" is a three-dimensional structure of a plurality of cells.

Figure 34:
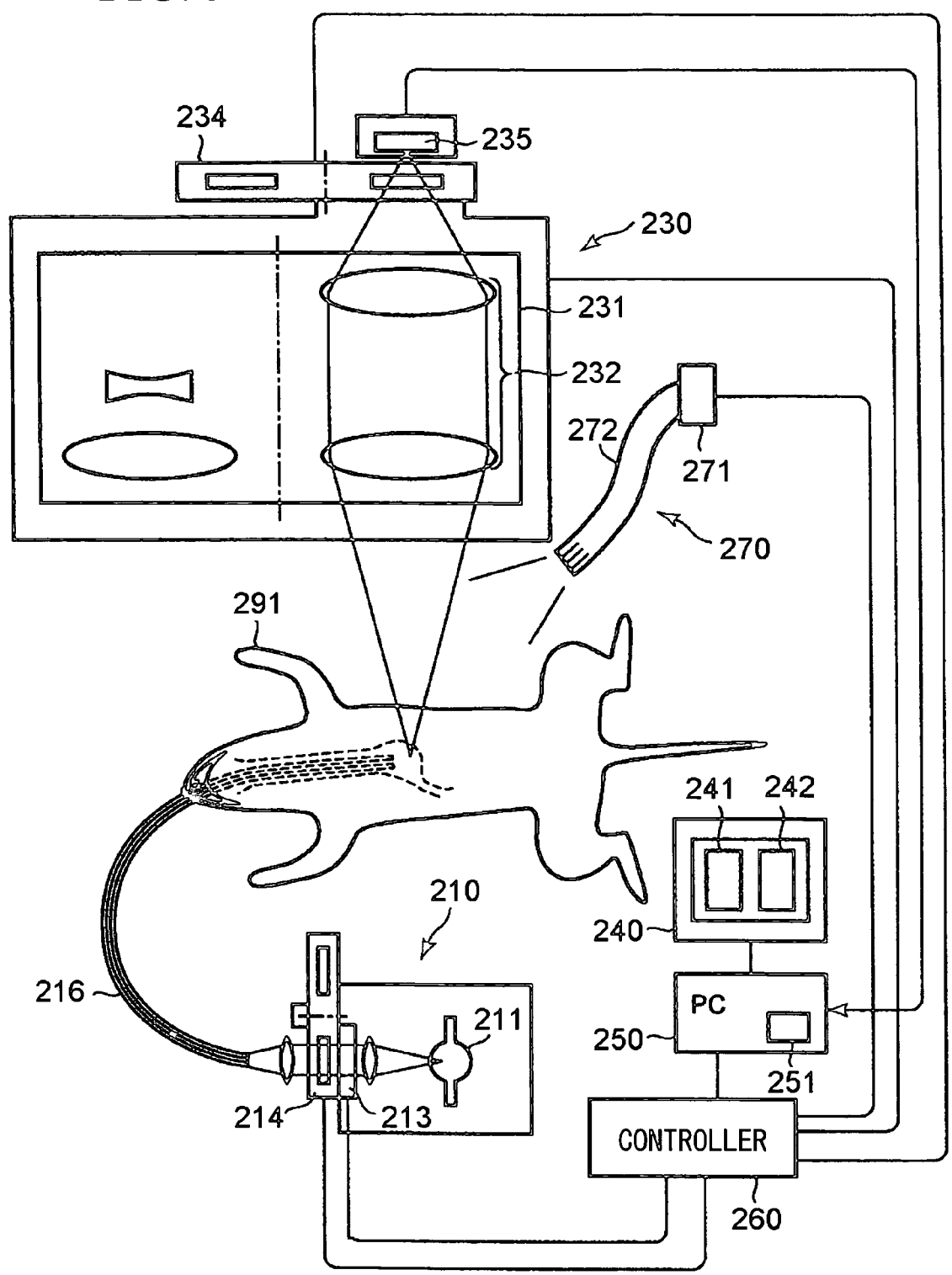
FIG. 34 is a schematic view of the structure of an examination apparatus according to an eighth embodiment of the present invention.

FIG. 34 is a schematic view illustrating the structure of an examination apparatus according to an eighth embodiment. As shown in FIG. 34, the examination apparatus according this embodiment includes an illumination device 210 for internally illuminating a living organism, organ, or tissue and an image-capturing device 230 for obtaining an optical image, i.e., at least one of a transmission image and a fluorescence image, of a living organism, organ, or tissue by capturing an external image of a living organism, organ, or tissue.

The illumination device 210 includes a light source 211 for generating an illumination light or excitation light and a light-emitting unit 216 for externally emitting the illumination light or excitation light. The light-emitting unit 216 may be guided into the living organism, organ, or tissue.

To "guide" the light-emitting unit 216 into a living organism, organ, or tissue means to insert the light-emitting unit 216 into a cavity in the living organism, organ, or tissue, to puncture the living organism, organ, or tissue with the light-emitting unit 216, or to press the light-emitting unit 216 against the living organism, organ, or tissue.

The light source 211 is constituted of but not limited to, for example, a xenon lamp, a mercury lamp, or a halogen lamp. The light-emitting unit 216 is constituted of but not limited to, for example, a fiber bundle.

According to this embodiment, the living organism, organ, or tissue, i.e., the object to be examined, is a mouse 291. The light-emitting unit 216 is inserted through the mouth to the stomach or through the stomach to the intestine of the mouse 291. The light-emitting unit 216 may be inserted into the body of the mouse 291 through the ear, nose, anus, or uterine cavity.

The illumination device 210 further includes a control unit for controlling the emission of the illumination beam or excitation beam from the light-emitting unit 216. The control unit is constituted of but not limited to, for example, a shutter 213.

The light source 210 includes a wavelength-changing unit for changing the wavelength of the illumination beam or excitation beam emitted from the light-emitting unit 216. The wavelength-changing unit, for example, includes a plurality of band-pass filters having different transmission wavelength bands and an illumination-light filter turret 214 that is capable of selectively disposing one of the filters in the optical path.

Figure 35:
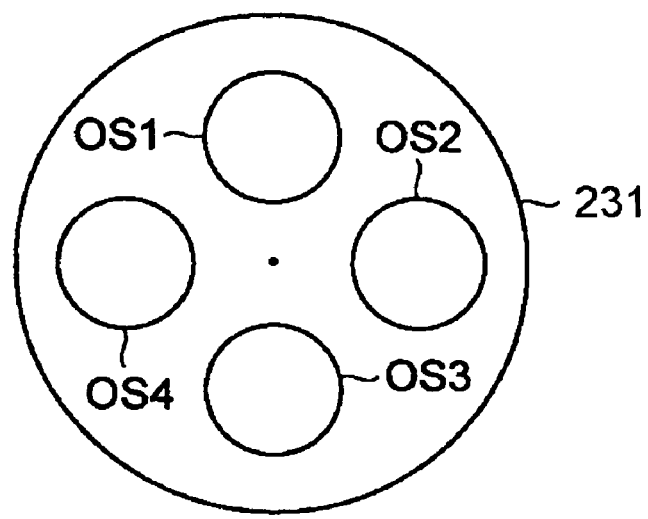
FIG. 35 is a plan view of an image-forming optical system turret shown in FIG. 34.

The image-capturing device 230 includes an image-forming optical system 232 for imaging the light from the living organism, organ, or tissue and an image-capturing element 235 for generating an image signal by photoelectrically converting the optical image formed by the image-forming optical system 232. The image-capturing device 230 includes a plurality of image-forming optical systems having different magnifying powers and an image-forming optical system turret 231 for selectively disposing one of the image-forming optical systems in the optical path. The image-forming optical system turret 231 includes, for example, four image-forming optical systems OS1 to OS4, as illustrated in FIG. 35. For example, the image-forming optical system OS1 has a magnifying power of 5 times, the image-forming optical system OS2 has a magnifying power of 1.5 times, the image-forming optical system OS3 has a magnifying power of 1 times, and the image-forming optical system OS4 has a magnifying power of 0.8 times. The image-forming optical system turret 231 is capable of rotating around a central axis and is capable of disposing one of the image-forming optical systems OS1 to OS4 in the optical path. Accordingly, the image-forming optical system 232 for imaging the light from the living organism, organ, or tissue is formed of one of the image-forming optical systems OS1 to OS4.

The image-capturing element 235 is constituted of but not limited to, for example, a CCD.

The image-capturing device 230 further includes a wavelength-changing unit for changing the wavelength of the light (examination light or fluorescence light) incident on the image-capturing element 235. The wavelength-changing unit, for example, includes a plurality of band-pass filters having different transmission wavelength bands and a light-reception filter turret 234 that is capable of selectively disposing one of the filters in the optical path.

The examination apparatus further includes a display device 240 for displaying an image and an image-processing unit 250 for processing the image signal from the image-capturing device 230 and for forming an image to be displaying on the display device 240. The image-processing unit 250 is constituted of but not limited to, for example, a personal computer (PC). The image-processing unit 250 further includes an image-recording unit 251 for recording images. The image-recording unit 251 is constituted of but not limited to, for example, a hard disk.

The examination apparatus further includes an illumination optical system 270 for externally illuminating a living organism, organ, or tissue. The illumination optical system 270 is constituted of, for example, a light source 271 for generating illumination light and a fiber bundle for transmitting the illumination light generated at the light source 271.

The examination apparatus further includes a controller 260 for controlling the shutter 213, an illumination-light filter turret 214, an image-forming optical system turret 231, a filter turret 234 for light reception, and a light source 217.

In the examination apparatus according to this embodiment, illumination light or excitation light emitted from the light-emitting unit 216 internally illuminates the mouse 291. The emission of the illumination light or the excitation light from the light-emitting unit 216 is controlled by the shutter 213. The wavelength of the illumination light from the light-emitting unit 216 is changed by the illumination-light filter turret 214.

Part of the light transmitted through the mouse 291 and part of the fluorescence generated at the mouse 291 are incident on the image-forming optical system 232. The light incident on the image-forming optical system 232 is imaged on the reception plane of the image-capturing element 235. The image-forming optical system 232 employs one of the image-forming optical systems OS1 to OS4 having a suitable magnifying power and being selected by using the image-forming optical system turret 231.

Light from the image-forming optical system 232 is transmitted through the light-reception filter turret 234 and is incident on the image-capturing element 235. The wavelength of the light incident on the image-capturing element 235 can be changed by the light-reception filter turret 234.

The image-capturing element 235 generates an image signal by photoelectrically converting the formed optical image. The image signal is sent to the image-processing unit 250. The image-processing unit 250 processes the image signal and forms an image to be displayed on the display device 240, and the image is displayed on the display device 240. Furthermore, the image is recorded on the image-recording unit 251, such as a hard disk, if required.

Figure 36:
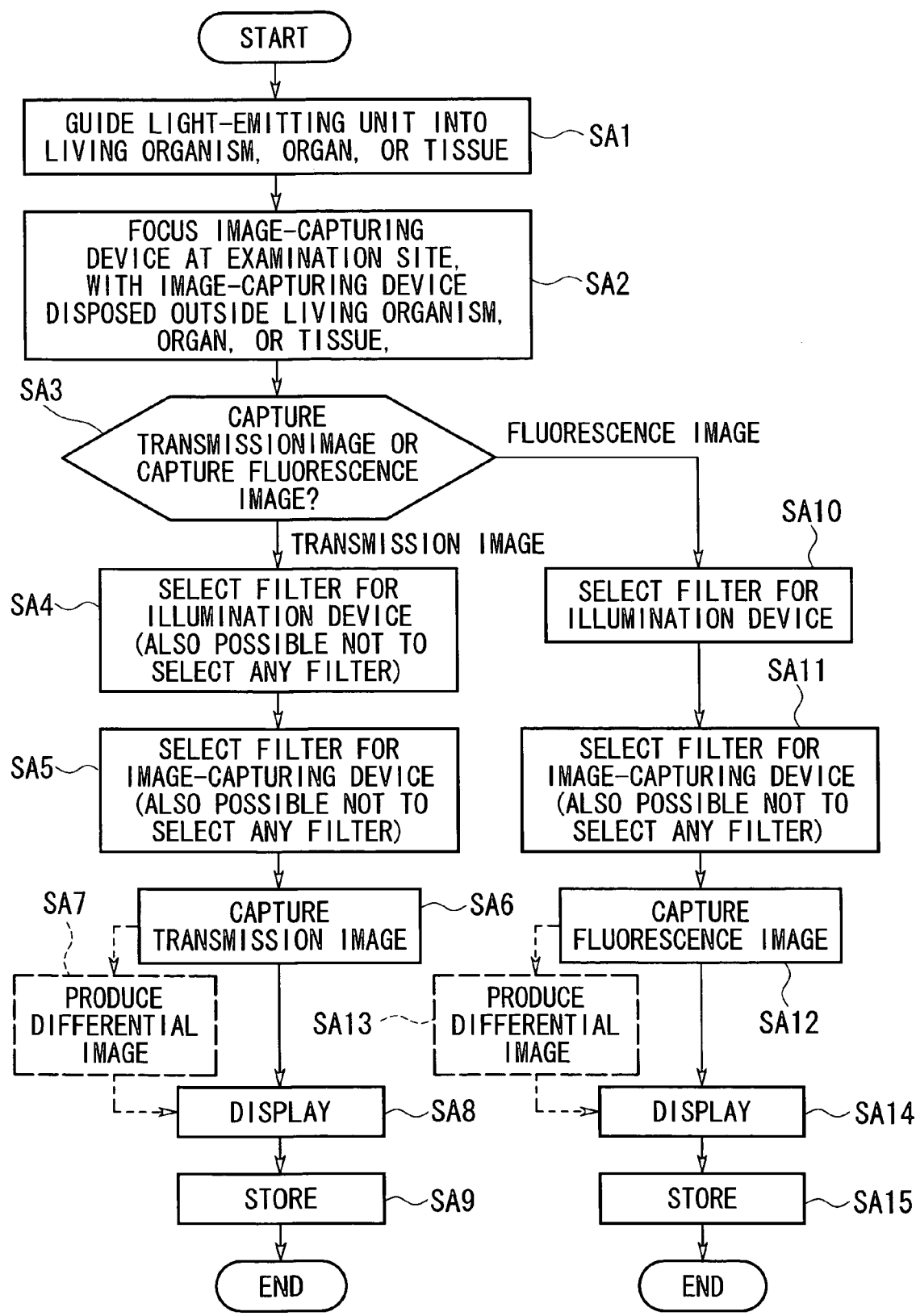
FIG. 36 is a flow chart of an examination process of the examination apparatus according to the eighth embodiment of the present invention.

FIG. 36 is a flow chart of the examination carried out by the examination apparatus according to this embodiment. The examination process carried out by the examination apparatus according to this embodiment will be described below with reference to FIG. 36.

First, the light-emitting unit 216 constituted of the fiber bundle of the illumination device 210 is guided into a living organism, organ, or tissue (SA1). More specifically, the light-emitting unit 216 is inserted into the mouse 291 through the mouth.

Next, while the mouse 291 is internally illuminated by the light-emitting unit 216 or externally illuminated by the illumination optical system 270, the image-capturing device 230 that is disposed outside the living organism, organ, or tissue, i.e., the mouse 291 is focused onto the examination site (SA2).

Next, it is determined whether a transmission image or a fluorescence image is to be captured (SA3).

When a transmission image is to be captured, a transmission image is captured in accordance with the following steps.

First, if required, the filter to be used is selected at the illumination device 210 (SA4). The selected filter is disposed in the optical path using the illumination-light filter turret 214. When a filter is not required, a filter is not disposed in the optical path.

Since light having long wavelengths, such as near-infrared light, is easily transmitted through a living organism, organ, or tissue compared to visible light, if necessary, a filter is selected at the image-capturing device 230 (SA5). The selected filter is disposed in the optical path using the light-reception filter turret 234. When a filter is not required, a filter is not disposed in the optical path.

Illumination light or excitation light is emitted from the light-emitting unit 216 to internally illuminate the mouse 291. The illumination optical system 270 is turned off.

A transmission image is captured by the image-capturing device 230 (SA6). If the exposure time is not optimal, the illumination and the exposure time are optimized.

If required, a differential image of the transmission image is produced at the image-processing unit 250 (SA7). The differential image is displayed by converting the diffused light generated by the refractive-index distribution of the living organism, organ, or tissue into contrast. In this way, the shape of the living organism, organ, or tissue can be easily recognized.

The transmission image is displayed on the display device 240 (SA8). If a differential image of the transmission image is produced, the transmission image is displayed next to the transmission image on the display device 240, if required, as an image 241 and an image 242, as shown in FIG. 34. In this way, the morphological characteristics of the captured site can be observed.

The transmission image is stored in the image-recording unit 251 (SA9). If a differential image of the transmission image is produced, the transmission image is also displayed on the display device 240.

To capture a transmission image in this way, the image-capturing device 230 captures a transmission image, the image-processing unit 250 produces a differential image of the transmission image, and the display device 240 displays a fluorescence image and a differential image of the transmission image adjacent to each other.

When a transmission image is to be captured, the transmission image is captured in accordance with the following steps.

First, the filter to be used is selected at the illumination device 210 (SA10). The selected filter is disposed in the optical path using the illumination-light filter turret 214. In this way, the living organism, organ, or tissue can be internally illuminated with an excitation beam having a wavelength corresponding to a fluorescent protein, such as green florescent protein (GFP), DsRed, RFP, CFP, YFP, or Kaede, or a fluorescent dye, such as FITC, Alexa Fluor 488, Alexa Fluor 647, Alexa Fluor 660, Alexa Fluor 680, Alexa Fluor 700, Alexa Fluor 750, Rhodamine, Texas Red, Cy5, Cy5.5, Cy7, IRDye750, or ICG.

If required, the filter to be used is selected at the image-capturing device 230 (SA5). The selected filter is disposed in the optical path using the light-reception filter turret 234. When a filter is not required, a filter is not disposed in the optical path. For example, to capture a fluorescence image in a specific wavelength band, a band-pass filter corresponding to the desired fluorescence image is disposed in the optical path. In this way, a fluorescence image corresponding to the fluorescent protein or fluorescent dye in the organ or tissue can be selectively captured by the image-capturing element 235. To capture a fluorescence image in a wide wavelength band, a filter is not disposed in the optical path.

Illumination light or excitation light is emitted from the light-emitting unit 216 to internally illuminate the mouse 291. The illumination optical system 270 is turned off.

A fluorescence image is captured by the image-capturing device 230 (SA6). If the exposure time is not optimal, the illumination and the exposure time are optimized.

If required, a differential image of the fluorescence image is produced at the image-processing unit 250 (SA7). The differential image is displayed by changing the contrast of the diffused light generated by the refractive-index distribution of the living organism, organ, or tissue. In this way, the shape of the living organism, organ, or tissue can be easily recognized.

The fluorescence image is displayed on the display device 240 (SA8). If a differential image of the fluorescence image is produced, the fluorescence image is displayed next to the fluorescence image on the display device 240, if required, as an image 241 and an image 242, as shown in FIG. 34. In this way, the morphological characteristics of the captured site can be observed.

The fluorescence image is stored in the image-recording unit 251 (SA9). If a differential image of the fluorescence image is provided, the fluorescence image is also stored on the image-recording unit 251.

To capture a fluorescence image in this way, the image-capturing device 230 captures a fluorescence image, and the display device 240 displays a fluorescence image. In this case, by comparing the fluorescence image with another image, the changes over time of the amount and area of the fluorescent substance in the living organism, organ, or tissue can be compared.

More preferably, the image-capturing device 230 captures a fluorescence image, the image-processing unit 250 produces a fluorescence image and a differential image of the fluorescence image, and the display device 240 displays the fluorescence image and the differential image of the fluorescence image adjacent to each other. In other words, a fluorescence image is obtained by capturing an external image of the living organism, organ, or tissue, and the fluorescence image and the differential image of the fluorescence image are displayed adjacent to each other on the display device 240. By comparing the fluorescence image and the differential image of the fluorescence image, the site where fluorescence is generated can be specified. Moreover, the position (distribution), the amount, and/or the area of the fluorescent substance in the living organism, organ, or tissue can be studied and/or confirmed on the basis of a fluorescence image and a differential image of the fluorescence image by obtaining a fluorescence image by capturing an external image of the living organism, organ, or tissue.

Conventionally, when a living organism, organ, or tissue is externally illuminated, the light absorbed at the surface of the living organism, organ, or tissue generates autofluorescence, causing a reduction in the contrast of the image. Light reflected at the surface of the living organism, organ, or tissue may act as noise. Although the surface of the living organism, organ, or tissue is brightly illuminated, the inside of the living organism, organ, or tissue is illuminated less brightly than the surface.

In contrast, according to this embodiment, the light-emitting unit 216 that externally emits illumination light or excitation light is guided into a living organism, organ, or tissue, and the illumination light or excitation light is emitted from the light-emitting unit 216 so as to internally illuminate the living organism, organ, or tissue. In this way, the generation of autofluorescence is suppressed. Moreover, the site to be examined on the living organism, organ, or tissue can be illuminated from a close distance. Since the living organism, organ, or tissue is internally illuminated, unlike when the living organism, organ, or tissue is externally illuminated, there are no adverse effects caused by light reflected from the surface of the living organism, organ, or tissue on the image. Since light emitted from the light-emitting unit 216 guided into the living organism, organ, or tissue, i.e., the light-emitting unit 216 that is inserted into the living organism, organ, or tissue, the light-emitting unit 216 that penetrates through the living organism, organ, or tissue, or the light-emitting unit 216 that is pressed against the living organism, organ, or tissue, is reflected multiple times inside the living organism, organ, or tissue, the living organism, organ, or tissue is efficiently illuminated.

As a result, the examination apparatus according to this embodiment is capable of efficiently illuminating a living organism, organ, or tissue, thus enabling examination at high resolution.

It is preferable that, during examination of a living organism, organ, or tissue, an image of the entire examination site of the living organism, organ, or tissue can be captured and a site of interest within the examination site can be enlarged. Therefore, the examination apparatus should be able to project optical images on the image-capturing element at a magnifying power of 1 to 5 times, or more preferably 0.3 to 20 times, by switching among a plurality of image-forming optical systems. If this range of magnification is not maintained, a plurality of examination apparatuses, such as a low-magnification examination apparatus and a high-magnification examination apparatus, corresponding to the magnifying powers of the optical image to be captured must be provided. As a result, the system will become very inconvenient to use. To efficiently capture a fluorescence image of the living organism, organ, or tissue, it is preferable that the image-forming optical system have an optimal numerical aperture (NA). For example, if the NA is not maintained at 0.05 or greater for a magnifying power of 1 times, it is extremely difficult to efficiently capture a fluorescence image. Moreover, it is extremely difficult to maintain an NA of 0.25 or greater due to the design.

In contrast, with the examination apparatus according to this embodiment, by switching among the four image-forming optical systems OS1 to OS4 using the image-forming optical system turret 231, a living organism, organ, or tissue can be examined at four different magnifying powers, 0.8, 1, 1.5, and 5 times. Since the image-forming optical systems are switched using the image-forming optical system turret 231, it is easy to maintain a relatively large NA even for a low-magnification image-forming optical system. Thus, a relatively bright fluorescence image can be obtained even when the magnifying power is low.

As described above, with this embodiment, the light-emitting unit 216 for externally emitting an illumination beam or excitation beam is guided into a living organism, organ, or tissue and an illumination beam or excitation beam is emitted from the light-emitting unit 216 so as to internally illuminate the living organism, organ, or tissue.

Furthermore, an optical image, i.e., at least one of a transmission image and a fluorescence image, of a living organism, organ, or tissue is obtained by capturing an external image of the living organism, organ, or tissue, and the obtained optical image is displayed on the display device 240.

For example, a transmission image is obtained by capturing an external image of a living organism, organ, or tissue, and the obtained transmission image is displayed on the display device 240.

Moreover, a transmission image is obtained by capturing an external image of a living organism, organ, or tissue, and the transmission image and a differential image of the transmission image are displayed adjacent to each other on the display device 240.

Moreover, a fluorescence image is obtained by capturing an external image of a living organism, organ, or tissue, and the fluorescence image is displayed on the display device 240. Moreover, the changes over time of the amount and area of the fluorescent substance in the living organism, organ, or tissue can be compared and studied by obtaining a fluorescence image by capturing an external image of a living organism, organ, or tissue and comparing the obtained fluorescence image with another image.

Moreover, a fluorescence image is obtained by capturing an external image of a living organism, organ, or tissue, and the fluorescence image and a differential image of the fluorescence image are displayed adjacent to each other on the display device 240. Moreover, the position (distribution), amount, and area of the fluorescent substance in the living organism, organ, or tissue can be studied and/or confirmed on the basis of a fluorescence image and a differential image of the fluorescence image by obtaining a fluorescence image by capturing an external image of the living organism, organ, or tissue.

According to this embodiment, the light-emitting unit 216 is inserted in a cavity of a living organism, organ, or tissue for illumination. More specifically, the living organism, organ, or tissue is the mouse 291, and the light-emitting unit 216 is inserted into the mouth of the mouse 291. However, the insertion point of the light-emitting unit 216 is not limited to the mouth, and, instead, the light-emitting unit 216 may be inserted into the nose, uterine cavity, anus, or ear of the mouse 291 for illumination.

According to this embodiment, the light-emitting unit 216 is inserted in a cavity of the living organism, organ, or tissue, i.e., the mouth of the mouse 291 for illumination. However, the light-emitting unit 216 may penetrate through the living organism, organ, or tissue, i.e., the mouse 291, for illumination or may be pressed against the living organism, organ, or tissue, i.e., the mouse 291, for illumination.

Ninth Embodiment

Figure 37:
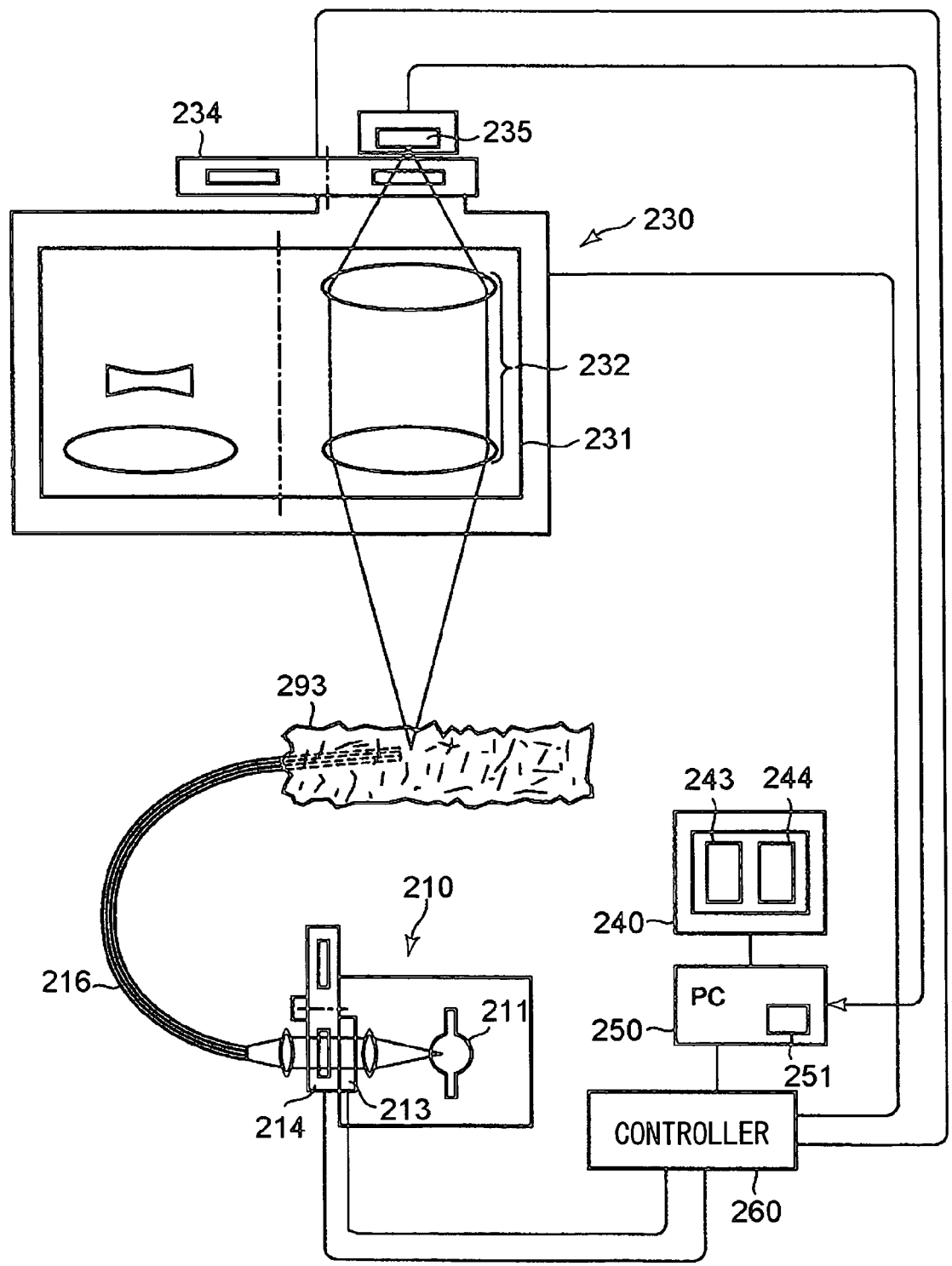
FIG. 37 is a schematic view of the structure of an examination apparatus according to a ninth embodiment of the present invention.

This embodiment is directed to another examination apparatus. FIG. 37 is a schematic view illustrating the structure of an examination apparatus according to a ninth embodiment of the present invention. The examination apparatus according to this embodiment is similar to the examination apparatus according to the eighth embodiment, illustrated in FIG. 34. The components illustrated in FIG. 37 that are represented by the same reference numerals as the components illustrated in FIG. 34 are same components, and detailed descriptions thereof are omitted.

As shown in FIG. 37, a living organism, organ, or tissue according to this embodiment is a piece of fresh cow intestine 293 that has just been cut off. A light-emitting unit 216 constituted of a fiber bundle is inserted into the cow intestine 293. The examination apparatus according to this embodiment differs from that according to the eighth embodiment in that an illumination optical system for externally illuminating the living organism, organ, or tissue is not included. The remaining structure of the examination apparatus according to this embodiment is the same as those of the examination apparatus according to the eighth embodiment.

Since the structure of the examination apparatus according to this embodiment is basically the same as that according to the eighth embodiment, the same method of operation as that according to the eighth embodiment can be employed.

Furthermore, the examination apparatus according to this embodiment can be operated by employing a method described below, which is different from that according to the eighth embodiment. Similar to the eighth embodiment, before any of the following operations, the light-emitting unit 216 for externally emitting illumination light or excitation light is guided into the living organism, organ, or tissue, and the illumination light or excitation light is emitted from the light-emitting unit 216 so as to internally illuminate the living organism, organ, or tissue.

As one method, for example, an image-capturing device 230 captures a transmission image and a fluorescence image; an image-processing unit 250 produces a transmission image and a fluorescence image, and a display device 240 adjacently displays the transmission image and the fluorescence image, as an image 243 and an image 244, as illustrated in FIG. 37. In other words, a transmission image and a fluorescence image are obtained by capturing an external image of a living organism, organ, or tissue, and the transmission image and the fluorescence image are adjacently displayed on the display device 240. By comparing the fluorescence image and the transmission image, the site where fluorescence is generated can be specified. Moreover, the position (distribution), amount, and area of the fluorescent substance in the living organism, organ, or tissue can be studied and confirmed on the basis of a transmission image and a fluorescence image by obtaining a transmission image and a fluorescence image by capturing an external image of the living organism, organ, or tissue.

Moreover, the image-capturing device 230 captures a transmission image and a fluorescence image, the image-processing unit 250 produces a fluorescence image and a differential image of a transmission image, and the display device 240 displays the fluorescence image and the differential image of the transmission image, as an image 243 and an image 244 adjacent to each other, as illustrated in FIG. 37. In other words, a transmission image and a fluorescence image are obtained by capturing an external image of a living organism, organ, or tissue, and the fluorescence image and a differential image of the transmission image are displayed adjacent to each other on the display device 240. By comparing the fluorescence image and the differential image of the transmission image, the site where fluorescence is generated can be specified. Moreover, the position (distribution), amount, and area of the fluorescent substance in the living organism, organ, or tissue can be studied and confirmed on the basis of a fluorescence image and a differential image of a transmission image by obtaining a transmission image and a fluorescence image by capturing an external image of the living organism, organ, or tissue.

As described in the eighth embodiment, a differential image is displayed by changing the contrast of the diffused light generated by the refractive-index distribution of the living organism, organ, or tissue, making it easy to recognize the shape of the living organism, organ, or tissue. Therefore, the fluorescence-generating site can be specified even more easily when a comparison is carried out using a differential image of a fluorescence image or a differential image of a transmission image.

Figure 38:
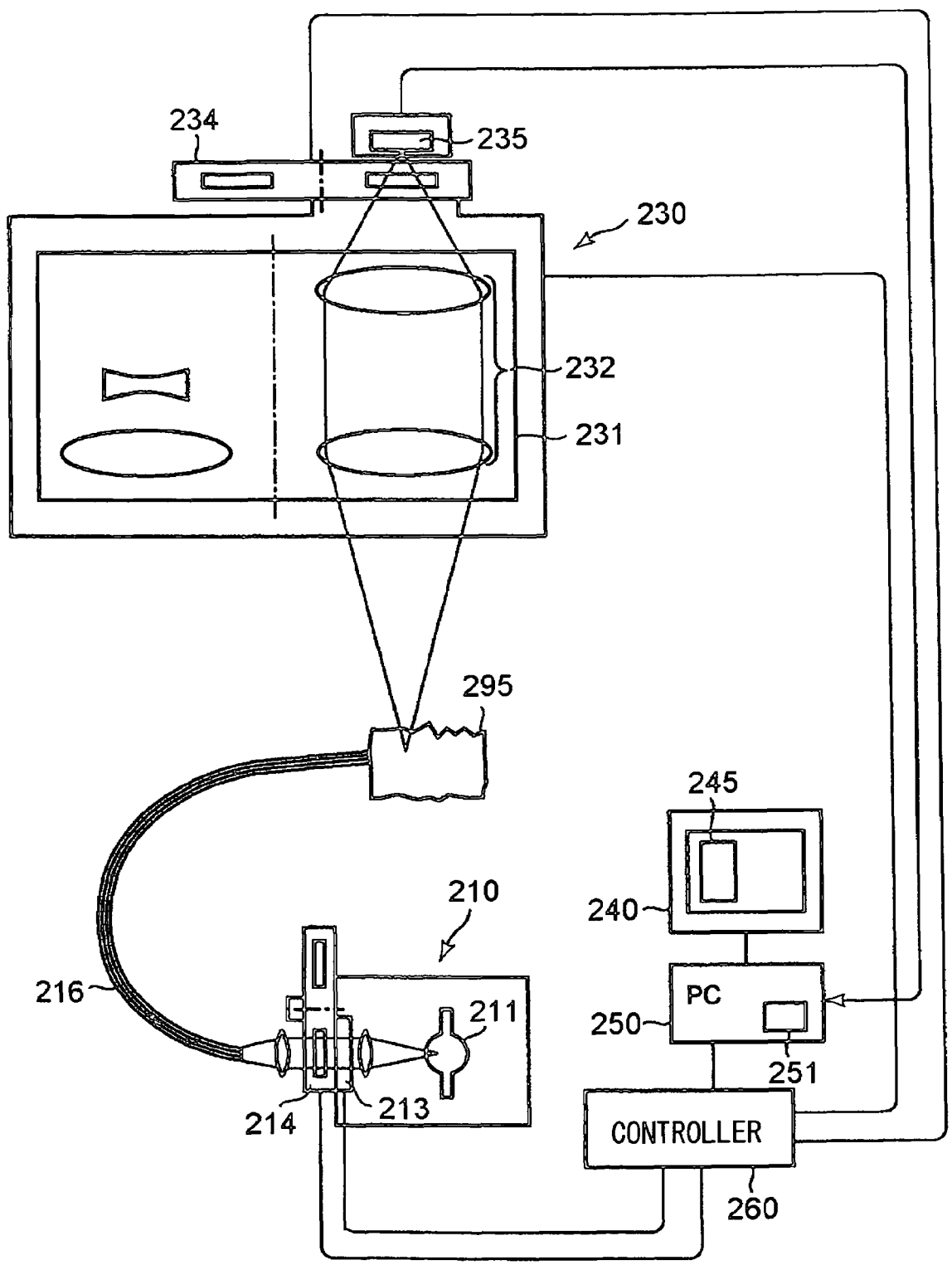
FIG. 38 is a schematic view of the structure of an examination apparatus according to a tenth embodiment of the present invention.

As another method, for example, the image-capturing device 230 captures a transmission image and a fluorescence image, the image-processing unit 250 produces an overlapping image of the transmission image and the fluorescence image, and the display device 240 displays an overlapping image of the transmission image and the fluorescence image as an image 245, as illustrated in FIG. 38. In other words, a transmission image and a fluorescence image are obtained by capturing an external image of the living organism, organ, or tissue, and an overlapping image of the transmission image and the fluorescence image is displayed on the display device 240. The site where fluorescence is generated can be specified on the basis of the overlapping image of the transmission image and the fluorescence image. Moreover, the position (distribution), amount, and area of the fluorescent substance in the living organism, organ, or tissue can be studied and confirmed on the basis of the overlapping image of the transmission image and the fluorescence image by obtaining a transmission image and a fluorescence image by capturing an external image of the living organism, organ, or tissue.

Moreover, the image-capturing device 230 captures a fluorescence image, the image-processing unit 250 produces an overlapping image of the fluorescence image and a differential image of the fluorescence image, and the display device 240 displays the overlapping image of the fluorescence image and the differential image of the fluorescence image as an image 245, as illustrated in FIG. 38. In other words, a fluorescence image and a differential image of the fluorescence image are obtained by capturing an external image of the living organism, organ, or tissue, and the overlapping image of the fluorescence image and the differential image of the fluorescence image is displayed on the display device 240. The site where fluorescence is generated can be specified on the basis of the overlapping image of the fluorescence image and the differential image of the fluorescence image. Moreover, the position (distribution), amount, and area of the fluorescent substance in the living organism, organ, or tissue can be studied and confirmed on the basis of the overlapping image of the fluorescence image and the differential image of the fluorescence image by obtaining a fluorescence image by capturing an external image of the living organism, organ, or tissue.

Moreover, the image-capturing device 230 captures a transmission image and a fluorescence image, the image-processing unit 250 produces an overlapping image of the fluorescence image and a differential image of the transmission image, and the display device 240 displays the overlapping image of the fluorescence image and the differential image of the transmission image as the image 245, as illustrated in FIG. 38. In other words, a fluorescence image and a transmission image are obtained by capturing an external image of the living organism, organ, or tissue, and the overlapping image of the fluorescence image and the differential image of the transmission image is displayed on the display device 240. The site where fluorescence is generated can be specified on the basis of the overlapping image of the fluorescence image and the differential image of the transmission image. Moreover, the position (distribution), amount, and area of the fluorescent substance in the living organism, organ, or tissue can be studied and confirmed on the basis of the overlapping image of the fluorescence image and the differential image of the transmission image by obtaining a transmission image and a fluorescence image by capturing an external image of the living organism, organ, or tissue.

Tenth Embodiment

This embodiment is directed to another examination apparatus. FIG. 38 is a schematic view illustrating the structure of an examination apparatus according to a tenth embodiment of the present invention. The examination apparatus according to this embodiment is similar to that according to the eighth embodiment illustrated in FIG. 38. The components illustrated in FIG. 38 that are represented by the same reference numerals as the components illustrated in FIG. 34 are same components, and detailed descriptions thereof are omitted.

As illustrated in FIG. 38, a living organism, organ, or tissue according to this embodiment is a piece of fresh cow liver tissue 295 that has just been cut off. A light-emitting unit 216 constituted of a fiber bundle is pressed against the cow liver tissue 295. The examination apparatus according to this embodiment differs from that according to the eighth embodiment in that an illumination optical system for externally illuminating the living organism, organ, or tissue is not included. The remaining structure of the examination apparatus according to this embodiment is the same as the structure of the examination apparatus according to the eighth embodiment.

Figure 39:
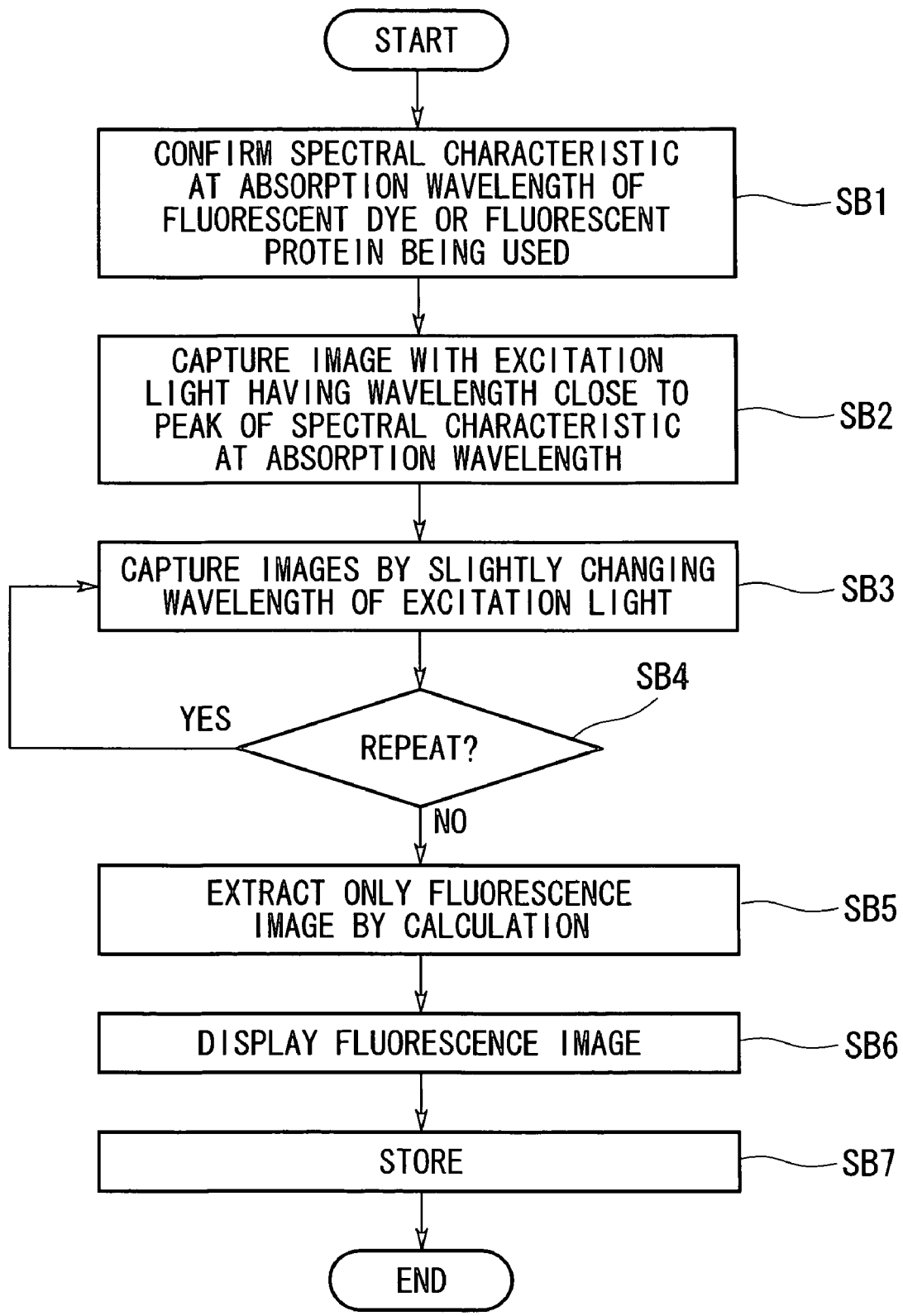
FIG. 39 is a flow chart of an examination process of the examination apparatus according to this embodiment.

FIG. 39 is a flow chart illustrating the examination process carried out by the examination apparatus according to this embodiment. The examination process according FIG. 39 carried out by the examination apparatus according to this embodiment will be described below.

In advance, a plurality of filters having different transmission wavelength bands is installed in the illumination-light filter turret 214 so that a living organism, organ, or tissue can be internally illuminated with various types of excitation light having different wavelength by switching the filters to be disposed in the optical path using the illumination-light filter turret 214.

The excitation wavelength of the (one or more) fluorescent dyes or the (one or more) fluorescent proteins used in the living organism, organ, or tissue, i.e., the cow liver tissue 295, is determined (SB1). The spectroscopic characteristic data of the absorption wavelength of the fluorescent dye or the fluorescent protein is stored in the examination apparatus (for example, a hard disk in the image-processing unit 250) in advance, or, if a site dyed only with a specific fluorescent substance, i.e., the fluorescent dye or the fluorescent protein, is known in advance, the site can be actually measured.

Next, the living organism, organ, or tissue, i.e., the cow liver tissue 295, is excited with excitation light having a wavelength similar to the peak of the determined spectroscopic characteristic of the absorption wavelength of the fluorescent dye or the fluorescent protein so as to capture a fluorescence image with the external image-capturing device 230 the living organism, organ, or tissue, i.e., the cow liver tissue 295 (SB2).

The filter of the illumination-light filter turret 214 is switched to excite the living organism, organ, or tissue, i.e., the cow liver tissue 295, with another excitation beam having a different wavelength similar to the peak of the determined spectroscopic characteristic of the absorption wavelength of another fluorescent dye or another fluorescent protein, and another fluorescence image is captured with the image-capturing device 230 (SB3). In other words, an excitation beam having a different wavelength is used for excitation and for obtaining a different fluorescence image.

If required, step SB3 (changing the wavelength of the excitation beam and capturing an image) is repeated (SB4).

A true fluorescence image is obtained by calculation based on the image data for the plurality of fluorescence images obtained (SB5). The true fluorescence image is obtained by comparing the actual measurement data with the spectroscopic data of the absorption wavelength for each fluorescent substance being used and separating (identifying) the fluorescence for each fluorescent substance. The true fluorescence image obtained this way will have fewer errors in brightness as the number of fluorescence images obtained and used for calculation increases, but, at the same time, photobleaching of the fluorescent dye or the fluorescent protein increases.

The obtained true fluorescence image is displayed on the display device 240 (SB6).

If required, the obtained true fluorescence image is stored in the image-recording unit 251 of the image-processing unit 250 (SB7).

By carrying out such processing, a plurality of true fluorescence images corresponding to the fluorescent substances can be obtained. A true fluorescence image of a specific fluorescent substance can be obtained by determining, in advance, the spectral characteristic of the absorption wavelength of autofluorescence and separating the autofluorescence by carrying out a process similar to the process of separating the fluorescence for each fluorescent substance.

As described above, with this embodiment, for example, the illumination device 210 internally illuminates a living organism, organ, or tissue with various types of excitation beams having different wavelengths, and the image-processing unit 250 separates a plurality of fluorescence beams corresponding to the types of excitation beams on the basis of image signals of the plurality of fluorescence images captured by the image-capturing device 230. More specifically, a plurality of fluorescence images are obtained by internally illuminating the living organism, organ, or tissue with various types of excitation beams having different wavelengths and separating a plurality of fluorescence beams corresponding to different types of excitation beams on the basis of the plurality of fluorescence images obtained by capturing external images of the living organism, organ, or tissue. In this way, a plurality of optimal fluorescence images (true fluorescence images) with the unwanted fluorescence components being removed can be obtained. Furthermore, based on this, the position (distribution), the amount, and area of the fluorescent substance in the living organism, organ, or tissue can be studied and confirmed.

The illumination device 210 internally illuminates a living organism, organ, or tissue with various types of excitation beams having different wavelengths, and the image-processing device 250 produces at least one fluorescence image of the living organism, organ, or tissue by separating autofluorescence of the living organism, organ, or tissue on the basis of image signals of the plurality of fluorescence images captured by the image-capturing device 230. More specifically, at least one fluorescence image of the living organism, organ, or tissue is obtained by internally illuminating the living organism, organ, or tissue with a various types of excitation light having different wavelength and separating autofluorescence of the living organism, organ, or tissue on the basis of the plurality of fluorescence images obtained by capturing external images of the living organism, organ, or tissue. In this way, an optimal fluorescence image (true fluorescence image) with the autofluorescence component being removed can be obtained. Furthermore, based on this, the position (distribution), amount, and area of the fluorescent substance in the living organism, organ, or tissue can be studied and confirmed.

Figure 40:
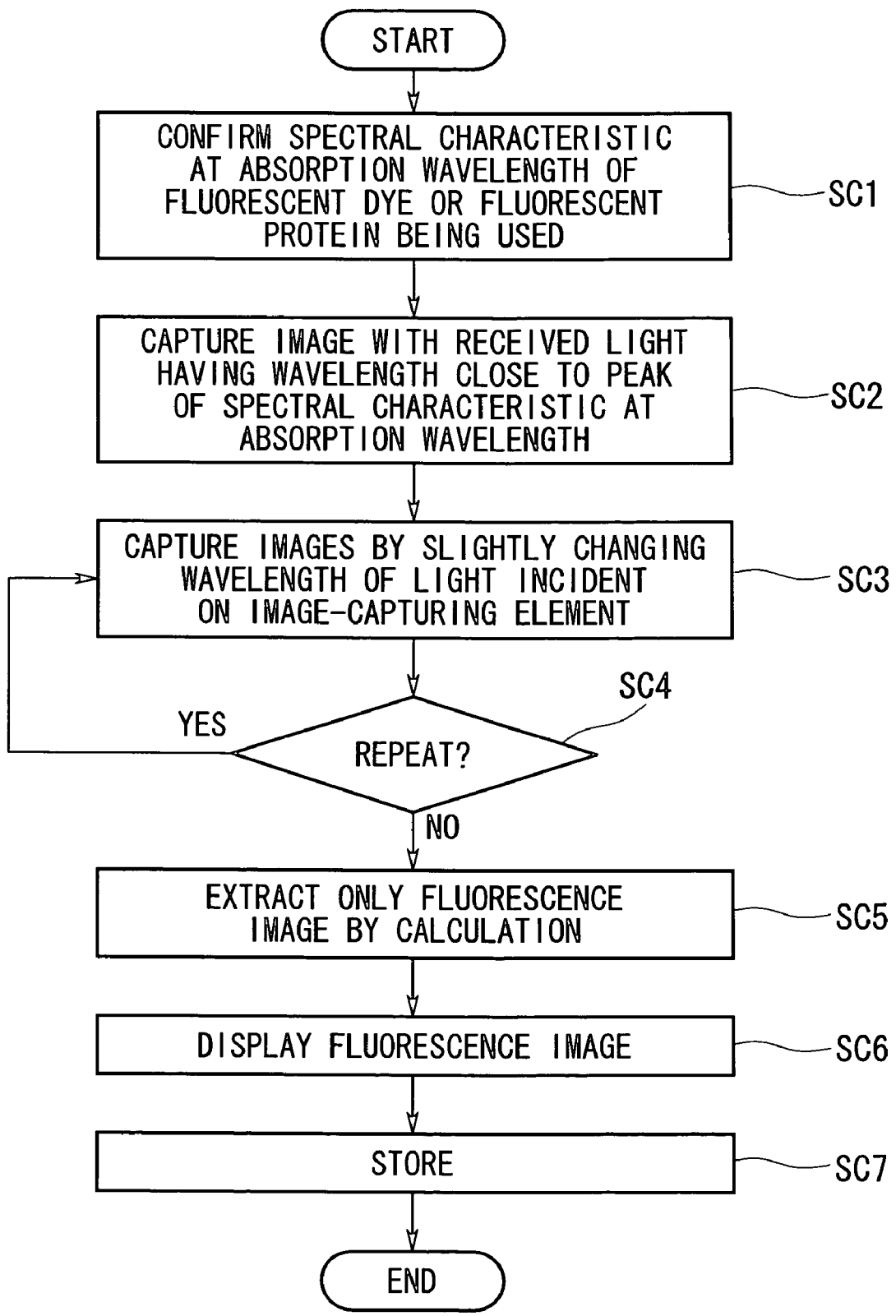
FIG. 40 is a flow chart of another examination process of the examination apparatus according to this embodiment.

FIG. 40 is another flow chart illustrating the examination process carried out by the examination apparatus according to this embodiment. The examination process according FIG. 40 carried out by the examination apparatus according to this embodiment will be described below.

In advance, a plurality of filters having different transmission wavelength bands is installed in the light-reception filter turret 234 so that a plurality of fluorescence images having different wavelengths can be selectively captured by switching the filters disposed in the optical path using the light-reception filter turret 234.

The excitation wavelength of the (one or more) fluorescent dyes or the (one or more) fluorescent proteins used in the living organism, organ, or tissue, i.e., the cow liver tissue 295, is determined (SC1). The spectroscopic characteristic of the fluorescence wavelength of the fluorescent dye or the fluorescent protein is stored in the examination apparatus (for example, a hard disk in the image-processing unit 250) in advance, or, if a site dyed only with a specific fluorescent substance, i.e., the fluorescent dye or the fluorescent protein, is known in advance, the site can be actually measured.

Next, the living organism, organ, or tissue, i.e., the cow liver tissue 295, is excited with an excitation beam having a specific wavelength, and a fluorescence image is captured by the image-capturing device 230 disposed outside the living organism, organ, or tissue, i.e., the cow liver tissue 295, through a filter having a transmission wavelength band similar to the peak of the spectroscopic characteristic of the fluorescence wavelength of the determined fluorescent dye or fluorescent protein (SC2).

The filter of the light-reception filter turret 234 is switched to capture another fluorescence image with the image-capturing device 230 through another filter having a transmission wavelength band similar to the peak of the spectroscopic characteristic of the fluorescence wavelength of the determined fluorescent dye or fluorescent protein (SC3). In other words, the wavelength of the light incident on the image-capturing element 235 is changed to obtain another fluorescence image.

If required, step SC3 (changing the wavelength of the light incident on the image-capturing element 235 and capturing an image) is repeated (SC4).

A true fluorescence image is obtained by calculation based on the image data for the plurality of fluorescence images obtained (SC5). The true fluorescence image is obtained by comparing the actual measurement data with the spectroscopic data of the fluorescent wavelength for each fluorescent substance being used and separating (identifying) the fluorescence for each fluorescent substance. The true fluorescence image obtained this way will have fewer errors in brightness as the number of fluorescence images obtained and used for calculation increases, but, at the same time, photobleaching of the fluorescent dye or the fluorescent protein increases.

The obtained true fluorescence image is displayed on the display device 240 (SC6).

If required, the obtained true fluorescence image is stored in the image-recording unit 251 of the image-processing unit 250 (SC7).

By carrying out such processing, a plurality of true fluorescence images corresponding to the fluorescent substances can be obtained. A specific true fluorescence image of a specific fluorescent substance can be obtained by determining the spectral characteristic of the absorption wavelength of autofluorescence in advance and separating the autofluorescence by carrying out a process similar to the process of separating the fluorescence for each fluorescent substance.

As described above, with this embodiment, for example, the illumination device 210 internally illuminates a living organism, organ, or tissue with an excitation beam having a specific wavelength; the image-capturing device 230 captures images in different wavelength bands; and the image-processing unit 250 separates at least two fluorescence components corresponding to at least two fluorescent substances on the basis of image signals of the plurality of fluorescence images captured by the image-capturing device 230 and produces at least two fluorescence images of the living organism, organ, or tissue. More specifically, at least two fluorescence images of the living organism, organ, or tissue are obtained by internally illuminating the living organism, organ, or tissue with an excitation beam having a specific wavelength and separating at least two fluorescence components corresponding to at least two fluorescent substances on the basis of the plurality of fluorescence images obtained by capturing external images of the living organism, organ, or tissue through a plurality of filters having different transmission wavelength bands. In this way, a plurality of optimal fluorescence images (true fluorescence images) with the unwanted fluorescence components being removed can be obtained. Furthermore, based on this, the position (distribution), the amount, and/or the area of the fluorescent substances in the living organism, organ, or tissue can be studied and/or confirmed.

Furthermore, the illumination device 210 internally illuminates a living organism, organ, or tissue with an excitation beam having a specific wavelength; the image-capturing device 230 captures images in different wavelength bands; and the image-processing unit 250 separates autofluorescence of the living organism, organ, or tissue on the basis of image signals of the plurality of fluorescence images captured by the image-capturing device 230 and produces at least one fluorescence image of the living organism, organ, or tissue. More specifically, at least one fluorescence image of the living organism, organ, or tissue is obtained by internally illuminating the living organism, organ, or tissue with an excitation beam having a specific wavelength and separating the autofluorescence of the living organism, organ, or tissue on the basis of the plurality of fluorescence images obtained by capturing external images of the living organism, organ, or tissue through a plurality of filters having different transmission wavelength bands. In this way, an optimal fluorescence image (true fluorescence image) with the autofluorescence components being removed can be obtained. Furthermore, based on this, the position (distribution), amount, and area of the fluorescent substance in the living organism, organ, or tissue can be studied and confirmed.

Eleventh Embodiment

Figure 41:
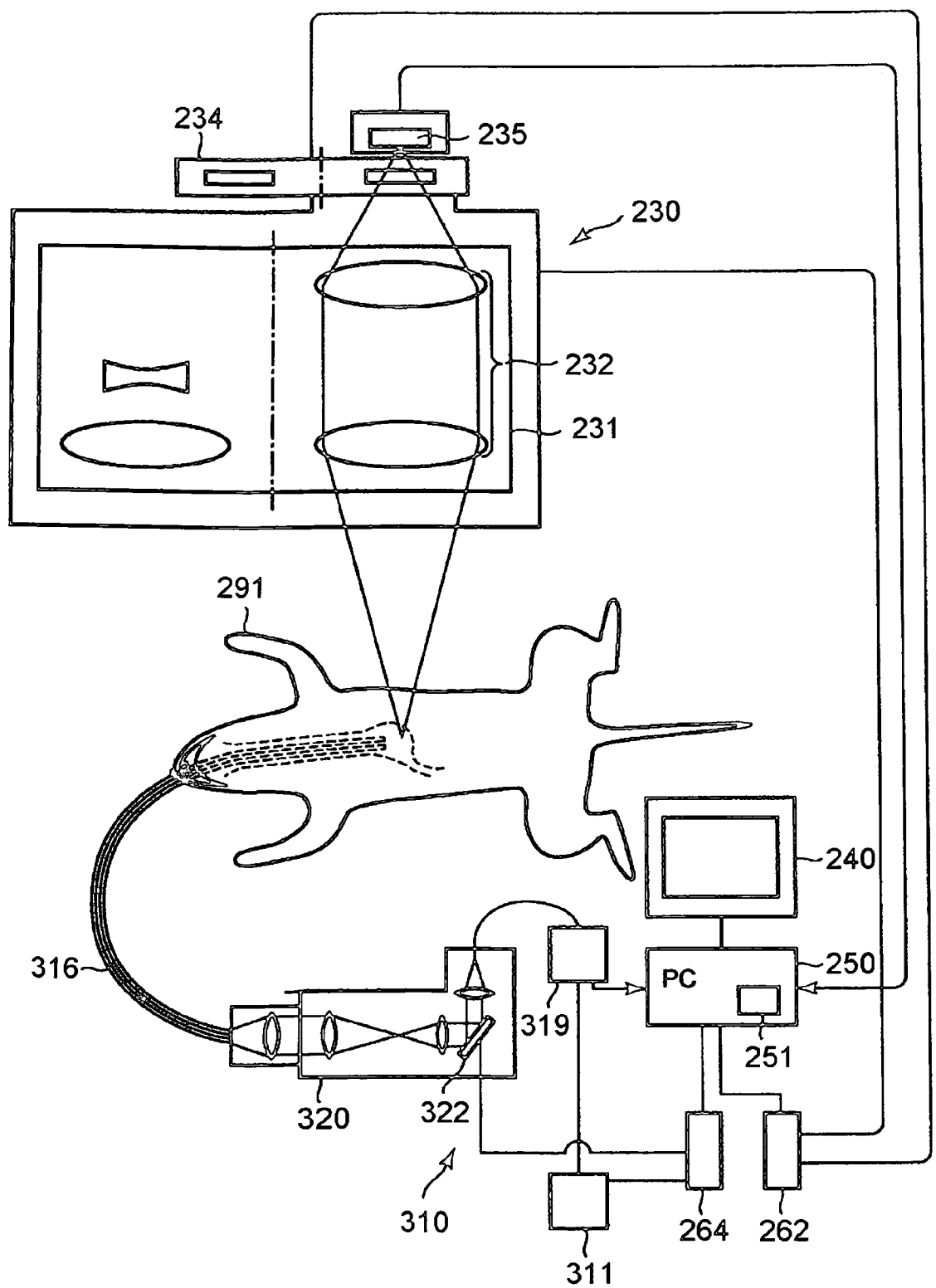
FIG. 41 is a schematic view of the structure of an examination apparatus according to an eleventh embodiment of the present invention.

This embodiment is directed to another examination apparatus. FIG. 41 is a schematic view illustrating the structure of an examination apparatus according to an eleventh embodiment of the present invention. The examination apparatus according to this embodiment is similar to that according to the eighth embodiment illustrated in FIG. 34. The components illustrated in FIG. 41 that are represented by the same reference numerals as the components illustrated in FIG. 34 are the same components, and detailed descriptions thereof are omitted.

Instead of the illumination device 210 according to the eighth embodiment, the examination apparatus according to this embodiment includes another illumination device 310, as illustrated in FIG. 41. The illumination device 310 includes a laser combiner 311 to which a plurality of lasers generating an illumination beam or excitation beam can be attached, a light-emitting unit 316 that can be guided into a living organism, organ, or tissue, a biological endoscope device 320 for guiding the illumination beam or the excitation beam to the light-emitting unit 316 and for producing an image by receiving light from the light-emitting unit 316, and a light-receiving unit 319 including an image-capturing element for photoelectrically converting the optical image produced by the biological endoscope device 320.

An argon laser, a helium ion laser, a laser diode, or the like can be attached on the laser combiner 311. The biological endoscope device 320 guides the illumination beam or the excitation beam from the laser combiner 311 to the light-emitting unit 316. The light-emitting unit 316 is constituted of, for example, a fiber bundle and emits the illumination beam or the excitation beam supplied from the biological endoscope device 320.

The biological endoscope device 320 includes a confocal scanning optical system for optically examining a living organism, organ, or tissue through the light-emitting unit 316. The confocal scanning optical system includes a galvanometer mirror 322 as a scanning unit and a pinhole provided at a point confocal with the examination surface, i.e., the focal point of the emitted beam. The beam emitted from the light-emitting unit 316 is two-dimensionally scanned by the galvanometer mirror 322 while only light near the examination surface is selectively received through the pinhole to form an image. In this way, a desirable optical image of the examination surface can be obtained without being affected by unwanted light entering the light-emitting unit 316 from sites further away from the examination surface.

The examination apparatus further includes a controller 262 for controlling an image-forming optical system turret 231 and a light-reception filter turret 234, and a controller 264 for controlling the laser combiner 311 and the galvanometer mirror 322.

According to this embodiment, a transmission image or a fluorescence image is obtained by internally illuminating a living organism, organ, or tissue, i.e., mouse 291, by emitting an illumination beam or excitation beam from the light-emitting unit 316 and capturing an external image of the living organism, organ, or tissue, i.e., the mouse 291, with the external image-capturing device 230, and an optical image (reflection image or fluorescence image) is obtained by capturing an internal image of the living organism, organ, or tissue, i.e., the mouse 291, with the biological endoscope device 320. A display device 240 displays an image 246, that is, a transmission image or a fluorescence image obtained by the image-capturing device 230 and an image 247, that is, an optical image obtained by the biological endoscope device 320.

Since the optical image obtained by capturing an internal image of the living organism, organ, or tissue, i.e., mouse 291, is imaged by the confocal optical system, the optical image is substantially unaffected by unwanted light generated by reflection and/or diffusion of the illumination beam or excitation beam emitted from the light-emitting unit 316 at the inner surface of the living organism, organ, or tissue, i.e., mouse 291.

As described above, with this embodiment, the illumination device 310 has a function of internally illuminating a living organism, organ, or tissue and a function of capturing an internal image of the living organism, organ, or tissue. The display device 240 displays an image produced by capturing an external image of the living organism, organ, or tissue and an image produced by capturing an internal image of the living organism, organ, or tissue. More specifically, in addition to an external image of the living organism, organ, or tissue, an internal image of the living organism, organ, or tissue is captured, and the image produced by capturing an external image of the living organism, organ, or tissue and the image produced by capturing an internal image of living organism, the organ, or the tissue are displayed on the display device 240. In this way, the distribution of the target molecules within a wide region of the living organism, organ, or tissue can be easily compared with the distribution of the target molecules in the living organism, the organ, or tissue at tissue level or a cell level. Moreover, the changes over time in the amount and the area of a fluorescent substance can be easily compared and studied by examining the microscopic and macroscopic changes in the amounts and/or the areas of the fluorescent substance in the living organism, organ, or tissue by using a fluorescence image produced by capturing an external image of the living organism, organ, or tissue and a fluorescence image produced by capturing an internal image of the living organism, organ, or tissue.

The examination apparatus according to this embodiment may employ experimental methods known as fluorescence resonance energy transfer (FRET) and bioluminescence resonance energy transfer (BRET), for determining the interaction of biomolecules.

FRET and BRET are methods using "resonance energy transfer (RET)" to detect whether or not two substances (donor and acceptor) are in a state significantly close to each other (or in a bonding state). When the donor is a fluorescent substance, the method is referred to as FRET, and CFP (fluorescent protein) is used as the donor, whereas YFP (fluorescent protein) or a quencher is used as the acceptor. When the donor is a bioluminescence substance, the method is referred to as BRET, and luciferase (bioluminescent substance) is used as the donor, whereas YFP (fluorescent protein) or a quencher is used as the acceptor.

When a substance (acceptor) capable of causing resonance energy transfer to the donor is present near the donor (at a distance where physiological interaction occurs), resonance energy transfer occurs between the two substances, causing the peak of the fluorescent wavelength to shift or the brightness of the fluorescence to change. At this time, the donor and the acceptor are referred to as being bonded (correlated). When the acceptor is not present near the donor, the donor and the acceptor are referred to as not being bonded (not correlated).

By examining the fluorescence image obtained by the examination apparatus according to this embodiment, it can be detected whether or not two substances (donor and acceptor) are in the bonded state. In this way, for example, an examination can be carried out to detect whether a medicine is working by bonding to a diseased area.

More specifically, when the examination apparatus according to this embodiment is applied to FRET or BRET, an illumination device internally illuminates a living organism, organ, or tissue including a first substance, such as a fluorescent dye or a bioluminescent substance, and a second substance that causes resonance energy transfer when bonded with the first substance, and an image-processing unit detects the correlation and/or bonding of molecules in a living organism, organ, or tissue on the basis of an image signal of a fluorescence image captured by an image-capturing device. In other words, the correlation and/or bonding of molecules in a living organism, organ, or tissue is detected on the basis of a fluorescence image obtained by capturing an external image of a living organism, organ, or tissue, including a first substance and a second substance that causes resonance energy transfer when bonded with the first substance. In this way, the molecular reaction in a living organism, organ, or tissue can be visualized.

Twelfth Embodiment

Figure 42:
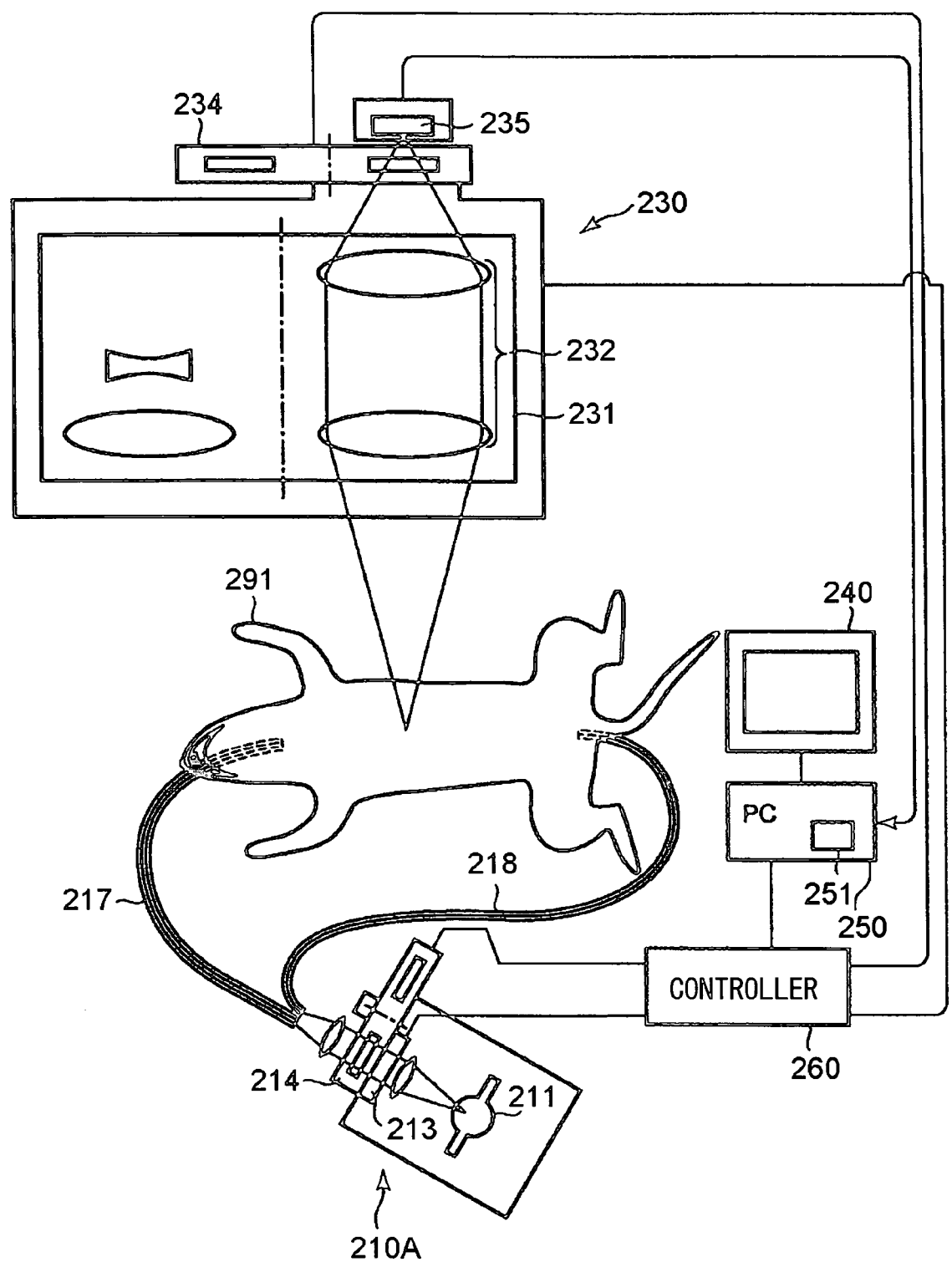
FIG. 42 is a schematic view of the structure of an examination apparatus according to a twelfth embodiment of the present invention.

This embodiment is directed to another examination apparatus. FIG. 42 is a schematic view illustrating the structure of an examination apparatus according to a twelfth embodiment of the present invention. The examination apparatus according to this embodiment is similar to that according to the eighth embodiment illustrated in FIG. 34. The components illustrated in FIG. 42 that are represented by the same reference numerals as the components illustrated in FIG. 34 are same components, and detailed descriptions thereof are omitted.

Instead of the light-emitting unit 216 according to the eighth embodiment, the examination apparatus according to this embodiment includes an illumination device 210A having a plurality of light-emitting units for externally emitting an illumination beam or excitation beam, e.g., two light-emitting units 217 and 218, as shown in FIG. 42. The light-emitting units 217 and 218 can both be guided into a living organism, organ, or tissue. The illumination device 210A, illustrated in FIG. 42, includes two light-emitting units 217 and 218. However, the number of light-emitting units is not limited, and three or more light emitting units may be included.

Similar to the eighth embodiment, the light-emitting units 217 and 218 are constituted of but not limited to, for example, fiber bundles. The living organism, organ, or tissue according to this embodiment is a mouse 291. The light-emitting unit 217 is inserted into the mouse 291 through the mouth, whereas the light-emitting unit 218 is inserted into the mouse 291 through the anus.

Illumination beams or excitation beams are emitted from the two light-emitting units 217 and 218 so as to internally illuminate the mouse 291.

As described above, with this embodiment, a living organism, organ, or tissue is internally illuminated by guiding a plurality of light-emitting units 216 that externally emit illumination beams or excitation beams into the living organism, organ, or tissue. In this way, a wide region of the living organism, organ, or tissue, i.e., mouse 291, can be internally illuminated.

Thirteenth Embodiment

Figure 43:
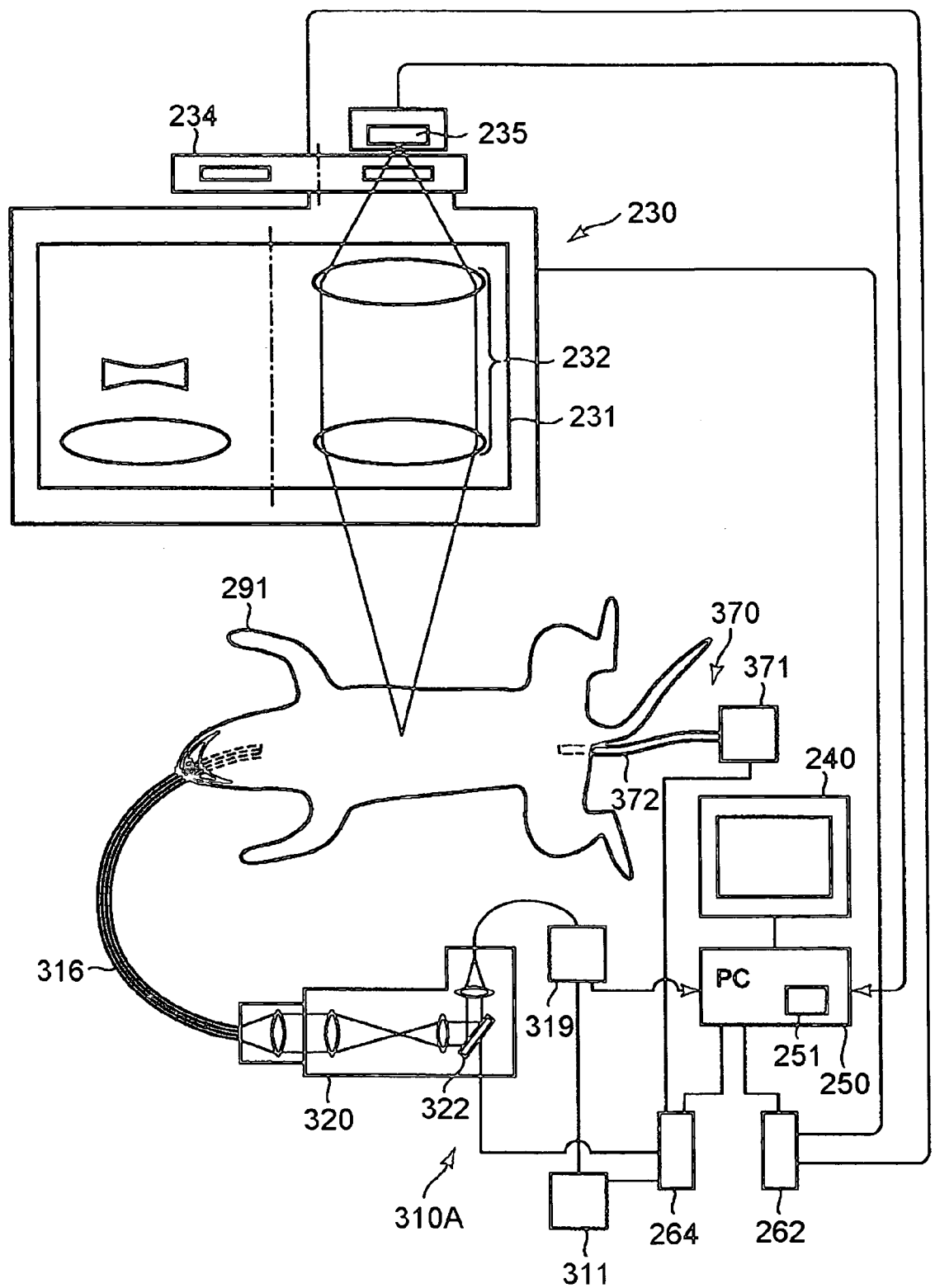
FIG. 43 is a schematic view of the structure of an examination apparatus according to a thirteenth embodiment of the present invention.

This embodiment is directed to another examination apparatus. FIG. 43 is a schematic view illustrating the structure of an examination apparatus according to a thirteenth embodiment of the present invention. The examination apparatus according to this embodiment is similar to that according to the eleventh embodiment illustrated in FIG. 41. The components illustrated in FIG. 43 that are represented by the same reference numerals as the components illustrated in FIG. 41 are the same components, and detailed descriptions thereof are omitted.

In addition to the illumination device 310 according to the eleventh embodiment, the examination apparatus according to this embodiment includes an illumination device 310A having an illumination optical system 370, as shown in FIG. 43. The illumination optical system 370 includes a light source 371 for generating an illumination beam or excitation beam and a light-emitting unit 372 for externally emitting the illumination beam or excitation beam. The light-emitting unit 372 can be guided into a living organism, organ, or tissue.

The light source 371 is constituted of but not limited to, for example, a xenon lamp, a mercury lamp, or a halogen lamp. The light-emitting unit 372 is constituted of but not limited to, for example, a fiber bundle.

More specifically, the illumination device 310A includes a plurality of light-emitting units for externally emitting illumination beams or excitation beams, such as a light-emitting unit 316 and the light-emitting unit 372. The light-emitting unit 316 and the light-emitting unit 372 can both be guided into a living organism, organ, or tissue.

The living organism, organ, or tissue according to this embodiment is a mouse 291. The light-emitting unit 316 of a biological endoscope device 320 is inserted into the mouse 291 through the mouth, whereas the light-emitting unit 372 of the illumination optical system 370 is inserted into the mouse 291 through the anus.

An illumination beam or excitation beam is emitted from the light-emitting unit 316 and the light-emitting unit 372 so as to internally illuminate the mouse 291.

As described above, with this embodiment, a living organism, organ, or tissue is internally illuminated by guiding a plurality of light-emitting units 216 that externally emit an illumination beam or excitation beam into the living organism, organ, or tissue. In this way, a wide region of the living organism, organ, or tissue, i.e., mouse 291, can be internally illuminated.

Fourteenth Embodiment

Figure 44:
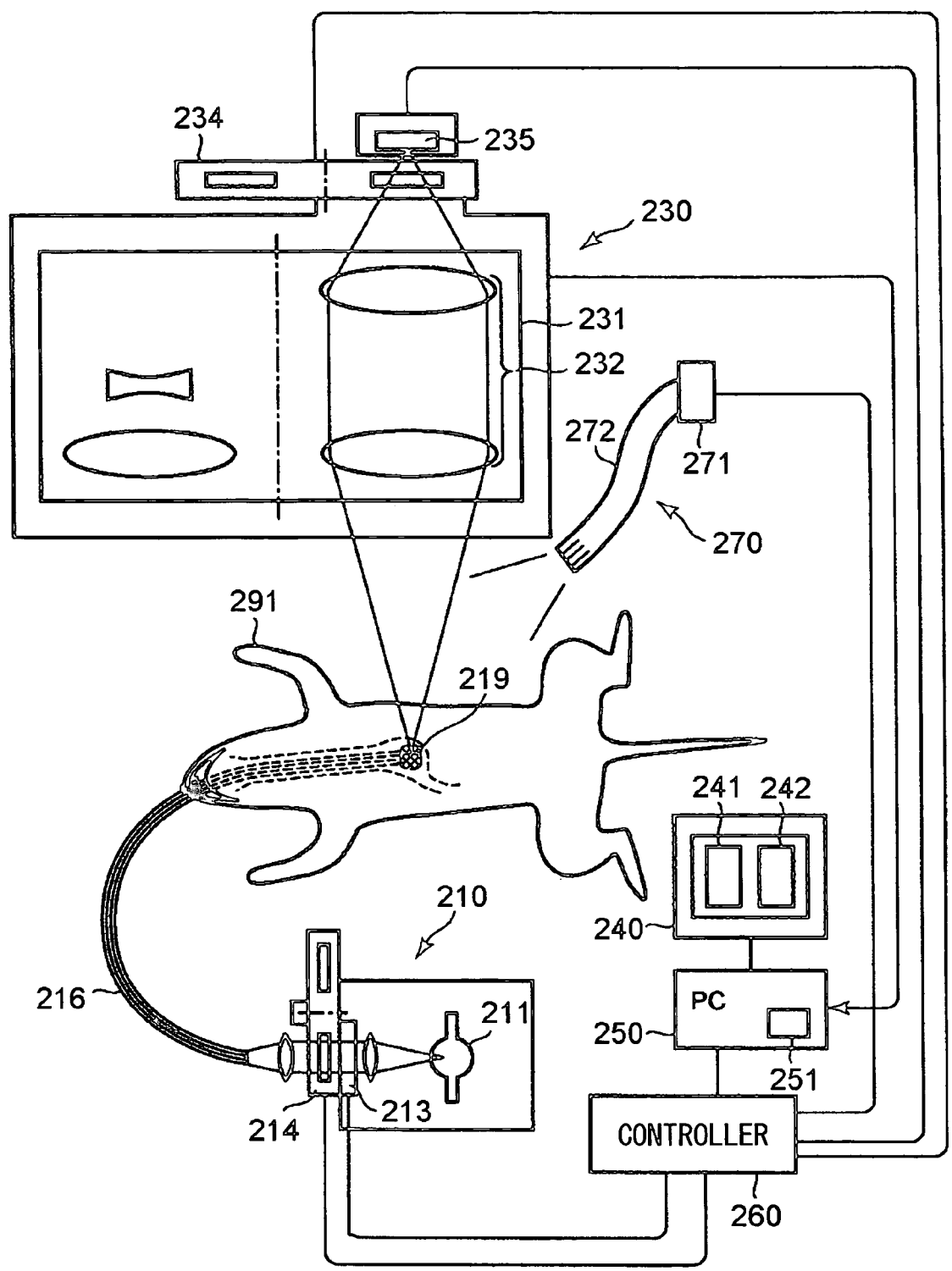
FIG. 44 is a schematic view of the structure of an examination apparatus according to a fourteenth embodiment of the present invention.

This embodiment is directed to another examination apparatus. FIG. 44 is a schematic view illustrating the structure of an examination apparatus according to a fourteenth embodiment of the present invention. The examination apparatus according to this embodiment is similar to that according to the eighth embodiment illustrated in FIG. 34. The components illustrated in FIG. 44 that are represented by the same reference numerals as the components illustrated in FIG. 34 are the same components, and detailed descriptions thereof are omitted.

As illustrated in FIG. 44, in the examination apparatus according to this embodiment, an illumination device 210 further includes a balloon for diffusing light at the tip of a light-emitting unit 216.

In this examination apparatus, an illumination beam or excitation beam emitted from the light-emitting unit 216 is diffused at the balloon and is incident on a living organism, organ, or tissue, i.e., mouse 291.

More specifically, with this embodiment, the illumination beam or excitation beam emitted from the light-emitting unit 216 is diffused for illumination. In this way, a wide region of the living organism, organ, or tissue can be internally illuminated.

The embodiments of the present invention have been described with reference to the drawings. However, the embodiments of the present invention are not limited thereto, and various changes in shape may be made and various modifications may be provided within the scope of the invention.

The present invention is directed to an examination apparatus for examining a living organism, organ, or tissue and includes the examination apparatuses according to the following items.

1. The examination apparatus according to the present invention includes an illumination device for internally illuminating a living organism, organ, or tissue and an image-capturing device for obtaining an optical image i.e., at least one of a transmission image and a fluorescence image, of the living organism, organ, or tissue by capturing an external image of the living organism, organ, or tissue. Here, to "guide" a light-emitting unit into a living organism, organ, or tissue means to insert the light-emitting unit into a cavity in the living organism, organ, or tissue, to puncture the living organism, organ, or tissue with the light-emitting unit, or to press the light-emitting unit 216 against the living organism, organ, or tissue.

With this examination apparatus, the living organism, organ, or tissue is internally illuminated. In this way, the living organism, organ, or tissue can be efficiently illuminated and examined at high resolution.

2. In another examination apparatus of the present invention, in the examination apparatus according to Item 1, the illumination device includes a light source for emitting illumination light or excitation light and a light-emitting unit for externally emitting illumination light or excitation light, wherein the light-emitting unit can be guided into the living organism, organ, or tissue.

In this examination apparatus, the living organism, organ, or tissue is internally illuminated by guiding the light-emitting unit into the living organism, organ, or tissue and emitting illumination light or excitation light from the light-emitting unit.

3. In another examination apparatus of the present invention, in the examination apparatus according to Item 2, the image-capturing device includes an image-forming optical system for imaging the light from a living organism, organ, or tissue and an image-capturing element for generating an image signal by photoelectrically converting the optical image produced by the image-forming optical system. The examination apparatus further includes a display device for displaying an image and an image-processing unit for producing an image to be displayed on the display device by processing the image signal from the image-capturing device.

4. In another examination apparatus of the present invention, in the examination apparatus according to Item 3, the image-processing unit further includes an image-recording unit for recording an image.

5. In another examination apparatus of the present invention, in the examination apparatus according to Item 2, the illumination device further includes a control unit for controlling the emission of illumination light or excitation light from the light-emitting unit.

6. In another examination apparatus of the present invention, in the examination apparatus according to Item 2, the illumination device further includes a switching unit for switching the wavelength of illumination light or excitation light emitted from the light-emitting unit.

With this examination apparatus, a living organism, organ, or tissue can be internally illuminated with excitation light having a wavelength corresponding to a fluorescent protein, such as green florescent protein (GFP), DsRed, RFP, CFP, YFP, or Kaede, or a fluorescent dye, such as FITC, Alexa Fluor 488, Alexa Fluor 647, Alexa Fluor 660, Alexa Fluor 680, Alexa Fluor 700, Alexa Fluor 750, Rhodamine, Texas Red, Cy5, Cy5.5, Cy7, IRDye750, or ICG.

7. In another examination apparatus of the present invention, in the examination apparatus according to Item 3, the illumination device has an image-capturing function for capturing an internal image of a living organism, organ, or tissue.

With this examination apparatus, distribution of target molecules within a wide region of a living organism, organ, or tissue and a high-resolution distribution of target molecules in the living organism, the organ, or tissue at the tissue level or cell level can be confirmed.

8. In another examination apparatus of the present invention, in the examination apparatus according to Item 7, the display device displays an image obtained by capturing an external image of a living organism, organ, or tissue and an image obtained by capturing an internal image of the living organism, organ, or tissue.

With this examination apparatus, distribution of target molecules within a wide region of a living organism, organ, or tissue and the distribution of target molecules in the living organism, the organ, or tissue at the tissue level or cell level can be easily compared.

9. In another examination apparatus of the present invention, in the examination apparatus according to Item 3, the image-capturing device obtains a transmission image and a fluorescence image, the image-processing unit produces a transmission image and a fluorescence image, and the display device displays the transmission image and the fluorescence image adjacent to each other.

With this examination apparatus, a site generating fluorescence can be identified by comparing the fluorescence image and the transmission image.

10. In another examination apparatus of the present invention, in the examination apparatus according to Item 3, the image-capturing device obtains a transmission image and a fluorescence image, the image-processing unit produces an overlapping image of the transmission image and the fluorescence image, and the display device displays the overlapping image of the transmission image and the fluorescence image.

With this examination apparatus, a site generating fluorescence can be identified on the basis of the overlapping image of the transmission image and the fluorescence image.

11. In another examination apparatus of the present invention, in the examination apparatus according to Item 3, the image-capturing device obtains a fluorescence image, the image-processing unit produces a fluorescence image and a differential image of the fluorescence image, and the display device displays the fluorescence image and the differential image of the fluorescence image adjacent to each other.

Since a differential image shows diffused light generated by the refractive-index distribution in a living organism, organ, or tissue converted into contrast, the shape of the living organism, organ, or tissue can be recognized.

With this examination apparatus, a site generating fluorescence can be identified by comparing the fluorescence image and the differential image of the fluorescence image.

12. In another examination apparatus of the present invention, in the examination apparatus according to Item 3, the image-capturing device obtains a fluorescence image, the image-processing unit produces an overlapping image of the fluorescence image and a differential image of the fluorescence image, and the display device displays the overlapping image of the fluorescence image and the differential image of the fluorescence image.

With this examination apparatus, a site generating fluorescence can be identified on the basis of the overlapping image of the fluorescence image and the differential image of the fluorescence image.

13. In another examination apparatus of the present invention, in the examination apparatus according to Item 3, the image-capturing device obtains a transmission image and a fluorescence image, the image-processing unit produces a fluorescence image and a differential image of the transmission image, and the display device displays the fluorescence image and the differential image of the transmission image adjacent to each other.

With this examination apparatus, a site generating fluorescence can be identified by comparing the fluorescence image and the differential image of the transmission image.

14. In another examination apparatus of the present invention, in the examination apparatus according to Item 3, the image-capturing device obtains a transmission image and a fluorescence image, the image-processing unit produces an overlapping image of the fluorescence image and a differential image of the transmission image, and the display device displays the overlapping image of the fluorescence image and the differential image of the transmission image.

With this examination apparatus, a site generating fluorescence can be identified on the basis of the overlapping image of the fluorescence image and the differential image of the transmission image.

15. In another examination apparatus of the present invention, in the examination apparatus according to Item 3, the illumination device includes a switching unit for switching the wavelength of excitation light emitted from the light-emitting unit. The illumination device internally illuminates a living organism, organ, or tissue with various types of excitation light having different wavelengths, and the image-processing unit separates a plurality of fluorescence beams corresponding to the types of excitation light on the basis of image signals of a plurality of fluorescence images captured by the image-capturing device and produces a plurality of fluorescence images.

With this examination apparatus, the distribution and amount of fluorescent substances can be confirmed.

16. In another examination apparatus of the present invention, in the examination apparatus according to Item 3, the illumination device includes a switching unit for switching the wavelength of excitation light emitted from the light-emitting unit. The illumination device internally illuminates a living organism, organ, or tissue with various types of excitation light having different wavelengths, and the image-processing unit separates autofluorescence of the living organism, organ, or tissue on the basis of image signals of a plurality of fluorescence images captured by the image-capturing device and produces at least one fluorescence image.

With this examination apparatus, the distribution and amount of fluorescent substances can be confirmed.

17. In another examination apparatus of the present invention, in the examination apparatus according to Item 3, the illumination device includes a switching unit for switching the wavelength of fluorescence light emitted from the light-emitting unit. The illumination device internally illuminates a living organism, organ, or tissue with excitation light having a specific wavelength, the image-capturing device captures images in different wavelength bands, and the image-processing unit separates at least two fluorescence components corresponding to at least two fluorescent substances on the basis of image signals of a plurality of fluorescence images captured by the image-capturing device and produces at least two fluorescence images of the living organism, organ, or tissue.

With this examination apparatus, the distribution and amount of fluorescent substances can be confirmed.

18. In another examination apparatus of the present invention, in the examination apparatus according to Item 3, the illumination device includes a switching unit for switching the wavelength of the fluorescence incident on the image-capturing element. The illumination device internally illuminates a living organism, organ, or tissue with excitation light having a specific wavelength, the image-capturing device captures images in different wavelength bands, and the image-processing unit separates autofluorescence of the living organism, organ, or tissue on the basis of image signals of a plurality of fluorescence images captured by the image-capturing device and produces at least one fluorescence image of the living organism, organ, or tissue.

With this examination apparatus, the distribution and amount of fluorescent substances can be confirmed.

In another examination apparatus of the present invention, in the examination apparatus according to Item 3, the illumination device internally illuminates a living organism, organ, or tissue that includes a first substance and a second substance that causes resonance energy transfer when bonded with the first substance, and the image-processing unit detects the correlation and the bonding of molecules in the living organism, organ, or tissue on the basis of image signals of fluorescence images captured by the image-capturing device.

With this examination apparatus, by obtaining a fluorescence image by using a substance that causes resonance energy transfer when bonded with a fluorescent substance, the molecular reaction in the living organism, organ, or tissue can be visualized.

20. In another examination apparatus of the present invention, in the examination apparatus according to Item 1, the illumination device includes a plurality of light-emitting units for externally emitting illumination light or excitation light. The light-emitting unit can be guided in to a living organism, organ, or tissue.

With this examination apparatus, a wide region of a living organism, organ, or tissue can be illuminated.

21. In another examination apparatus of the present invention, in the examination apparatus according to Item 2, the illumination device includes a balloon that is disposed at the tip of a light-emitting unit and that diffuses light.

With this examination apparatus, a wide region of the living organism, organ, or tissue is illuminated since the illuminating light or excitation light emitted from the light-emitting unit is diffused at the balloon.

22. In the examination apparatus according to Item 1, "living organism" is a living mammal selected from the group consisting of mouse, rat, rabbit, cat, dog, pig, cow, sheep, goat, horse, monkey, gorilla, chimpanzee, and human.

23. In the examination apparatus according to Item 1, "organ" is an organ selected from the group consisting of brain, lung, liver, spleen, bone marrow, thymus, heart, lymph, blood, bone, cartilage, pancreas, liver, gall bladder, stomach, intestine, testis, ovary, uterus, rectum, nervous system, gland, and blood vessel.

24. In the examination apparatus according to Item 1, "tissue" is a three-dimensional structure of a plurality of cells.

The present invention is directed to an examination method for a living organism, organ, or tissue and includes the examination methods according to the following items.

25. With the examination method according to the present invention, a living organism, organ, or tissue is internally illuminated, and an external image of the living organism, organ, or tissue is captured.

26. In another examination method according to the present invention, a light-emitting unit for externally emitting illumination light or excitation light is guided into a living organism, organ, or tissue, the living organism, organ, or tissue is internally illuminated by emitting illumination light or excitation light from the light-emitting unit, an optical image, that is, at least one of a transmission image and a fluorescence image, of the living organism, organ, or tissue is obtained by capturing an external image of the living organism, organ, or tissue, and the obtained optical image is displayed on a display device.

27. In another examination method of the present invention, in the examination method according to Item 26, the light-emitting unit is inserted into a cavity of a living organism, organ, or tissue.

28. In another examination method of the present invention, in the examination method according to Item 26, the light-emitting unit penetrates a living organism, organ, or tissue.

29. In another examination method of the present invention, in the examination method according to Item 26, the light-emitting unit is pushed against a living organism, organ, or tissue.

30. In another examination method of the present invention, in the examination method according to Item 27, the light-emitting unit is inserted into the mouth, nose, uterine cavity, anus, or ear of a living organism for illumination.

31. In another examination method of the present invention, in the examination method according to Item 26, an internal image of the living organism, organ, or tissue is also obtained, and the image obtained by capturing an external image of the living organism, organ, or tissue, and the image obtained by capturing an internal image of living organism, organ, or tissue are displayed on the display device.

32. In another examination method of the present invention, in the examination method according to Item 26, a transmission image and a fluorescence image are obtained by capturing an external image of a living organism, organ, or tissue, and the transmission image and the fluorescence image are displayed adjacent to each other on the display device.

33. In another examination method of the present invention, in the examination method according to Item 26, a transmission image and a fluorescence image are obtained by capturing an external image of a living organism, organ, or tissue, and an overlapping image of the transmission image and the fluorescence image is displayed on the display device.

34. In another examination method of the present invention, in the examination method according to Item 26, a fluorescence image is obtained by capturing an external image of the living organism, organ, or tissue, and the fluorescence image and a differential image of the fluorescence image are displayed adjacent to each other on the display device.

35. In another examination method of the present invention, in the examination method according to Item 26, a fluorescence image is obtained by capturing an external image of the living organism, organ, or tissue, and an overlapping image of the fluorescence image and a differential image of the fluorescence image is displayed on the display device.

36. In another examination method of the present invention, in the examination method according to Item 26, a transmission image and a fluorescence image are obtained by capturing an external image of the living organism, organ, or tissue, and the fluorescence image and a differential image of the transmission image are displayed adjacent to each other on the display device.

37. In another examination method of the present invention, in the examination method according to Item 26, a transmission image and a fluorescence image are obtained by capturing an external image of the living organism, organ, or tissue, and an overlapping image of the fluorescence image and a differential image of the transmission image is displayed on the display device.

38. In another examination method of the present invention, in the examination method according to Item 26, a living organism, organ, or tissue is internally illuminated with various types of excitation light having different wavelengths, and a plurality of fluorescence images are obtained by separating a plurality of fluorescence components corresponding to the types of excitation light on the basis of the plurality of fluorescence images obtained by capturing external images of the living organism, organ, or tissue.

39. In another examination method of the present invention, in the examination method according to Item 26, a living organism, organ, or tissue is internally illuminated with various types of excitation light having different wavelengths, and at least one fluorescence image is obtained by separating autofluorescence of the living organism, organ, or tissue on the basis of the plurality of fluorescence images obtained by capturing an external image of the living organism, organ, or tissue.

40. In another examination method of the present invention, in the examination method according to Item 26, a living organism, organ, or tissue is internally illuminated with excitation light having a specific wavelength, and at least two fluorescence images of the living organism, organ, or tissue are obtained by separating at least two fluorescence components corresponding to at least two fluorescent substances on the basis of a plurality of fluorescence images obtained by capturing external images of the living organism, organ, or tissue through a plurality of filters having different transmission wavelength bands.

41. In another examination method of the present invention, in the examination method according to Item 26, a living organism, organ, or tissue is internally illuminated with excitation light having a specific wavelength, and at least one fluorescence image of the living organism, organ, or tissue is obtained by separating autofluorescence of the living organism, organ, or tissue on the basis of a plurality of fluorescence images obtained by capturing external images of the living organism, organ, or tissue through a plurality of filters having different transmission wavelength bands.

42. In another examination method of the present invention, in the examination method according to Item 26, the correlation and the bonding of molecules in the living organism, organ, or tissue are detected on the basis of a fluorescence image obtained by capturing an external image of the living organism, organ, or tissue, including a first substance and a second substance that causes resonance energy transfer when bonded with the first substance.

43. In another examination method of the present invention, in the examination method according to Item 25, a plurality of light-emitting units for externally emitting illumination light or excitation light is inserted in a living organism, organ, or tissue to internally illuminate the living organism, organ, or tissue.

44. In another examination method of the present invention, in the examination method according to Item 26, illumination light or excitation light emitted from the light-emitting unit is diffused for illumination.

45. In the examination method according to Item 25, "living organism" is a living mammal selected from the group consisting of mouse, rat, rabbit, cat, dog, pig, cow, sheep, goat, horse, monkey, gorilla, chimpanzee, and human.

46. In another examination method of the present invention, in the examination method according to Item 25, "organ" is an organ selected from the group consisting of brain, lung, liver, spleen, bone marrow, thymus, heart, lymph, blood, bone, cartilage, pancreas, liver, gall bladder, stomach, intestine, testis, ovary, uterus, rectum, nervous system, gland, and blood vessel.

47. In another examination method of the present invention, in the examination method according to Item 25, "tissue" is a three-dimensional structure of a plurality of cells.

The present invention is directed to an experimental method using a living organism, organ, or tissue and includes the experimental methods according to the following items.

48. In the experimental method according to the present invention, a light-emitting unit for externally emitting illumination light or excitation light is guided into a living organism, organ, or tissue; the living organism, organ, or tissue is internally illuminated by emitting illumination light or excitation light from the light-emitting unit; a fluorescence image of the living organism, organ, or tissue is obtained by capturing an external image of the living organism, organ, or tissue; and the changes over time in the amount and area of fluorescent substances in the living organism, organ, or tissue are compared and studied by comparing the obtained fluorescence image with other images.

49. In the experimental method of the present invention, in the examination method according to Item 48, the changes over time in the amount and area of fluorescent substances are compared and studied by further obtaining a fluorescence image of the living organism, organ, or tissue by capturing an internal image of the living organism, organ, or tissue, and examining the microscopic and macroscopic changes in the amount and area of fluorescent substances in the living organism, organ, or tissue by using the fluorescence image obtained by capturing an external image of the living organism, organ, or tissue and the fluorescence image obtained by capturing an internal image of the living organism, organ, or tissue.

50. In the experimental method of the present invention, in the examination method according to Item 48, a transmission image and a fluorescence image are obtained by capturing an external image of a living organism, organ, or tissue, and the position, amount, and area of fluorescent substances in the living organism, organ, or tissue are studied on the basis of the transmission image and the fluorescence image.

51. In the experimental method of the present invention, in the examination method according to Item 48, a transmission image and a fluorescence image are obtained by capturing an external image of a living organism, organ, or tissue, and the position, amount, and area of fluorescent substances in the living organism, organ, or tissue are studied on the basis of an overlapping image of the transmission image and the fluorescence image.

52. In the experimental method of the present invention, in the examination method according to Item 48, a fluorescence image is obtained by capturing an external image of a living organism, organ, or tissue, and the position, amount, and area of fluorescent substances in the living organism, organ, or tissue are studied on the basis of the fluorescence image and a differential image of the fluorescence image.

53. In the experimental method of the present invention, in the examination method according to Item 48, a fluorescence image is obtained by capturing an external image of a living organism, organ, or tissue, and the position, amount, and area of fluorescent substances in the living organism, organ, or tissue are studied on the basis an overlapping image of the fluorescence image and a differential image of the fluorescence image.

54. In the experimental method of the present invention, in the examination method according to Item 48, a transmission image and a fluorescence image are obtained by capturing an external image of a living organism, organ, or tissue, and the position, amount, and area of fluorescent substances in the living organism, organ, or tissue are studied on the basis of the fluorescence image and a differential image of the transmission image.

55. In the experimental method of the present invention, in the examination method according to Item 48, a transmission image and a fluorescence image are obtained by capturing an external image of a living organism, organ, or tissue, and the position, amount, and area of fluorescent substances in the living organism, organ, or tissue are studied on the basis of an overlapping image of the fluorescence image and a differential image of the transmission image.

56. In the experimental method of the present invention, in the examination method according to Item 48, the position, amount, and area of fluorescent substances in a living organism, organ, or tissue are studied by internally illuminating the living organism, organ, or tissue with various types of excitation light having different wavelengths, and by obtaining a plurality of fluorescence images by separating a plurality of fluorescence components corresponding to the types of excitation light on the basis of the plurality of fluorescence images obtained by capturing external images of the living organism, organ, or tissue.

57. In the experimental method of the present invention, in the examination method according to Item 48, the position, amount, and area of fluorescent substances in a living organism, organ, or tissue are studied by internally illuminating the living organism, organ, or tissue with various types of excitation light having different wavelengths, and by obtaining at least one fluorescence image of the living organism, organ, or tissue by separating autofluorescence of the living organism, organ, or tissue on the basis of a plurality of fluorescence images obtained by capturing external images of the living organism, organ, or tissue.

58. In the experimental method of the present invention, in the examination method according to Item 48, the position, amount, and area of fluorescent substances in a living organism, organ, or tissue are studied by internally illuminating the living organism, organ, or tissue with excitation light having a specific wavelength, by obtaining at least two fluorescence images of the living organism, organ, or tissue by separating at least two fluorescence components corresponding to the at least two fluorescent substances on the basis of a plurality of fluorescence images obtained by capturing external images of the living organism, organ, or tissue through a plurality of filters having different transmission wavelength bands.

59. In the experimental method of the present invention, in the examination method according to Item 48, the position, amount, and area of fluorescent substances in a living organism, organ, or tissue are studied by internally illuminating the living organism, organ, or tissue with excitation light having a specific wavelength, and by obtaining at least one fluorescence image of the living organism, organ, or tissue by separating autofluorescence of the living organism, organ, or tissue on the basis of a plurality of fluorescence images obtained by capturing external images of the living organism, organ, or tissue through a plurality of filters having different transmission wavelength bands.

The invention claimed is:

1. An examination apparatus comprising:
a light source for emitting excitation light or illumination light to a specimen placed on a stage;
an objective lens opposing the stage and capable of focusing fluorescence or reflected light from the specimen;
an image forming lens for forming an image of the specimen obtained by the objective lens;
an image-capturing unit for capturing the image of the specimen formed by the image-forming lens;
a relay optical system for relaying illumination light for illuminating the specimen; and
a reflecting member held by the image-forming lens, the reflecting member being capable of deflecting the illumination light from the light source toward the relay optical system,
wherein a plurality of the objective lenses having different magnifying powers is provided, and an objective-lens switching mechanism for switching among the objective lenses is provided, and
wherein a plurality of the image-forming lenses having different magnifying powers is provided an image-forming-lens switching mechanism for switching among the image-forming lenses is provided.

2. The examination apparatus according to claim 1, wherein the relay optical system is held by the objective lens or the objective-lens switching mechanism.

3. The examination apparatus according to claim 1, wherein the relay optical system splits the illumination light from the light source into two or more beams and emits the two or more beams to the specimen from different directions.

4. An examination apparatus comprising:
a light source for emitting excitation light or illumination light to a specimen placed on a stage;
an objective lens opposing the stage and capable of focusing fluorescence or reflected light from the specimen;
an image-forming lens for forming an image of the specimen obtained by the objective lens;
an image-capturing unit for capturing the image of the specimen formed by the image-forming lens;
a relay optical system for relaying illumination light for illuminating the specimen; and
a rotary turret for holding a plurality of dichroic mirrors and a reflecting member which deflect, the illumination light from the light source toward the relay optical system and for selectively disposing the dichroic mirrors and the reflecting member opposite the light source,
wherein a plurality of the objective lenses having different magnifying powers is provided and an objective-lens switching mechanism for switching among the objective lenses is provided, and wherein a plurality of the image-forming lenses having different magnifying powers is provided, and an image-forming-lens switching mechanism for switching among the image-forming lenses is provided.

5. An examination apparatus comprising:
a light source for emitting excitation light or illumination light to a specimen placed on a stage;
an objective lens opposing the stage and capable of focusing fluorescence or reflected light from the specimen;
an image forming lens for forming an image of the specimen obtained by the objective lens;
an image-capturing unit for capturing the image of the specimen formed by the image-forming lens; and
a zooming mechanism inserted, on an optical axis, and between an objective lens having a high magnifying power and an image-forming lens having a high magnifying power, when an objective lens having a high magnifying power and an image-forming lens having a high magnifying power are selected,
wherein a plurality of the objective lenses having different magnifying powers is provided, and an objective-lens switching mechanism for switching among the objective lenses is provided, and
wherein a plurality of the image-forming lenses having different magnifying power is provided, and an image-forming-lens switching mechanism for switching among the image-forming lenses is provided.

6. The examination apparatus according to claim 5, wherein the zooming mechanism is provided in a manner such that the zooming mechanism is removable from the optical axis when an objective lens having a low magnifying power and an image-forming lens having a low magnifying power are selected.

7. An examination apparatus comprising:
a light source for emitting excitation light or illumination light to a specimen placed on a stage;
an objective lens opposing the stage and capable of focusing fluorescence or reflected light from the specimen;
an image-forming lens for forming an image of the specimen obtained by the objective lens;
an image-capturing unit for capturing the image of the specimen formed by the image-forming lens; and
a parfocal adjustment mechanism for adjusting the image location of the image-forming lens,
wherein a plurality of the objective lenses having different magnifying powers is provided, and an objective-lens switching mechanism for switching among the objective lenses is provided, and
wherein a plurality of the image-forming lenses having different magnifying powers is provided, and an image-forming-lens switching mechanism for switching among the image-forming lenses is provided.

8. An examination apparatus comprising:
a light source for emitting excitation light or illumination light to a specimen placed on a stage;
an objective lens opposing the stage and capable of focusing fluorescence or reflected light from the specimen;
an image forming lens for forming an image of the specimen obtained by the objective lens;
an image-capturing unit for capturing the image of the specimen formed by the image-forming lens; and
an optical-path bypass unit disposed on the image-forming lens having a high magnifying power, for bypassing the optical path between the image-forming lens having a high magnifying power and the image-capturing unit so that the straight-line distance from the image-forming lens to the image-capturing unit is matched with that of the image-forming lens having a low magnifying power,
wherein a plurality of the objective lenses having different magnifying powers is provided, and an objective-lens switching mechanism for switching among the objective lenses is provided, and
wherein a plurality of the image-forming lenses having different magnifying powers is provided, and an image-forming-lens switching mechanism for switching among the image-forming lenses is provided.

9. The examination apparatus according to claim 8, wherein optical-path bypass unit is provided with an optical-path-length adjustment unit capable of adjusting the optical path length thereof.

10. The examination apparatus according to claim 8, wherein the optical-path bypass unit is provided with an angle adjustment unit which is capable of adjusting the inclination angle of the optical axis thereof.

11. An examination apparatus comprising:
a light source for emitting excitation light or illumination light to a specimen placed on a stage;
an objective lens opposing the stage and capable of focusing fluorescence or reflected light from the specimen;
an image-forming lens for forming an image of the specimen obtained by the objective lens;
an image-capturing unit for capturing the image of the specimen imaged by the image-forming lens; and
an objective parfocal adjustment mechanism for adjusting the position of the objective lens conjugate with the image location of the image-forming lens,
wherein a plurality of the objective lenses having different magnifying powers is provided, and an objective-lens switching mechanism for switching among the objective lenses is provided, and
wherein a plurality of the image-forming lenses having different magnifying powers is provided, and an image-forming-lens switching mechanism for switching among the image-forming lenses is provided.

12. An examination apparatus comprising:
a light source for emitting excitation light or illumination light to a specimen placed on a stage;
an objective lens opposing the stage and capable of focusing fluorescence or reflected light from the specimen;
an image-forming lens for forming an image of the specimen obtained by the objective lens; and
an image-capturing unit for capturing the image of the specimen formed by the image-forming lens;
wherein a plurality of the objective lenses having different magnifying powers is provided, and an objective-lens switching mechanism for switching among the objective lenses is proved,
wherein a plurality of the image-forming lenses having different magnifying powers is provided, and an image-forming-lens switching mechanism for switching among the image-forming lenses is provided, and
wherein the objective such that lenses, a zooming mechanism, and the image-forming lenses are attached on the same axis disposed in the vertical direction and are attached in a manner such that they are rotatable around the axis.

13. An examination apparatus comprising:
a light source for emitting excitation light or illumination light to a specimen placed on a stage;
an objective lens opposing the stage and capable of focusing fluorescence or reflected light from the specimen;
an image-forming lens for forming an image of the specimen obtained by the objective lens; and an image-capturing unit for capturing the image of the specimen formed by the image-forming lens, wherein a plurality of the objective lens having different magnifying powers is provided, and an objective-lens switching mechanism for switching among the objective lenses is provided, wherein a plurality of the image-forming lenses having different magnifying powers is provided, and an image-forming-lens switching mechanism for switching among the image-forming lenses is provided, wherein the objective lenses, a zooming mechanism, and the image-forming lenses are attached on at least two axes disposed in the vertical direction and are attached in a manner such that they are rotatable around the axes, and wherein the objective lenses and the zooming mechanism are attached in a manner such that they are rotatable around different axes.

14. The examination apparatus according claim 12, further comprising:
a horizontally mounted base;
at least two support stands extending from the base in the vertical direction along the axes; and
a beam member bridged across the upper ends of the support stands,
wherein the image-capturing unit is fixed to the beam member.

15. The examination apparatus according claim 14, wherein the optical axis is disposed at a position away from a plane including the axes of said at least two support stands.

16. The examination apparatus according to claim 14, wherein the objective lenses, the zooming mechanism, and the image-forming lenses are attached to the support stands in a manner such that they are rotatable around the axis of the support stand by an assembly including a cylindrical fixed bracket fixed to the support stand by being engaged with the upper portion of the support stand; a movable bracket for fixing the objective lenses, the zooming mechanism, and the image-forming lenses; and a bearing for installing the movable bracket to the fixed bracket in a manner such that the movable bracket is horizontally rotatable.

17. The examination apparatus according to claim 14, wherein the base includes a first base for fixing the stage and a second base provided above the first base with a space provided therebetween, and wherein the first base and the second base are fixed by spacing members and the support stands are fixed to the second base.

18. The examination apparatus according to claim 17, wherein the spacing members are replaceable.

19. An examination apparatus comprising:
a light source for emitting excitation light or illumination light to a specimen placed on a stage;
an objective lens opposing the stage and capable of focusing fluorescence or reflected light from the specimen;
an image-forming lens for forming an image of the specimen obtained by the objective lens; and
an image-capturing unit for capturing the image of the specimen formed by the image-forming lens;
wherein a plurality of the objective lenses having different magnifying powers is provided, and an objective-lens switching mechanism for switching among the objective lenses is provided,
wherein a plurality of the image-forming lenses having different magnifying powers is provided, and an image-forming lens switching mechanism for switching among the image-forming lenses is provided, and
wherein the image-capturing unit is replaceable.

20. An examination apparatus comprising:
a light source for emitting excitation light or illumination light to a specimen placed on a stage;
an objective lens opposing the stage and capable of focusing fluorescence or reflected light from the specimen;
an image-forming lens for forming an image of the specimen obtained by the objective lens; and
an image-capturing unit for capturing the image of the specimen formed by the image-forming lens;
wherein a plurality of the objective lenses having different magnifying powers is provided, and an objective-lens switching mechanism for switching among the objective lenses is provided,
wherein a plurality of the image-forming lenses having different magnifying powers is provided, and an image-forming lens switching mechanism for switching among the image-forming lenses is provided, and
wherein the image-capturing unit is disposed in a manner such that it is rotatable around the optical axis.

21. A fluoroscopy apparatus comprising:
a laser light source for emitting excitation light to a specimen placed on a stage;
a plurality of lens groups, each group including an objective lens for magnifying fluorescence from the specimen, the objective lens opposing the stage, and an image-forming lens for imaging the fluorescence from the specimen magnified by the objective lens;
an image-capturing unit for capturing the fluorescence from the specimen imaged by the image-forming lens; and
a lens-group-switching mechanism for switching among the lens groups.

22. The fluoroscopy apparatus according to claim 21, further comprising:
a processing unit for carrying out spectral deconvolution processing on the captured fluorescence.

23. The fluoroscopy apparatus according to claim 22, further comprising:
a processing unit for carrying out spectral blind deconvolution processing on the captured fluorescence.

24. An examination apparatus comprising:
a light source for emitting excitation light or illumination light to a specimen placed on a stage;
an objective lens opposing the stage and capable of focusing fluorescence or reflected light from the specimen;
an image-forming lens for forming an image of the specimen obtained by the objective lens; and
an image-capturing unit for capturing the image of the specimen formed by the image-forming lens;
wherein a plurality bf the objective lenses having different magnifying powers is provided, and an objective-lens switching mechanism for switching among the objective lenses is provided,
wherein a plurality of the image-forming lenses having different magnifying powers is provided and an image-forming-lens switching mechanism for switching among the image-forming lenses is provided, and
wherein
the specimen is a living organism, an organ, or tissue,
the light source is an illumination device for internally illuminating the specimen, and
the image-capturing unit is an image-capturing device for obtaining an optical image of at least one of a transmission image and a fluorescence image of the specimen by capturing an external image of the specimen.

25. The examination apparatus according to claim 24, wherein the illumination device includes a light source for emitting illumination light or excitation light and a light-emitting unit for externally emitting the illumination light or the excitation light, and wherein the light-emitting unit is guidable into the specimen.

26. The examination apparatus according to claim 24, wherein the living organism is a living mammal selected from the group consisting of mouse, rat rabbit, cat, dog, pig, cow, sheep, goat horse, monkey, gorilla, chimpanzee, and human.

27. The examination apparatus according to claim 24, wherein the organ is an organ selected from the group consisting of brain, lung, liver, spleen, bone marrow, thymus, heart, lymph, blood, bone, cartilage, pancreas, liver, gall bladder, stomach, intestine, testis, ovary, uterus, rectum, nervous system, gland, and blood vessel.

28. The examination apparatus according to claim 24, wherein the tissue is a three-dimensional structure of a plurality of cells.

* * * * *